US009132210B2

(12) United States Patent
Mooney et al.

(10) Patent No.: US 9,132,210 B2
(45) Date of Patent: Sep. 15, 2015

(54) SCAFFOLDS FOR CELL TRANSPLANTATION

(71) Applicants: President and Fellows of Harvard College, Cambridge, MA (US); Regents of the University of Michigan, Ann Arbor, MI (US)

(72) Inventors: David J. Mooney, Sudbury, MA (US); Omar Abdel-Rahman Ali, Cambridge, MA (US); Eduardo Alexandre Barros E Silva, Davis, CA (US); Hyun Joon Kong, Cambridge, MA (US); Elliot Earl Hill, Jr., Ypsilanti, MO (US); Tanyarut Boontheekul, Bangkok (TH)

(73) Assignees: President and Fellows of Harvard College, Cambridge, MA (US); Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/223,759

(22) Filed: Mar. 24, 2014

(65) Prior Publication Data
US 2015/0024026 A1 Jan. 22, 2015

Related U.S. Application Data

(63) Continuation of application No. 13/305,088, filed on Nov. 28, 2011, now Pat. No. 8,932,583, which is a continuation of application No. 11/638,796, filed on Dec. 13, 2006, now Pat. No. 8,067,237.

(60) Provisional application No. 60/814,134, filed on Jun. 16, 2006, provisional application No. 60/749,998, filed on Dec. 13, 2005.

(51) Int. Cl.
A61L 27/58 (2006.01)
A61L 27/36 (2006.01)
A61L 27/54 (2006.01)
A61K 39/00 (2006.01)
A61L 27/38 (2006.01)
A61L 27/56 (2006.01)

(52) U.S. Cl.
CPC ............. *A61L 27/58* (2013.01); *A61K 39/0011* (2013.01); *A61L 27/3633* (2013.01); *A61L 27/38* (2013.01); *A61L 27/54* (2013.01); *A61L 27/56* (2013.01); *A61L 2300/252* (2013.01); *A61L 2300/414* (2013.01); *A61L 2300/426* (2013.01); *A61L 2300/438* (2013.01); *A61L 2300/604* (2013.01); *A61L 2300/606* (2013.01)

(58) Field of Classification Search
CPC . A61L 27/58; A61L 27/3633; A61K 39/0011
See application file for complete search history.

(56) References Cited

U.S. PATENT DOCUMENTS

| | | | |
|---|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,427,602 B1 | 9/2008 | Shea et al. |
| 7,575,759 B2 | 8/2009 | Murphy et al. |

(Continued)

FOREIGN PATENT DOCUMENTS

CN 101655611 A 2/2010
EP 0562862 A1 9/1993
(Continued)

OTHER PUBLICATIONS

Li et al. (Biotechnol. Bioprocess Eng. 2001; 6(5): 31-325).*
Zhao et al (Biomaterials 2005; 26: 5048-5063, available online Feb. 24, 2005).*
Villadangos (Molecular Immunology. 2001; 38: 329-346).*
"Antigens and Receptors." *Immunology*. Doan et al., eds. Philadelphia: Wolters Kluwer/Lippincott Williams & Wilsons. (2008):11-23.
"Collagen: The Fibrous Proteins of the Matrix." *Molecular Cell Biology*. Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
"Wound Management: Past, Present, and Future." *Clinicians' Pocket Guide to Chronic Wound Repair*. Mulder et al., eds. Springhouse, PA: Springhouse Corporation. (1998):85-90.

(Continued)

*Primary Examiner* — Scott Long
(74) *Attorney, Agent, or Firm* — Mintz Levin Cohn Ferris Glovsky and Popeo, P.C.; Ingrid A. Beattie

(57) ABSTRACT

A device that includes a scaffold composition and a bioactive composition with the bioactive composition being incorporated into or coated onto the scaffold composition such that the scaffold composition and/or a bioactive composition controls egress of a resident cell or progeny thereof. The devices mediate active recruitment, modification, and release of host cells from the material.

37 Claims, 17 Drawing Sheets

(56) References Cited

U.S. PATENT DOCUMENTS

| | | | |
|---|---|---|---|
| 7,790,699 B2 | 9/2010 | Melvik et al. | |
| 8,067,237 B2 | 11/2011 | Mooney et al. | |
| 8,188,058 B2 | 5/2012 | Hackam et al. | |
| 8,273,373 B2 | 9/2012 | Alsberg et al. | |
| 8,728,456 B2 | 5/2014 | Sands et al. | |
| 2002/0131853 A1 | 9/2002 | Nagasawa | |
| 2002/0150604 A1 | 10/2002 | Yi et al. | |
| 2003/0075822 A1 | 4/2003 | Slivka et al. | |
| 2003/0082806 A1* | 5/2003 | Berenson et al. | 435/372 |
| 2003/0095994 A1 | 5/2003 | Geistlich et al. | |
| 2003/0100527 A1 | 5/2003 | Krieg et al. | |
| 2003/0232895 A1 | 12/2003 | Omidian et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0220111 A1 | 11/2004 | Kleinman et al. | |
| 2004/0242469 A1 | 12/2004 | Lee et al. | |
| 2004/0242482 A1 | 12/2004 | Gehring et al. | |
| 2005/0002915 A1 | 1/2005 | Atala et al. | |
| 2005/0053667 A1 | 3/2005 | Irvine et al. | |
| 2005/0079159 A1 | 4/2005 | Shastri et al. | |
| 2005/0090008 A1 | 4/2005 | Segura et al. | |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 | 4/2007 | Sandler et al. | |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044990 A1 | 2/2008 | Lee | |
| 2008/0051490 A1 | 2/2008 | Williams et al. | |
| 2008/0138416 A1 | 6/2008 | Rauh et al. | |
| 2008/0206308 A1 | 8/2008 | Jabbari et al. | |
| 2008/0268052 A1 | 10/2008 | Voytik-Harbin et al. | |
| 2009/0017096 A1 | 1/2009 | Lowman et al. | |
| 2009/0192079 A1 | 7/2009 | Santos et al. | |
| 2009/0238853 A1 | 9/2009 | Liu et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0159008 A1 | 6/2010 | Barron et al. | |
| 2010/0189760 A1 | 7/2010 | Schaffer et al. | |
| 2010/0190741 A1 | 7/2010 | Cohen et al. | |
| 2010/0272771 A1 | 10/2010 | Harlow et al. | |
| 2011/0020216 A1 | 2/2011 | Mooney et al. | |
| 2011/0117170 A1 | 5/2011 | Cao et al. | |
| 2012/0100182 A1 | 4/2012 | Mooney et al. | |
| 2012/0121539 A1 | 5/2012 | Sands et al. | |
| 2012/0122218 A1 | 5/2012 | Huebsch et al. | |
| 2012/0256336 A1 | 10/2012 | Yano et al. | |
| 2012/0264599 A1 | 10/2012 | Komatsu et al. | |
| 2012/0329791 A1 | 12/2012 | Ashwell et al. | |
| 2013/0029030 A1 | 1/2013 | Larsen | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0079752 A1 | 3/2014 | Huebsch et al. | |
| 2014/0112990 A1 | 4/2014 | Bencherif et al. | |
| 2014/0178964 A1 | 6/2014 | Mooney et al. | |
| 2014/0193488 A1 | 7/2014 | Kim et al. | |
| 2014/0227327 A1 | 8/2014 | Bencherif et al. | |
| 2014/0234423 A1 | 8/2014 | Sands et al. | |
| 2015/0072009 A1 | 3/2015 | Kim et al. | |

FOREIGN PATENT DOCUMENTS

| | | |
|---|---|---|
| EP | 1452191 A2 | 9/2004 |
| EP | 1561481 A2 | 8/2005 |
| JP | 2005170816 A | 6/2005 |
| WO | WO-9616086 A1 | 5/1996 |
| WO | WO-9812228 A1 | 3/1998 |
| WO | WO-9951259 A2 | 10/1999 |
| WO | WO-0135932 A2 | 5/2001 |
| WO | WO-0216557 A2 | 2/2002 |
| WO | WO-03020884 A2 | 3/2003 |
| WO | WO-2004006990 A2 | 1/2004 |
| WO | WO-2004030706 A2 | 4/2004 |
| WO | WO-2004089413 A1 | 10/2004 |
| WO | WO-2005026318 A2 | 3/2005 |
| WO | WO-205037293 A1 | 4/2005 |
| WO | WO-2005037190 A2 | 4/2005 |
| WO | WO-2005046748 A1 | 5/2005 |
| WO | WO-2005072088 A2 | 8/2005 |
| WO | WO-2006119619 A1 | 11/2006 |
| WO | WO-2006136905 A2 | 12/2006 |
| WO | WO-2007030901 A1 | 3/2007 |
| WO | WO-2007064152 A1 | 6/2007 |
| WO | WO-2007078196 A1 | 7/2007 |
| WO | WO-2007107739 A1 | 9/2007 |
| WO | WO-2007150020 A1 | 12/2007 |
| WO | WO-2008018707 A1 | 2/2008 |
| WO | WO-2009002401 A2 | 12/2008 |
| WO | WO-2009005769 A2 | 1/2009 |
| WO | WO-2009074341 A1 | 6/2009 |
| WO | WO-2009102465 A2 | 8/2009 |
| WO | WO-2009146456 A1 | 12/2009 |
| WO | WO-2009155583 A1 | 12/2009 |
| WO | WO-2010120749 A2 | 10/2010 |
| WO | WO-2011014871 A1 | 2/2011 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A1 | 12/2011 |
| WO | WO-2012009611 A2 | 1/2012 |
| WO | WO-2012019049 A1 | 2/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |
| WO | WO-2013158673 A1 | 10/2013 |

OTHER PUBLICATIONS

Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.

Agache et al. "Mechanical Properties and Young's Modulus of Human Skin in Vivo." *Arch. Dermatol. Res.* 269.3(1980):221-232.

Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.

Aguado et al. "Improving Viability of Stem Cells During Syringe Needle Flow Through the Design of Hydrogel Cell Carriers." *Tissue Eng. Part A.* 18.7-8(2012):806-815.

Akira et al. "Pathogen Recognition and Innate Immunity." *Cell.* 124.4(2006):783-801.

Akira et al. "Toll-Like Receptors: Critical Proteins Linking Innate and Acquired Immunity." *Nat. Immunol.* 2.8(2001):675-680.

Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.

Aldhous. "Print Me a Heart and a Set of Arteries." *New Scientist.* 2547(2006):19.

(56) References Cited

OTHER PUBLICATIONS

Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Alsberg et al. "Regulating Bone Formation via Controlled Scaffold Design." *J. Dent. Res.* 82.11(2003):903-908.
American Diabetes Association. "Standards of Medical Care in Diabetes—2013." *Diabetes Care.* 36.S1(2013):S11-S66.
Anderson et al. "Biomaterial Microarrays: Rapid, Microscale Screening of Polymer-Cell Interaction." *Biomaterials.* 26.23(2005):4892-4897.
Anderson et al. "Nanoliter-Scale Synthesis of Arrayed Biomaterials and Application to Human Embryonic Stem Cells." *Nat. Biotechnol.* 22.7(2004):863-866.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.
Annaidh et al. "Characterization of the Anistropic Mechanical Properties of Excised Human Skin." *J. Mech. Behav. Biomed. Mater.* 5.1(2012):139-148.
Arany et al. "At the Edge of Translation—Materials to Program Cells for Directed Differentiation." *Oral Dis.* 17.3(2011):241-251.
Aschner et al. "Metabolic Memory for Vascular Disease in Diabetes." *Diabetes Technol. Ther.* 14.S1(2012):S68-S74.
Atala et al. "Endoscopic Treatment of Vesicoureteral Reflux with a Chondrocyte-Alginate Suspension." *J. Urol.* 152(1994):641-643.
Aubin et al. "Directed 3D Cell Alignment and Elongation in Microengineered Hydrogels." *Biomater.* 31.27(2010):6941-6951.
Augst et al. "Alginate Hydrogels as Biomaterials." *Macromol. Biosci.* 6(2006):623-633.
Babensee et al. "Host Response to Tissue Engineered Device." *Adv. Drug Deli. Rev.* 33.1-2(1998):111-139.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Balakrishna et al. "Structural Correlates of Antibacterial and Membrane-Permeabilizing Activities in Acylpolyamines." *Antimicrob. Agents Chemother.* 50.3(2006):852-861.
Banchereau et al. "Dendritic Cells and the Control of Immunity." *Nature.* 392.6673(1998):245-252.
Bar-Cohen et al. "Electroactive Polymer Actuators and Sensors." *MRS Bullet.* 33.3(2008):173-181.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math. Biol.* 61.3(1999):483-505.
Bates. "Improved Muscle Regeneration by Combining VEGF With IGF1." *Regen. Med.* 5.6(2010):853-854.
Beaucage et al. "The Functionalization of Oligonucleotides via Phosphoramidite Derivatives." *Tetrahedron.* 49.10(1993):1925-1963.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Becker et al. "Cytological Demonstration of the Clonal Nature of Spleen Colonies Derived from Transplanted Mouse Marrow Cells." *Nature.* 197(1963):452-454.
Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bergstraesser et al. "Stimulation and Inhibition of Human Mammary Epithelial Cell Duct Morphogenesis In Vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1(2013):35-42.
Bilodeau et al. "Regular Pyramid Punch Problem." *J. Appl. Mech.* 59.3(1992):519-523.
Bischoff. "Proliferation of Muscle Satellite Cells on Intact Myofibers in Culture." *Dev. Biol.* 115.1(1986):129-139.
Blanes et al. "Induction of Autoimmune Diabetes by Oral Administration of Autoantigen." *Science.* 274.5293(1996):1707-1709.
Blumenthal et al. "Polyurethane Scaffolds Seeded with Genetically Engineered Skeletal Myoblasts: A Promising Tool to Regenerate Myocardial Function." *Artificial Organs.* 34.2(2010): E46-E54.

(56) References Cited

OTHER PUBLICATIONS

Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Controlling Alginate Gel Degradation Utilizing Partial Oxidation and Bimodal Molecular Weight Distribution." *Biomaterials.* 26.15(2005):2455-2465.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Degradation of Partially Oxidized Alginate and its Potential Application for Tissue Engineering." *Biotechnol. Prog.* 17.5(2001):945-950.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkmann et al. "Neutrophil Extracellular Traps Kill Bacteria." *Science.* 303.5663(2004):1532-1535.
Brouwers et al. "Can the Growth Factors PTHrP, Ihh and VEGF, Together Regulate the Development of a Long Bone?" *J. Biomech.* 39.15(2006):2774-2782.
Broxmeyer et al. "Insights into the Biology of Cord Blood Stem/Progenitor Cells." *Cell Prolif.* 44.S1(2011):55-59.
Bryant et al. "Photo-Patterning of Porous Hydrogels for Tissue Engineering." *Biomater.* 28.19(2007):2978-2986.
Buckwalter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1(201 1):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Burdick et al. "Stimulation of Neurite Outgrowth by Neurotrophins Delivered From Degradable Hydrogels." *Biomater.* 27.3(2006):452-459.
Bégué et al. "Vaccination Against Human Papillomavirus. Implementation and Efficacy Against Cervical Cancer Control." *Bull. Acad. Natl. Med.* 191.9(2007):1805-1816. (French original and English abstract).
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Cameron et al. "The Influence of Substrate Creep on Mesenchymal Stem Cell Behaviour and Phenotype." *Biomater.* 32.26(2011):5979-5993.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Functional Human Vascular Network Generated in Photocrosslinkable Gelatin Methacrylate Hydrogels." *Adv. Funct. Mater.* 22.10(2012):2027-2039.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Chiang et al. "Whole Tumor Antigen Vaccines." *Semin. Immunol.* 22.3(2010):132-143.
Choi et al. "In Vitro Mineralization by Preosteoblasts in Poly(DL-lactide-*co*-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Choi. "Replacement Organs, Hot Off the Press." *New Scientist.* 177.2379(2003):16.
Chou et al. "Characterization of Photocross Linked Alginate Hydrogels for Nucleus Pulposus Cell Encapsulation." *J. Biomed. Mater. Res. A.* 91A.1(2009):187-194.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clark et al. "Myosin II and Mechanotransduction: A Balancing Act." *Trends Cell Biol.* 17.4(2007):178-186.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.

(56) References Cited

OTHER PUBLICATIONS

Comisar et al. "Engineering RGD Nanopatterned Hydrogels to Control Preosteoblast Behavior: A Combined Computational and Experimental Approach." *Biomaterials*. 28(2007):4409-4417.
Conboy et al. "The Regulation of Notch Signaling Controls Satellite Cell Activation and Cell Fate Determination in Postnatal Myogenesis." *Dev. Cell*. 3.3(2002):397-409.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res*. 89A.2(2009):304-316.
Conn et al. "Purification of a Glycoprotein Vascular Endothelial Cell Mitogen From a Rat Glioma-Derived Cell Line." *PNAS*. 87.4(1990):1323-1327.
Cook et al. "A Sialomucopeptide Liberated by Trypsin from the Human Erythrocyte." *Nature*. 188(1960):1011-1012.
Cooper et al. "Extended Amplification In Vitro and Replicative Senescence: Key Factors Implicated in the Success of Human Myoblast Transplantation." *Hum. Gene Ther*. 14(2003):1169-1179.
Cooper. "Metabolic Memory: Implications for Diabetic Vascular Complications." *Pediatr. Diabetes*. 10.5(2009):343-346.
Cornelison et al. "Single-Cell Analysis of Regulatory Gene Expression in Quiescent and Activated Mouse Skeletal Muscle Satellite Cells." *Dev. Biol*. 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol*. 239.1(2001):79-94.
Coulson et al. "Flow of Fluids through Granular Beds and Packed Columns." *Chemical Engineering*. New York: Pergamon Press. 2(1978):125-171.
Crameri et al. "Improved Green Fluorescent Protein by Molecular Evolution Using DNA Shuffling." *Nat. Biotechnol*. 14.3(1996):315-319.
Cuda et al. "In Vitro Actin Filament Sliding Velocities Produced by Mixtures of Different Types of Myosin." *Biophys. J*. 72.4(1997):1767-1779.
Cukierman et al. "Taking Cell-Matrix Adhesions to the Third Dimension." *Science*. 294.5547(2001):1708-1712.
Cullen et al. "Investigation of Vascular Endothelial Growth Factor Effects on Pulmonary Endothelial Monolayer Permeability and Neutrophil Transmigration." *Gen. Pharmacol*. 35.3(2000):149-157.
Curiel et al. "Tumor Immunotherapy: Inching Toward the Finish Line." *J. Clin. Invest*. 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med*. 198.2(2003):293-303.
Dar et al. "Optimization of Cardiac Cell Seeding and Distribution in 3D Porous Alginate Scaffolds." *Biotechnol. Bioeng*. 80(2002):305-312.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol*. 165.1(2000):49-58.
David et al. "The in vitro Desensitization of Sensitive Cells by Trypsin." *J. Exp. Med*. 120(1964):1189-1200.
Davies et al. "Antibody-Antigen Complexes." *Annu. Rev. Biochem*. 59(1990):439-473.
de Jong et al. "Regulation of Notch Signaling Genes During BMP2-Induced Differentiation of Osteoblast Precursor Cells." *Biochem. Biophys. Res. Commun*.320(2004):100-107.
De Temmerman et al. "Particulate Vaccines: On the Quest for Optimal Delivery and Immune Response." *Drug Disc. Today*. 16.13/14(2011):569-582.
Dembo et al. "Stresses at the Cell-to-Substrate Interface During Locomotion of Fibroblasts." *Biophys. J*. 76.4(1999):2307-2316.
den Haan et al. "CD8+ by not CD8− Dendritic Cells Cross-Prime Cytotoxic T Cells In Vivo." *J. Exp. Med*. 192.12(2000):1685-1696.
Dennis et al. "Excitability and Contractility of Skeletal Muscle Engineered From Primary Cultures and Cell Lines." *Am. J. Physiol. Cell Physiol*. 280(2001):C288-C295.
Dennis et al. "Excitability and Isometric Contractile Properties of Mammalian Skeletal Muscle Constructs Engineered in vitro." *In Vitro Cell Dev. Biol. Anim*. 36.5(2000):327-335.
Dexter et al. "Conditions Controlling the Proliferation of Haemopoietic Stem Cells In Vitro." *J. Cell. Physiol*. 91.3(1977):335-344.
Di Nicola et al. "Human Bone Marrow Stromal Cells Suppress T-Lymphocyte Proliferation Induced by Cellular or Nonspecific Mitogenic Stimuli." *Blood*. 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am*. 75.1(1993):92-105.
Dieu et al. "Selective Recruitment of Immature and Mature Dendritic Cells by Distinct Chemokines Expressed in Different Anatomic Sites." *J. Exp. Med*. 188.2(1988):373-386.
Diridollou et al. "Skin Ageing: Changes of Physical Properties of Human Skin in vivo." *J. Cosmet. Sci*. 23.6(2001):353-362.
Discher et al. "Tissue Cells Feel and Respond to the Stiffness of their Substrate." *Science*. 310.5751(2005):1139-1143.
Disis et al. "Granulocyte-Macrophage Colony-Stimulating Factor: An Effective Adjuvant for Protein and Peptide-Based Vaccines." *Blood*. 88.1(1996):202-210.
Doan et al. "Subcellular Localization of a Sporulation Membrane Protein is Achieved Through a Network of Interactions Along and Across the Septum." *Mol. Microbiol*. 55.6(2005):1767-1781.
Donati et al. "New Hypothesis on the Role of Alternating Sequences in Calcium-Alginate Gels." *Biomacromol*. 6.2(2005):1031-1040.
Dor et al. "Making Vascular Networks in the Adult: Branching Morphogenesis Without a Roadmap." *Trends Cell Biol*. 13.3(2003):131-136.
Douay et al. "Ex vivo Production of Human Red Blood Cells from Hematopoietic Stem Cells: What is the Future in Transfusion?" *Transfus. Med. Rev*. 21.2(2007):91-100.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS*. 90.8(1993):3539-3543.
Dranoff. "Cyotkines in Cancer Pathogenesis and Cancer Therapy." *Nat. Rev. Cancer*. 4.1(2004):11-22.
Dranoff. "GM-CSF-Based Cancer Vaccines." *Immunol. Rev*. 188(2002):147-154.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol*. 23.10(2005):2346-2357.
DuFort et al. "Balancing Forces: Architectural Control of Mechanotransduction." *Nat. Rev. Mol. Cell Biol*. 12.5(2011):308-319.
Dupont et al. "Role of YAP/TAZ in Mechanotransduction." *Nature*. 474.7350(2011):179-183.
Edwards et al. "Evaluation of Biomechanical Properties of Human Skin." *Clin. Dermatol*. 13.4(1995):375-380.
Egholm et al. "Peptide Nucleic Acids (PNA). Oligonucleotide Analogues with an Achiral Peptide Backbone." *J. Am. Chem. Soc*. 114.5(1992):1895-1897.
Egholm et al. "PNA Hybridizes to Complementary Oligonucleotides Obeying the Watson-Crick Hydrogen-Bonding Rules." *Nature*. 365.6446(1993):566-568.
Ehrbar et al. "Endothelial Cell Proliferation and Progenitor Maturation by Fibrin-Bound VEGF Variants with Differential Susceptibilities to Local Cellular Activity." *J. Control. Release*. 101(2004):93-109.
Eiselt et al. "Porous Carriers for Biomedical Applications Based on Alginate Hydrogels." *Biomat*. 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J*. 34.2(2008):52-67.

(56) References Cited

OTHER PUBLICATIONS

Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature*. 419.6904(2002):304-308.
Eldar et al. "Self-Enhanced Ligand Degradation Underlies Robustness of Morphogen Gradients." *Dev. Cell*. 5.4(2003):635-646.
Eming et al. "Inflammation in Wound Repair: Molecular and Cellular Mechanisms." *J. Invest. Dermatol*. 127.3(2007):514-525.
Engler et al. "Matrix Elasticity Directs Stem Cell Lingeage Specification." *Cell*. 126.4(2006):677-689.
Engler et al. "Microtissue Elasticity: Measurements by Atomic Force Microscopy and its Influence on Cell Differentiation." *Methods Cell. Biol*. 83(2007):521-545.
Engler et al. "Substrate Compliance Versus Ligand Density in Cell on Gel Response." *Biophys. J*. 86.1 Pt1(2004):617-628.
Ennett et al. "Temporally Regulated Delivery of VEGF in vitro and in vivo." *J. Biomed. Mater. Res. A*. 79.1(2006):176-184.
Exposito et al. "The Fibrallar Collagen Family." *Int. J. Mol. Sci*. 11.2(2010):407-426.
Faissner et al. "Boundaries and Inhibitory Molecules in Developing Neural Tissues." *Glia*. 13.4(1995):233-254.
Falanga. "Wound Healing and its Impairment in the Diabetic Foot." *Lancet*. 366.9498(2005):1736-1743.
Falsey et al. "Peptide and Small Molecule Microarray for High Throughput Cell Adhesion and Functional Assays." *Bioconjug. Chem*. 12.3(2001):346-353.
Farrar et al. "T Helper Subset Development: Roles of Instruction, Selection, and Transcription." *J. Clin. Invest*. 109.4(2002):431-435.
Fauquemberque et al. "HLA-A*0201-Restricted CEA-Derived Peptide CAP1 is not a Suitable Target for T-Cell-Based Immunotherapy." *J. Immunother*. 33.4(2010):402-413.
Ferrara et al. "Angiogenesis as a Therapeutic Target." *Nature*. 438.7070(2005):967-974.
Ferrara et al. "Discovery and Development of Bevacizumab, an Anti-VEGF Antibody for Treating Cancer." *Nat. Rev. Drug Discov*. 3.5(2004):391-400.
Fischer et al. "A Brilliant Monomeric Red Fluorescent Protein to Visualize Cytoskeleton Dynamics in *Dictyostelium*." *FEBS Lett*. 577.1-2(2004):227-232.
Fischer et al. "Visualizing Cytoskeleton Dynamics in Mammalian Cells Using a Humanized Variant of Monomeric Red Fluorescent Protein." *FEBS Lett*. 580.10(2006):2495-2502.
Fisher et al. "The Study of Protein Mechanics with the Atomic Force Microscope." *Trends Biochem. Sci*. 24.10(1999):379-384.
Folkman. "Angiogenesis." *Annu. Rev. Med*. 57(2006):1-18.
Fonseca et al. "Capitalizing on the Immunogenicity of Dying Tumor Cells." *Clin. Cancer Res*. 14.16(2008):1603-1608.
Fontaine et al. "Surgical Treatment of Peripheral Circulation Disorders." *Helv. Chir. Acta*. 21.56(1954):499-533. (German Original, No English Translation Available).
Fox. "Management of Worsening Multiple Sclerosis with Mitoxantrone: A Review." *Clin. Ther*. 28.4(2006):461-474.
Friedenstein et al. "Fibroblast Precursors in Normal and Irradiated Mouse Hematopoietic Organs." *Exp. Hematol*. 4.5(1976):267-274.
Friedrich et al. "Promoter Traps in Embryonic Stem Cells: A Genetic Screen to Identify and Mutate Developmental Genes in Mice." *Genes Dev*. 5(1991):1513-1523.
Fukushima et al. "The Use of an Antifibrosis Agent to Improve Muscle Recovery After Laceration." *Am. J. Sports Med*. 29.4(2001):394-402.
Gamvrellis et al. "Vaccines that Facilitate Antigen Entry into Dendritic Cells." *Immunol. Cell Biol*. 82(2004):506-516.
Gardel et al. "Traction Stress in Focal Adhesions Correlates Biphasically with Actin Retrograde Flow Speed." *J. Cell Biol*. 183.6(2008):999-1005.
Gasic et al. "Removal and Regeneration of the Cell Coating in Tumour Cells." *Nature*. 196(1962):170.
Gauthier et al. "Temporary Increase in Plasma Membrane Tension Coordinates the Activation of Exocytosis and Contraction During Cell Spreading." *PNAS*. 108.35(2011):14467-14472.
Geerligs et al. "Linear Viscoelastic Behavior of Subcutaneous Adipose Tissue." *Biorheol*. 45.6(2008):677-688.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CB171013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000230.2, Dec. 17, 2012.
GenBank Accession No. NM_000514.3, Aug. 19, 2012.
GenBank Accession No. NM_000572.2, May 18, 2014.
GenBank Accession No. NM_000601.4, Nov. 25, 2012.
GenBank Accession No. NM_000614.3, Sep. 9, 2012.
GenBank Accession No. NM_000638.3, May 4, 2014.
GenBank Accession No. NM_000660.4, Dec. 9, 2012.
GenBank Accession No. NM_000758.3, May 4, 2014.
GenBank Accession No. NM_000800.3, Mar. 4, 2012.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_001845.4, May 3, 2014.
GenBank Accession No. NM_001901.2, May 18, 2014.
GenBank Accession No. NM_002421.3_05112014.
GenBank Accession No. NM_002506.2, Dec. 9, 2012.
GenBank Accession No. NM_002632.4, May 4, 2011.
GenBank Accession No. NM_002982.3, May 3, 2014.
GenBank Accession No. NM_003236.2, Aug. 21, 2011.
GenBank Accession No. NM_003263.3, Jan. 5, 2013.
GenBank Accession No. NM_003264.3, Jan. 6, 2013.

(56) References Cited

OTHER PUBLICATIONS

GenBank Accession No. NM_003268.5, Nov. 25, 2012.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_006068.4, Oct. 28, 2012.
GenBank Accession No. NM_015719.3, Feb. 26, 2014.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001096124.1, Dec. 16, 2012.
GenBank Accession No. NP_001836.2, May 3, 2014.
GenBank Accession No. NP_001892.1, May 18, 2014.
GenBank Accession No. NP_002010.2, Dec. 9, 2012.
GenBank Accession No. NP_002973.1, May 3, 2014.
GenBank Accession No. NP_003239.2, Feb. 18, 2014.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_006059.2, Oct. 28, 2012.
GenBank Accession No. NP_056534.2, Feb. 26, 2014.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Glasbey et al. "Image Analysis and Three-Dimensional Modelling of Pores in Soil Aggregates." *Eur. J. Soil Sci.* 42.2(1991):479-486.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Graessley. "Entangled Linear, Branched and Network Polymer Systems—Molecular Theories." *Adv. Poly. Sci.* 47(1982):67-117.

Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.*130.10(2004):1191-1196.
Gros et al. "A Common Somitic Origin for Embryonic Muscle Progenitors and Satellite Cells." *Nature.* 435(2005):954-958.
Guillaume et al. "Two Abundant Proteasome Subtypes that Uniquely Process Some Antigens Presented by HLA Class I Molecules." *PNAS.* 107.43(2010):18599-18604.
Gullberg et al. "Extracellular Matrix and Its Receptors During Development." *Int. J. Dev. Biol.* 39(1995):845-854.
Guo et al. "Droplet Microfluidics for High-Throughput Biological Assays." *Lab Chip.* 12.12(2012):2146-2155.
Gupta et al. "Magnetically Controlled Targeted Micro-Carrier Systems." *Life Sci.* 44.3(1989):175-186.
Gurkan et al. "The Mechanical Environment of Bone Marrow: A Review." *Ann. Biomed. Eng.* 36.12(2008):1978-1991.
Gussoni et al. "Dystrophin Expression and in the *mdx* Mouse Restored by Stem Cell Transplantation." *Nature.* 401(1999):390-394.
Halim et al. "Biologic and Synthetic Skin Substitutes: An Overview." *Indian J. Plast. Surg.* 43(2010):S23-S28.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8 (2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harris. "Classification, Diagnostic Criteria, and Screening for Diabetes." *Diabetes in America.* NIH Publication No. 95-1468. Chapter 2. (1995):15-36.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Heath. "Cells for Tissue Engineering." *Trends Biotechnol.* 18.1(2006):17-19.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts can Give Rise to Functional Satellite Cells as Identified Using the Myf5nlacZI+ Mouse." *Gene Ther.* 8(2001):778-783.

(56) References Cited

OTHER PUBLICATIONS

Hildner et al. "Batf3 Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Holland et al. "Transforming Growth Factor-β1 Release from Oligo(poly(ethylene glycol) Fumarate) Hydrogels in Conditions that Model the Cartilage Wound Healing Environment." *J. Control. Release.* 94(2004):101-114.
Horsley et al. "IL-4 Acts as a Myoblast Recruitment Factor During Mammalian Muscle Growth." *Cell.* 1 13.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Ishihara et al. "Roles of Bradykinin in Vascular Permeability and Angiogenesis in Solid Tumor." *Int. Immunopharmacol.* 2.4(2002):499-509.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Jain. "Molecular Regulation of Vessel Maturation." *Nat. Med.* 9.6(2003):685-693.
Jain. "The Manufacturing Techniques of Various Drug Loaded Biodegradable Poly(lactide-*co*-glycolide) (PLGA) Devices." *Biomater.* 21.23(2000):2475-2490.

Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Janmey et al. "From Tissue Mechanics to Transcription Factors." *Differentiation.* 86.3(2013):112-120.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primordia." *Development.* 126.22(1999):4997-5009.
Jiang et al. "Two-Piconewton Slip Bond Between Fibronectin and the Cytoskeleton Depends on Talin." *Nature.* 424.6946(2003):334-337.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-EB-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Jokinen et al. "Integrin-Mediated Cell Adhesion to Type I Collagen Fibrils." *J. Biol. Chem.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Juntanon et al. "Electrically Controlled Release of Sulfosalicylic Acid from Crosslinked Poly(Vinyl Alcohol) Hydrogel." *Int. J. Pharm.* 356(2008):1-11.
Kang et al. "Effect of Porous Structure on the Degradation of Freeze-Dried Gelatin Hydrogels." *J. Bioact. Compat. Poly.* 14.4(1999):331-343.
Kanzler et al. "Therapeutic Targeting of Innate Immunity with Toll-Like Receptor Agaonists and Antagonists." *Nat. Med.* 13.5(2007):552-559.
Katayama et al. "Integrated Analysis of the Genome and the Transcriptome by FANTOM." *Brief Bioinform.* 5.3(2004):249-258.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Khownium et al. "Novel Endotoxin-Compounds with Terephthalaldehyde-bis-guanyllhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kim et al. "Multifunctional Capsule-in-Capsules for Immunoprotection and Trimodal Imaging." *Angew. Chem. Int. Ed.* 50.10(2011):2317-2321.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klein et al. "Cell-Cycle Control by Physiological Matrix Elasticity and In Viivo Tissue Stiffening." *Curr. Biol.* 19.18(2009):1511-1518.
Klinman. "Immunotherapeutic Uses of CpG Oligodeoxynucleotides." *Nat. Rev. Immunol.* 4.4(2004):249-258.

(56) References Cited

OTHER PUBLICATIONS

Kohane. "Microparticles and Nanoparticles for Drug Delivery." *Biotechnol. Bioeng.* 96.2(2007):203-209.
Kondo et al. "A Reaction-Diffusion Wave on the Skin of the Marine Angelfish Pomacanthus." *Nature.* 376(2002):765-768.
Kong et al. "Controlling Degradation of Hydrogels via the Size of Crosslinked Junctions." *Adv. Mater.* 16.21(2004):1917-1921.
Kong et al. "Controlling Rigidity and Degradation of Alginate Hydrogels via Molecular Weight Distribution." *Biomacromolec.* 5.5(2004):1720-1727.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "Designing Alginate Hydrogels to Maintain Viability of Immobilized Cells." *Biomat.* 24.22(2003):4023-4029.
Kong et al. "FRET Measurements of Cell-Traction Forces and Nano-Scale Clustering of Adhesion Ligands Varied by Substrate Stiffness." *PNAS.* 102.12(2005):4300-4305.
Kong et al. "Non-Viral Gene Delivery Regulated by Stiffness of Cell Adhesion Substrates." *Nat. Mater.* 4(2005):460-465.
Kratky et al. "Direct Activation of Antigen-Presenting Cells is Required for CD8+ T-Cell Priming and Tumor Vaccination." *PNAS.* 108.42(2011):17414-17419.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kuwahara et al. "Cell Delivery Using an Injectable and Adhesive Transglutaminase-Gelatin Gel." *Tissue Eng. Part C Methods.* 16.4(2010):609-618.
Kwon et al. "Electrically Erodible Polymer Gel for Controlled Release of Drugs." *Nature.* 354(1991):291-293.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langenkamp et al. "Kinetics of Dendritic Cell Activation: Impact on Priming of TH1, TH2 and Nonpolarized T Cells." *Nat. Immunol.* 1.4(2000):311-316.
Langer et al. "Tissue Engineering." *Science.* 260(1993):920-926.
Lanzavecchia et al. "Regulation of T Cell Immunity by Dendritic Cells." *Cell.* 106.3(2001):263-266.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-λ in Response to Poly IC." *J. Exp. Med.* 207.12(2010):2703-2717.
Leach et al. "Coating of VEGF-Releasing Scaffolds with Bioactive Glass for Angiogenesis and Bone Regeneration." *Biomater.* 27.17(2006):3249-3255.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lee et al. "Hydrogel Formation via Vell Crosslinking." *Adv. Mat.* 15.21(2003):1828-1832.
Lee et al. "Hydrogels for Tissue Engineering." *Chem. Rev.* 101.7(2001):1869-1879.
Lefaucheur et al. "The Cellular Events of Injured Muscle Regeneration Depend on the Nature of the Injury." *Neuromusc. Disorders.* 5.6(1995):501-509.
Lele et al. "Investigating Complexity of Protein-Protein Interactions in Focal Adhesions." *Biochem. Biophys. Res. Commun.* 369.3(2008):929-934.
Lensch et al. "Scientific and Clinical Opportunities for Modeling Blood Disorders With Embyronic Stem Cells." *Blood.* 107.7(2006):2605-2612.
Leor et al. "Cells, Scaffolds, and Molecules for Myocardial Tissue Engineering." *Pharmacol. Therapeutics.* 105(2005):151-163.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Letsinger et al. "Phosphoramidate Analogs of Oligonucleotides." *J. Org. Chem.* 35.11(1970):3800-3803.
Levental et al. "Soft Biological Materials and their Impact on Cell Function." *Soft Matter.* 3(2007):299-306.
Li et al. "A Novel Cyclohexene Derivate, Ethyl ($6R$)-6-[$N$-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Purified Hybrid Cells from Dendritic Cell and Tumor Cell Fusions are Superior Activators of Antitumor Immunity." *Cancer Immunol. Immunother.* 50.9(2001):456-462.
Li. "TNF-α is a Mitogen is Skeletal Muscle." *Am. J. Physiol. Cell Physiol.* 285(2003):C370-C376.
Lin et al. "Transdermal Regulation of Vascular Network Bioengineering Using a Photopolymerizable Methacrylated Gelatin Hydrogel." *Biomater.* 34.28(2013):6785-6796.
Lipton et al. "Developmental Fate of Skeletal Satellite Cells." *Science.* 205(1979):1292-1294.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007):1113-1124.
Liu et al. "Nanostructured Materials Designed for Cell Binding and Transduction." *Biomacromolecules.* 2.2(2001):362-368.
Liu et al. "On the Viscoelastic Character of Liver Tissue: Experiments and Modelling of the Linear Behaviour." *Biorheol.* 37.3(2000):191-201.
Liu. "Dendritic Cell Subsets and Lineages, and Their Functions in Innate and Adaptive Immunity." *Cell.* 106.3(2001):259-262.
Lo et al. "Cell Movement is Guided by the Rigidity of the Substrate." *Biophys. J.* 79.1(2000):144-152.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Lumelsky et al. "Differentiation of Embryonic Stem Cells to Insulin-Secreting Structures Similar to Pancreatic Islets." *Science.* 292.5520(2001):1389-1394.
Lutolf et al. "Repair of Bone Defects Using Synthetic Mimetics of Collagenous Extracellular Matrices." *Nat. Biotechnol.* 21.5(2003):513-518.
López et al. "Magnetic Applications of Polymer Gels." *Macromol. Symp.* 166.1(2001):173-178.

(56) References Cited

OTHER PUBLICATIONS

Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Majeti et al. "Identification of a Hierarchy of Multipotent Hematopoietic Progenitors in Human Cord Blood." *Cell Stem Cell.* 1.6(2007):635-645.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manavski et al. "Vascular Niche Controls Organ Regeneration." *Circ. Res.* 114.17 (2014):1077-1079.
Mansoor et al. "Engineering T Cells for Cancer Therapy." *Br. J. Cancer.* 93.10(2005):1085-1091.
Martinsen et al. "Alginate as Immobilization Material." *Biotech. Bioeng.* 33.1(1989):79-89.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Masedunskas et al. "Role for the Actomyosin Complex in Regulated Exocytosis Revealed by Intravital Microscopy." *PNAS.* 108.33(2011):13552-13557.
Massia et al. "An RGD Spacing of 440 nm is Sufficient for Integrin $\alpha v\beta 3$-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinney-Freeman et al. "Muscle-Derived Hematopoietic Stem Cells are Hematopoietic in Origin." *PNAS.* 99.3(2002):1341-1346.
McKinnon et al. "Biophysically Defined and Cytocompatible Covalently Adaptable Networks as Viscoelastic 3D Cell Culture Systems." *Adv. Mater.* 26.6(2014):865-872.
McPherron et al. "Regulation of Skeletal Muscle Mass in Mice by a New TGF-$\beta$ Superfamily Member." *Nature.* 387(1997):83-90.
McWhorter et al. "Modulation of Macrophage Phenotype by Cell Shape." *PNAS.* 1 10.43(2013):17253-17258.
Meier et al. "Peptide Nucleic Acids (PNAs)—Unusual Properties of Noionic Oligonucleotide Analogues." *Angew. Chem. Int. Ed.* 31.8(1992):1008-1010.
Melero-Martin et al. "Engineering Robust and Functional Vascular Networks In Vivo With Human Adult and Cord Blood-Derived Progenitor Cells." *Circ. Res.* 103.2(2008):194-202.
Melief et al. "Immunotherapy of Established (Pre)Malignant Disease by Synthetic Long Peptide Vaccines." *Nat. Rev. Cancer.* 8(2008):351-360.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Merkel et al. "Using Mechanobiological Mimicry of Red Blood Cells to Extend Circulation Times of Hydrogel Microparticles." *PNAS.* 108.2(2011):586-591.

Metters et al. "Fundamental Studies of Biodegradable Hydrogels as Cartilage Replacement Materials." *Biomed. Sci. Instrum.* 35(1999):33-38.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miljkovic et al. "Chondrogenesis, Bone Morphogenetic Protein-4 and Mesenchymal Stem Cells." *Osteoarthritis Cartilage.* 16(2008):1121-1130.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermines." *J. Med. Chem.* 48(2005):2589-2599.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Miyata et al. "Biomolecule-Sensitive Hydrogels." *Adv. Drug Deliv. Rev.* 54.1(2002):79-98.
Mohan et al. "Novel Porous, Polysaccharide Scaffolds for Tissue Engineering Applications." *Trends Biomater. Artif. Organs.* 18.2(2005):219-224.
Moioli et al. "Matrices and Scaffolds for Drug Delivery in Dental, Oral and Craniofacial Tissue Engineering." *Adv. Drug Deliv. Rev.* 59.4-5(2007):308-324.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Muralidharan-Chari et al. "ARF6-Regulated Shedding of Tumor Cell-Derived Plasma Membrane Microvesicles." *Curr. Biol.* 19.22(2009):1875-1885.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_001561.5, Mar. 16, 2014.
NCBI Accession No. NM_003265, Dec. 30, 2012.
NCBI Accession No. NM_004119, Apr. 14, 2013.
NCBI Accession No. NM_004448.3, Apr. 23, 2014.
NCBI Accession No. NM_005018.2, Apr. 27, 2014.
NCBI Accession No. NM_006274.2, Mar. 31, 2013.
NCBI Accession No. NM_017442, Apr. 14, 2012.
NCBI Accession No. NM_181780.3, Jan. 27, 2014.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_001193, May 3, 2014.

(56) References Cited

OTHER PUBLICATIONS

NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_003367, Jan. 30, 2011.
NCBI Accession No. NP_005009.2, Apr. 27, 2014.
NCBI Accession No. NP_059138, Apr. 14, 2012.
NCBI Accession No. NP_861445.3, Jan. 27, 2014.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Niamlang et al. "Electrically Controlled Release of Salicylic Acid from poly(p-phenylene vinylene) Polyacrylamide Hydrogels." *Int. J. Pharm.* 371(2009):126-133.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The $\alpha6\beta4$ Integrin is a Receptor for Both Lamin and Kalinin." *Exp. Cell Res.* 211.2(1994):360-367.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohashi et al. "Surgical Excision Combined with Autologous Whole Tumor Cell Vaccination is an Effective Therapy for Murine Neuroblastoma." *J. Ped. Surg.* 41(2006):1361-1368.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Orner et al. "Arrays for the Combinatorial Exploration of Cell Adhesion." *J. Am. Chem. Soc.* 126.35(2004):10808-10809.
Osunkoya et al. "Synthesis and Fate of Immunological Surface Receptors on Cultured Burkitt Lymphoma Cells." *Int. J. Cancer.* 4.2(1969):159-165.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ Cell Responses in *Trypanosoma cruzi* Infection." *J. Immunol.* 183(2009):1245-1252.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Palacio et al. "Interleukin 10 and Tumor Necrosis Factor a Gene Expression in Respiratory and Peripheral Muscles." *Arch. Bronconeumol.* 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Partridge et al. "Conversion of mdx Myofibres From Dystrophin-Negative to -Positive by Injection of Normal Myoblasts." *Nature.* 337.6203(1989):176-179.
Pawlaczyk et al. "Age-Dependent Biomechanical Properties of the Skin." *Postepy. Dermatol. Alergol.* 30.5(2013):302-306.
Pedersen et al. "Induction of Regulatory Dendritic Cells by Desamethasone and $1\alpha$,25-Dihydroxyvitamin D3." *Immunol. Lett.* 91(2004):63-69.
Pek et al. "The Effect of Matrix Stiffness on Mesenchymal Stem Cell Differentiation in a 3D Thixotropic Gel." *Biomater.* 31.3(2010):385-391.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Pena et al. "Effects of TGF-$\beta$ and TGF-$\beta$ Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peters et al. "Engineering Vascular Networks in Porous Polymer Matrices." *J. Biomed. Mater. Res.* 60.4(2002):668-678.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Phillippi. "Patterning of Multiple Cell Lineages from a Single Stem Cell Population." *Annual Meeting of the American Society for Cell Biology.* (Dec. 10, 2006).
Pinho et al. "PDGFR$\alpha$ and CD51 Mark Human Nestin+ Sphere-Forming Mesenchymal Stem Cells Capable of Hematopoietic Progenitor Cell Expansion." *J. Exp. Med.* 210.7(2013):1351-1367.
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Porter et al. "Separation of Natural Populations of Coliform Bacteria from Freshwater and Sewage by Magnetic-Bead Cell Sorting." *J. Microbiol. Meth.* 33.3(1998):221-226.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.

(56) References Cited

OTHER PUBLICATIONS

Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Qui et al. "Environment-Sensitive Hydrogels for Drug Delivery." *Adv. Drug Deliv. Rev.* 53.3(2001):321-339.
Raeber et al. "Molecularly Engineered Peg Hydrogels: A Novel Model System for Proteolyrically Mediated Cell Migration." *Biophys. J.* 89.2(2005):1374-1388.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Randolph et al. "Migration of Dendritic Cell Subsets and Their Precursors." *Annu. Rev. Immunol.* 26(2008):293-316.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.* 10(1998):366. (Abstract #153.07).
Reis e Sousa. "Activation of Dendritic Cells: Translating Innate into Adaptive Immunity." *Curr. Opin. Immunol.* 16.1(3005):21-25.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.* 15.12(2004):1561-1570.
Ridgway et al. "Inhibition of DII4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rizzo et al. "An Improved Cyan Fluorescent Protein Variant Useful for FRET." *Nat. Biotechnol.* 22.4(2004):445-449.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal "Self" Peptides that Inhibit Phagocytic Clearance and Enhance Delivery of Nanoparticles." *Science.* 339.6122(2013):971-975.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Salem et al. "Defining the Antigen-Specific T-Cell Response to Vaccination and Poly(I:C)/TLR3 Signaling." *J. Immunother.* 28.3(2005):220-228.
Salvador et al. "Combination of Immune Stimulating Adjuvants With Poly(lactide-co-glycolide) Microspheres Enhances the Immune Response of Vaccines." *Vaccine.* 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Scheel et al. "Toll-Like Receptor-Dependent Activation of Several Human Blood Cell Types by Protamine Condensed mRNA." *Eur. J. Immunol.* 35(2005):1557-1566.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schofield. "The Relationship Between the Spleen Colony-Forming Cell and the Haemopoietic Stem Cell." *Blood. Cells.* 4.1-2(1978):7-25.
Schuler et al. "The Use of Dendritic Cells in Cancer Immunotherapy." *Curr. Opin. Immunol.* 15.2(2003):138-147.
Schwartz. "Integrins and Extracellular Matrix in Mechanotransduction." *Cold Spring Harb. Perspect. Biol.* 2.12(2010):a005066.
Seale et al. "Pax7 Is Required for the Specification of Myogenic Satellite Cells." *Cell.* 102.6(2000):777-786.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.

(56) References Cited

OTHER PUBLICATIONS

Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Shoichet et al. "Stability of Hydrogels Used in Cell Encapsulation: An In Vitro Comparison of Alginate and Agarose." *Biotechnol. Bioeng.* 50(1996):374-381.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Siegwart et al. "Synthesis, Characterization, and in vitro Cell Culture Viability of Degradable Poly(*N*-isopropylacrylamide-*co*-5,6-benzo-2-methylene-1,3-dioxepane)-Based Polymers and Crosslinked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Silva et al. "Material-Based Deployment Enhances Efficacy of Endothelial Progenitor Cells." *PNAS.* 105.38(2008):14347-14352.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Singer et al. "Cutaneous Wound Healing." *N. Engl. J. Med.* 341.10(1999):738-746.
Skokos et al. "CD8– DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Sun et al. "Sustained Vascular Endothelial Growth Factor Delivery Enhances Angiogenesis and Perfusion in Ischemic Hind Limb." *Pharm. Res.* 22.7(2005):1110-1116.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Takahashi et al. "Induction of Pluripotent Stem Cells from Adult Human Fibroblasts by Defined Factors." *Cell.* 131.5(2007):861-872.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tanaka et al. "Collapse of Gels in an Electric Field." *Science.* 218(1982):467-469.
Tannous. "*Gaussia* Luciferase Reporter Assay for Monitoring Biological Processes in Culture and in vivo." *Nat. Protoc.* 4.4(2009):582-591.
Tatsumi et al. "HGF/SF Is Present in Normal Adult Skeletal Muscle and is Capable of Activating Satellite Cells." *Dev. Biol.* 194.1(1998):114-128.
ten Dijke et al. "Growth Factors for Wound Healing." *Nat. Biotechnol.* 7(1989):793-798.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Thurston et al. "The Delta Paradox: DLL4 Blockade Leads to More Tumour Vessels but Less Tumour Growth." *Nat. Rev. Cancer.* 7.5(2007):327-331.
Tidball. "Inflammatory Cell Response to Acute Muscle Injury." *Med. Sci. Sports Exerc.* 27.7(1995):1022-1032.
Tomer et al. "Electrically Controlled Release of Macromolecules from Cross-Linked Hyaluronic Acid Hydrogels." *J. Control. Release.* 33.3(1995):405-413.
Tong et al. "Engineering Interpenetrating Network Hydrogels as Biomimetic Cell Niche with Independently Tunable Biochemical and Mechanical Properties." *Biomater.* 35.6(2014):1807-1815.
Tourniaire et al. "Polymer Microarrays for Cellular Adhesion." *Chem. Commun.* 20(2006):2118-2120.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Tsien. "The Green Fluorescent Protein." *Annu. Rev. Biochem.* 67(1998):509-544.
Turing. "Discussion: Turing's Theory of Morphogenesis—It's Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.

(56) References Cited

OTHER PUBLICATIONS

Uchida et al. "Immunization by Particle Bombardment of Antigen-Loaded poly-(DL-lactide-coglycolide) Microspheres in Mice." *Vaccine.* 12(2006):2120-2130.
Ugarte et al. "Notch Signaling Enhances Osteogenic Differentiation While Inhibiting Adipogenesis in Primary Human Bone Marrow Stromal Cells." *Exp. Hematol.* 37(2009):867-875.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al. "Stem Cell Niches in the Adult Mouse Heart." *PNAS.* 103.24(2006):9226-9231.
van der Bruggen et al. "T Cell-Defined Tumor Antigens." *Cancer Immunity.* (2013). Http:www.cancerimmunity.org/peptide.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Venturoni et al. "Investigations into the Polymorphism of Rat Tail Tendon Fibrils Using Atomic Force Microscopy." *Biochem. Biophys. Res. Commun.* 303.2(2003):508-513.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.

Wang et al. "Biological Activity of Bevacizumab, a Humanized Anti-VEGF Antibody in vitro." *Angiogenesis.* 7.4(2004):335-345.
Wang et al. "Evolution of New Nonantibody Proteins via Iterative Somatic Hypermutation." *PNAS.* 101.48(2004):16745-16749.
Wang et al. "Mechanotransduction at a Distance: Mechanically Coupling the Extracellular Matric with the Nucleus." *Nat. Rev. Mol. Cell. Biol.* 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs.* 31.3(2013):707-713.
Warner et al. "Cyclooxygenases: New Forms, New Inhibitors, and Lessons from the Clinic." *FASEB J.* 18.7(2004):790-804.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res.* 30(1963):331-338.
Wen et al. "Mechanically Robust Gelatin-Alginate IPN Hydrogels by a Combination of Enzymatic and Ionic Crosslinking Approaches." *Macromol. Mater. Eng.* 299(2013):504-513.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):148-152.
Wong et al. "Mechanical Force Prolongs Acute Inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wozniak et al. "Mechanotransduction in Development: A Growing Role for Contractility." *Nat. Rev. Mol. Cell Biol.* 10.1(2009):34-43.
Wright et al. "Muscle-Based Gene Therapy and Tissue Engineering for the Musculoskeletal System." *Drug Disc. Today.* 6.14(2001):728-733.
Xie et al. "Preparation and Application of Surface-Coated Superparamagnetic Nanobeads in the Isolation of Genomic DNA." *J. Magn. Magnetic Mater.* 277.1(2004):16-23.
Yancopoulos et al. "Vascular-Specific Growth Factors and Blood Vessel Formation." *Nature.* 407.6801(2000):242-248.
Yeung et al. "Effects of Substrate Stiffness on Cell Morphology, Cytoskeletal Structure, and Adhesion." *Cell Motil. Cytoskeleton.* 60.1(2005):24-34.
Yoo et al. "Bio-Inspired, Bioengineered and Biomimetic Drug Delivery Carriers." *Nat. Rev. Drug Discov.* 10.7(2011):521-535.
Yoon. "Hidden Markov Models and their Applications in Biological Sequene Analysis." *Curr. Genomics.* 10.6(2009):402-415.
Young et al. "Gelatin as a Delivery Vehicle for the Controlled Release of Bioactive Molecules." *J. Control. Release.* 109.1-3(2005):256-274.
Yu et al. "Induced Pluripotent Stem Cell Lines Derived from Human Somatic Cells." *Science.* 318.5858(2007):1917-1920.
Yuen et al. "Mimicking Nature by Codelivery of Stimulant and Inhibitor to Create Temporally Stable and Spatially Restricted Angiogenic Zones." *PNAS.* 107.42(2010):17933-17938.

(56) References Cited

OTHER PUBLICATIONS

Yuk et al. "Electric Current-Sensitive Drug Delivery System Using Sodium Alginate/Polyacrylic Acid Composites." *Pharm. Res.* 9.7(1992):955-957.

Zammit et al. "Kinetics of Myoblast Proliferation Show That Resident Satellite Cells are Competent to Fully Regenerate Skeletal Muscle Fibers." *Exp. Cell Res.* 281.1(2002):39-49.

Zammit et al. "Muscle Satellite Cells Adopt Divergent Fates: A Mechanism for Self-Renewal?" *J. Cell Biol.* 166.3(2004):347-357.

Zeltinger et al. "Effect of Pore Size and Void Fraction on Cellular Adhesion, Proliferation, and Matrix Deposition." *Tissue Eng.* 7.5(2001):557-572.

Zemel et al. "Optimal Matrix Rigidity for Stress Fibre Polarization in Stem Cells." *Nat. Phys.* 6.6(2010):468-473.

Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.

Zhang et al. "A Tension-Induced Mechanostransduction Pathway Promotes Epithelial Morphogenesis." *Nature.* 471.7336(2011):99-103.

Zhang et al. "Talin Depletion Reveals Independence of Initial Cell Spreading from Integrin Activation and Traction." *Nat. Cell Biol.* 10.9(2008):1062-1068.

Zhao et al. "Active Scaffolds for On-Demand Drug and Cell Delivery." *PNAS.* 108.1(2011):67-72.

Zhao et al. "Stress-Relaxation Behavior in Gels with Ionic and Covalent Crosslinks." *J. Appl. Phys.* 107.6(2010):63509.

Zhou et al. "Microstructure and Mechanical Properties of Poly(L-lactide) Scaffolds Fabricated by Gelatin Particle Leaching Method." *J. Appl. Polymer Sci.* 98(2005):1373-1379.

Yang, Fan et al., "The effect of incorporating RGD adhesive peptide in polyethylene glycol diacrylate hydrogel on osteogenesis of bone marrow stromal cells," *Biomaterials*, vol. 26(2005):5991-5998.

\* cited by examiner

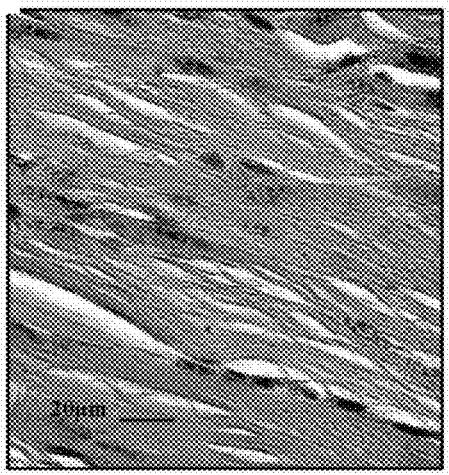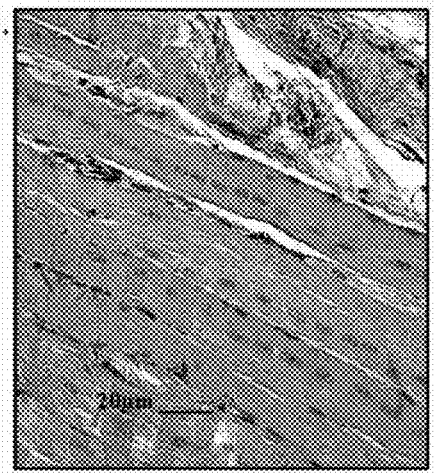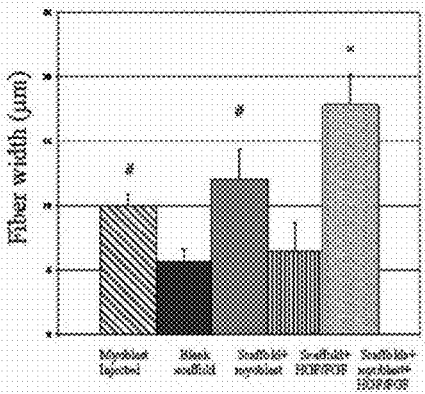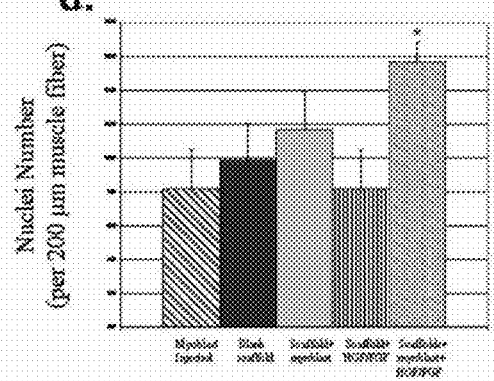
FIG. 10

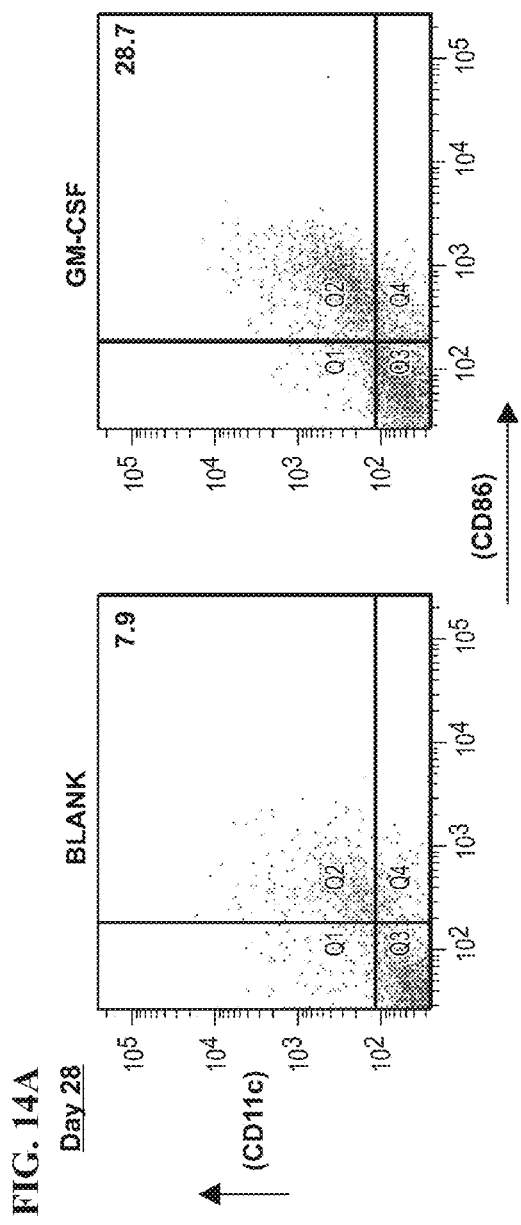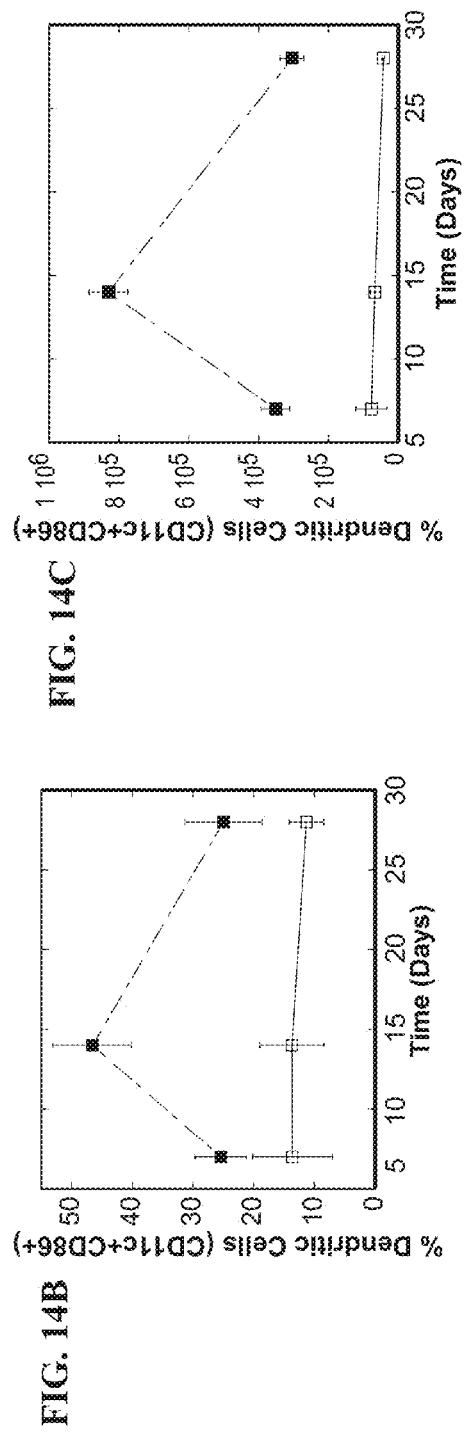

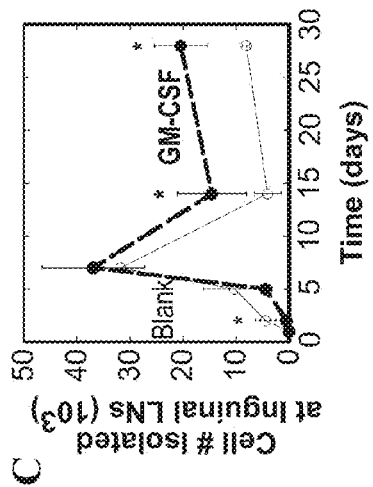
FIG. 16A
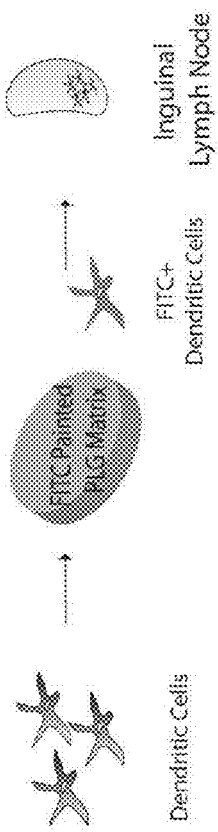
FIG. 16C
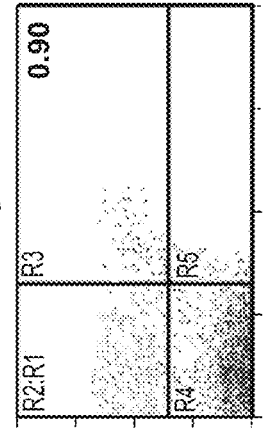
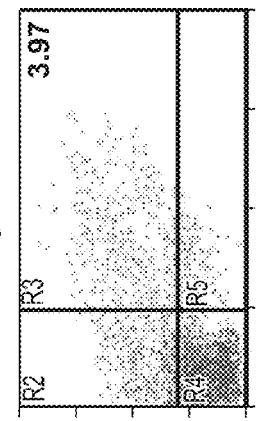
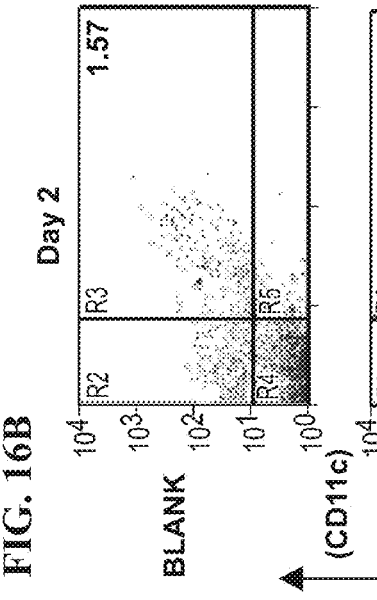
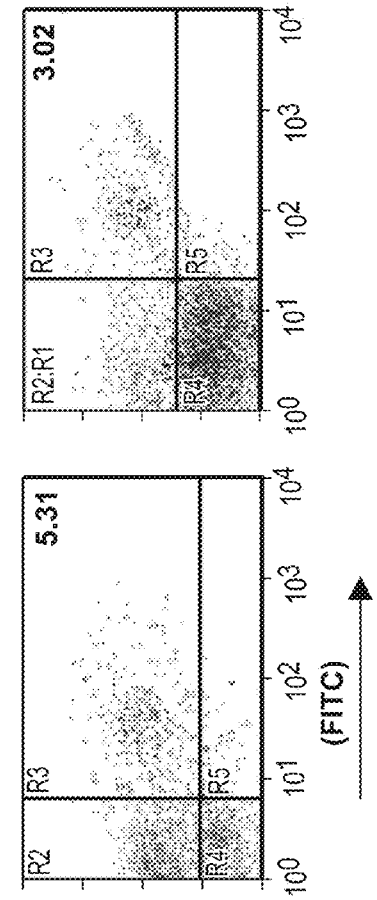
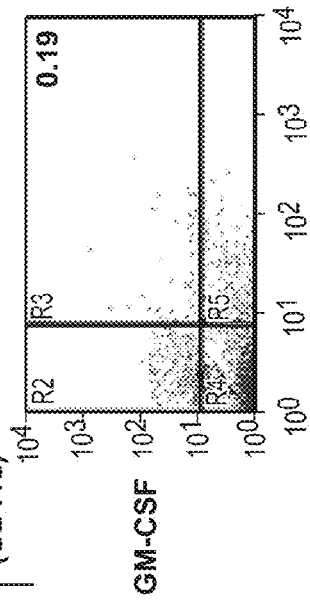
FIG. 16B

SCAFFOLDS FOR CELL TRANSPLANTATION

RELATED APPLICATIONS

This application is a continuation of U.S. application Ser. No. 13/305,088, filed Nov. 28, 2011, which is a continuation of U.S. application Ser. No. 11/638,796, filed Dec. 13, 2006, now U.S. Pat. No. 8,067,237, which claims the benefit of priority under 35 U.S.C. §119(e) to U.S. Provisional Application No. 60/749,998, filed Dec. 13, 2005 and to U.S. Provisional Application No. 60/814,134, filed Jun. 16, 2006, each of which are incorporated herein by reference in their entireties.

GOVERNMENT SUPPORT

The invention was supported, in whole, or in part, by NIH/NICDR grant number RO1 DE13349 and HL069957. The Government has certain rights in the invention.

BACKGROUND OF THE INVENTION

The total costs of musculoskeletal disease in the US in 2000 have been estimated at US $254 billion and, in developing countries, the figure is estimated at US$100 billion. Under normal conditions, muscles can repair themselves by regenerating damaged muscle fibers and restoring muscle strength. Following an initial necrosis of damaged muscle fibers, an inflammatory response is initiated that activates a resident population of quiescent cells termed satellite cells. These myogenic cells proliferate, migrate to the site of injury, differentiate and fuse to form mature myofibers, or fuse with existing myofibers thus regenerating damaged muscle fibers and restoring their function. When these normal processes are compromised by disease or age, damaged muscle fibers are instead replaced by infiltrating fibrous tissue or fat, leading to a net loss of muscle mass and a resultant loss of strength.

Cell transplantation has been used in regenerative medicine for musculoskeletal disorders as well as degenerative conditions such as diabetes with limited success. Limitations of earlier approaches include loss of cell viability and function following transplantation.

SUMMARY OF THE INVENTION

The devices and methods of the invention provide a solution to several problems associated with previous cell transplantation protocols. Transplantation systems that enhance the viability of the cells and induce their outward migration to populate injured or defective bodily tissues enhance the success of tissue regeneration, e.g., the regeneration of muscle tissue or other tissues as well as angiogenesis. Such a device that controls cell function and/or behavior, e.g., locomotion, contains a scaffold composition and one or more bioactive compositions. The bioactive composition is incorporated into or coated onto the scaffold composition. The scaffold composition and/or bioactive composition temporally and spatially (directionally) controls egress of a resident cell or progeny thereof.

The devices mediate active recruitment, modification, and release of host cells from the material in vivo, thereby improving the function of cells that have resided in the scaffold. For example, the device attracts or recruits cells already resident in the body to the scaffold material, and programs or reprograms the resident cells to a desired fate (e.g., immune activation or tissue regeneration).

This device includes a scaffold composition which incorporates or is coated with a bioactive composition; the device regulates the egress of resident cells. Egress is regulated spatially and temporally. Depending on the application for which the device is designed, the device regulates egress through the physical or chemical characteristics of the scaffold itself. For example, the scaffold composition is differentially permeable, allowing cell egress only in certain physical areas of the scaffold. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or rehydration, oxygenation, chemical or pH alteration, or ongoing self-assembly of the scaffold composition. These processes are driven by diffusion or cell-secretion of enzymes or other reactive chemicals.

Alternatively or in addition, egress is regulated by a bioactive composition. By varying the concentration of growth factors, homing/migration factors, morphogens, differentiation factors, oligonucleotides, hormones, neurotransmitters, neurotransmitter or growth factor receptors, interferons, interleukins, chemokines, cytokines, colony stimulating factors, chemotactic factors, extracellular matrix components, adhesion molecules and other bioactive compounds in different areas of the device. The device controls and directs the migration of cells through its structure. Chemical affinities are used to channel cells towards a specific area of egress. For example, adhesion molecules are used to attract or retard the migration of cells. By varying the density and mixture of those bioactive substances, the device controls the timing of the migration and egress. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold also regulates the diffusion of bioactive agents through the device.

The bioactive composition includes one or more compounds that regulate cell function and/or behavior. The bioactive composition is covalently linked to the scaffold composition or non-covalently associated with the scaffold. For example, the bioactive composition is an extracellular matrix (ECM) component that is chemically crosslinked to the scaffold composition. Regardless of the tissue of origin, ECM components generally include three general classes of macromolecules: collagens, proteoglycans/glycosaminoglycans (PG/GAG), and glycoproteins, e.g., fibronectin (FN), laminin, and thrombospondin. ECM components associate with molecules on the cell surface and mediate adhesion and/or motility. Preferably, the ECM component associated with the scaffold is a proteoglycan attachment peptide or cyclic peptide containing the amino acid sequence arginine-glycine-aspartic acid (RGD). Proteoglycan attachment peptides are selected from the group consisting of $G_4RGDSP$ (SEQ ID NO: 1), XBBXBX (SEQ ID NO: 2), PRRARV (SEQ ID NO: 3), YEKPGSPPREVVPRPRPGV (SEQ ID NO:4), RPSLAKKQRFRHRNRKGYRSQRGHSRGR (SEQ ID NO: 5), and RIQNLLKITNLRIKFVK (SEQ ID NO: 6), and cell attachment peptides are selected from the group consisting of RGD, RGDS, LDV, REDV, RGDV, LRGDN (SEQ ID NO: 7), IKVAV (SEQ ID NO: 8), YIGSR (SEQ ID NO: 9), PDSGR (SEQ ID NO: 10), RNIAEIIKDA (SEQ ID NO: 11), RGDT, DGEA, and VTXG.

Components of the ECM, e.g., FN, laminin, and collagen, interact with the cell surface via the integrin family of receptors, a group of divalent cation-dependent cell surface glycoproteins that mediate cellular recognition and adhesion to components of the ECM and to other cells. Ligands recognized by integrins typically contain an RGD amino acid sequence that is expressed in many ECM proteins. Exemplary molecules that mediate cell adhesion and/or movement include FN, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, cell adhesion molecules including connexins, selectinsinclude collagen, RGD (Arg-Gly-Asp) and YIGSR (Tyr-Ile-Gly-Ser-Arg) peptides, glycosaminoglycans (GAGs), hyaluronic acid (HA), integrins, selectins, cadherins and members of the immunoglobulin superfamily. Carbohydrate ligands of the ECM include the polysaccharides hyaluronic acid, and chondroitin-6-sulfate.

Signal transduction events that participate in the process of cell motility are initiated in response to cell growth and/or cell differentiation factors. Thus, the device optionally contains a second bioactive composition that is a growth factor, morphogen, differentiation factor, or chemoattractant. For example, the device includes vascular endothelial growth factor (VEGF), hepatocyte growth factor (HGF), or fibroblast growth factor 2 (FGF2) or a combination thereof. Other factors include hormones, neurotransmitters, neurotransmitter or growth factor receptors, interferons, interleukins, chemokines, MMP-sensitive substrate, cytokines, colony stimulating factors. Growth factors used to promote angiogenesis, bone regeneration, wound healing, and other aspects of tissue regeneration are listed herein and are used alone or in combination to induce colonization or regeneration of bodily tissues by cells that have migrated out of an implanted scaffold device.

Alternatively, the second bioactive composition is an inhibitor of differentiation. In this case, the cells are maintained at a desired stage of development or differentiation by the inhibitor until the inhibitor is depleted (e.g., has diffused out of the scaffold or is rendered inactive) or until another signal is provided to induce a change, e.g., to promote maturation or differentiation.

In some cases, the second bioactive composition is covalently linked to the scaffold composition, keeping the composition relatively immobilized in or on the scaffold composition. In other cases, the second bioactive composition is noncovalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, it aromatic, and hydrophobic. For example, a growth factor such as VEGF is associated with the device by noncovalent bonds and exits the device following administration of the cell-seeded device to a target site to further promote angiogenesis and tissue repair of the target bodily tissue.

The scaffold composition is biocompatible. The composition is bio-degradable/erodable or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

In one example, cells mediate degradation of the scaffold matrix, i.e., the scaffold composition is enzymatically digested by a composition elicited by a resident cell, and the egress of the cell is dependent upon the rate of enzymatic digestion of the scaffold. In this case, polymer main chains or cross-links contain compositions, e.g., oligopeptides, that are substrates for collagenase or plasmin, or other enzymes produced by within or adjacent to the scaffold.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. One preferred scaffold composition includes an RGD-modified alginate.

Porosity of the scaffold composition influences egress of the cells from the device. Pores are nanoporous, microporous, or macroporous. For example, the diameter of nanopores are less than about 10 nm; micropore are in the range of about 100 nm-20 µm in diameter; and, macropores are greater than about 20 µm (preferably greater than about 100 µm and even more preferably greater than about 400 µm). In one example, the scaffold is macroporous with aligned pores of about 400-500 µm in diameter.

The devices are manufactured in their entirety in the absence of cells or can be assembled around or in contact with cells (the material is gelled or assembled around cells in vitro or in vivo in the presence of cells and tissues) and then contacted with cells to produce a cell-seeded structure. Alternatively, the device is manufactured in two or more (3, 4, 5, 6, ... 10 or more) stages in which one layer or compartment is made and seeded with cells followed by the construction of a second, third, fourth or more layers, which are in turn seeded with cells in sequence. Each layer or compartment is identical to the others or distinguished from one another by the number, genotype, or phenotype of the seed cell population as well as distinct chemical, physical and biological properties. Prior to implantation, the device is contacted with purified populations cells or characterized mixtures of cells as described above. Exemplary cells include myoblasts for muscle regeneration, repair or replacement; hepatocytes for liver tissue regeneration, repair or organ transplantation, chondrocytes for cartilage replacement, regeneration or repair, and osteoblasts for bone regeneration, replacement or repair, various stem cell populations (embryonic stem cells differentiated into various cell types), bone marrow or adipose tissue derived adult stem cells, cardiac stem cells, pancreatic stem cells, endothelial progenitors and outgrowth endothelial cells, mesenchymal stem cells, hematopoietic stem cells, neural stem cells, satellite cells, side population cells, differentiated cell populations including osteoprogenitors and osteoblasts, chondrocytes, keratinocytes for skin, tenocytes for tendon, intestinal epithelial cells, endothelial cells, smooth muscle cells and fibroblasts for tissue or organ regeneration, repair or replacement and/or for DNA delivery. Preferably, the cells are human; however, the system is adaptable to other eucaryotic animal cells, e.g., canine, feline, equine, bovine, and porcine as well as prokaryotic cells such as bacterial cells.

A method of making a scaffold is carried out by providing a scaffold composition and covalently linking or noncovalently associating the scaffold composition with a first bioactive composition. The first bioactive composition preferably contains a cell adhesion ligand. The scaffold composition is also contacted with a second bioactive composition. The second bioactive composition is preferably non-covalently associated with the scaffold composition to yield a doped scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components to one another and/or insertion of semi-permeable, permeable, or nonpermeable membranes within or at one or more boundaries of the device to further control/regulate locomotion of cells or bioactive compositions. As described above, the scaffold is seeded with cells after completion of the construction of the device or in an iterative manner throughout the construction of each component.

Therapeutic applications of the device include tissue generation, regeneration/repair, as well as augmentation of function of a mammalian bodily tissue, and the targeted destruction of undesired tissues (e.g., cancer, undesired adipose depots), as well as the instruction of immune cells. For example, the method includes the steps of providing a device that includes scaffold composition with a bioactive composition incorporated therein or thereon and a mammalian cell bound to the scaffold. A mammalian tissue is contacted with the device. The scaffold composition temporally controls egress of the cell and the bioactive composition spatially or directionally regulates egress of the cell. In another example, the device that is provided contains a scaffold composition with a bioactive composition incorporated therein or thereon and a mammalian cell immobilized within the scaffold. In the latter case, the cell remains immobilized within the scaffold, and the scaffold composition temporally controls egress of a progeny cell of the immobilized cell and the bioactive composition spatially regulates egress of the progeny cells.

A method of modulating an activity of a cell, e.g., a host cell, is carried out by administering to a mammal a device containing a scaffold composition and a recruitment composition incorporated therein or thereon, and then contacting the cell with a deployment signal. The deployment signal induces egress of the cells from the device. The activity of the cell at egress differs from that prior to entering the device. Cells are recruited into the device and remain resident in the device for a period of time, e.g., minutes; 0.2. 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to a change in the activity or level of activity of the cells. The cells are contacted with or exposed to a deployment signal that induces induces egress of the altered (re-educated or reprogrammed) cells and the cells migrate out of the device and into surrounding tissues or remote target locations.

The deployment signal is a composition such as protein, peptide, or nucleic acid. For example, cells migrating into the device only encounter the deployment signal once they have entered the device. In some cases, the deployment signal is a nucleic acid molecule, e.g., a plasmid containing sequence encoding a protein that induces migration of the cell out of the device and into surrounding tissues. The deployment signal occurs when the cell encounters the plasmid in the device, the DNA becomes internalized in the cell (i.e., the cell is transfected), and the cell manufactures the gene product encoded by the DNA. In some cases, the molecule that signals deployment is an element of the device and is released from the device in delayed manner (e.g., temporally or spatially) relative to exposure of the cell to the recruitment composition. Alternatively, the deployment signal is a reduction in or absence of the recruitment composition. For example, a recruitment composition induces migration of cells into the device, and a reduction in the concentration or depletion, dissipation, or diffusion of the recruitment composition from the device results in egress of cells out of the device. In this manner, immune cells such as T cells, B cells, or dendritic cells (DCs) of an individual are recruited into the device, primed and activated to mount an immune response against an antigen-specific target. Optionally, an antigen corresponding to a target to which an immune response is desired is incorporated into or onto the scaffold structure. Cytokines, such as granulocyte macrophage colony stimulating factor (GM-CSF) are also a component of the device to amplify immune activation and/or induce migration of the primed cells to lymph nodes. Other cell specific recruitment compositions are described below. For example, vascular endothelial growth factor (VEGF) is useful to recruit angiogenic cells.

The device recruit cells in vivo, modifies these cells, and then promotes their migration to another site in the body. This approach is exampled herein in the context of dendritic cells and cancer vaccine development but is also useful to other vaccines such as those against microbial pathogens as well as cell therapies in general. Cells educated using the devices described herein promote regeneration of a tissue or organ immediately adjacent to the material, or at some distant site. Alternatively, the cells are educated to promote destruction of a tissue (locally or at a distant site). The methods are also useful for disease prevention, e.g., to promote cell-based maintenance of tissue structure and function to stop or retard disease progression or age-related tissue changes. The education of cells within the device, "programming" and "reprogramming" permits modification of the function or activity of any cell in the body to become a multipotent stem cell again and exert therapeutic effects.

Other features and advantages of the invention will be apparent from the following description of the preferred embodiments thereof, and from the claims. All references cited herein are incorporated by reference.

BRIEF DESCRIPTION OF THE DRAWINGS

FIG. 1A shows an initial isolation resulted in heterogeneous cell population with myogenic cells (arrows) staining for both desmin and Hoescht nuclear stain. In contrast non-myogenic cells are only stained with the nuclear dye (arrow heads). FIG. 1B shows that Percoll fractionation resulted in homogeneous myogenic cultures.

FIGS. 10A-B are photomicrographs showing that the width of regenerating fibers and number of centrally located nuclei at 30 days were significantly greater in muscles treated with scaffolds delivering cells and growth factors (FIG. 10B), as compared to scaffolds delivering only growth factors (FIG. 10A) or any of the other conditions. FIG. 10C is a bar graph drawing quantification of fiber width, and FIG. 10D is a bar graph showing the number of centrally located nuclei per fiber length. Fiber width was increased with myoblast injection or treatment with scaffolds releasing HGF and FGF2 (# indicates p<0.01 compared to blank scaffolds or scaffolds transplanting cells without growth factors), and was most dramatically increased by treatment with scaffolds delivering myoblasts and growth factors (* indicates p<0.001 compared to all other conditions). Increased centrally located nuclei per muscle length was observed only when scaffolds containing myoblasts and HGF/FGF2 were used to treat muscle injury. Values represent mean and standard deviation (n=6).

FIG. 13 D is a bar graph showing recovery of blood perfusion. Hindlimbs subjected to surgery were visually examined, and grouped as normal (displaying no discrepancy in color or limb integrity as compared to non-ischemic hindlimbs of the same animal), or presenting one necrotic toe, multiple necrotic toes, or a complete necrotic foot.

FIG. 14A is a scatter plot and FIGS. 14B-C are line graphs showing that GM-CSF delivery from PLG scaffolds enhances the in vivo recruitment and expansion of DCs. FIG. 14A shows FACS plots of cells positive for the DC markers, CD86 and CD11c, after isolation from GM-CSF loaded scaffolds and blank scaffolds. FIG. 14B shows the percentage of DCs isolated from GM-CSF loaded scaffolds (-■-) and blank scaffolds (-□-). FIG. 14C shows the total number of DCs isolated from GM-CSF loaded scaffolds (-■-) and blank scaffolds (-□-). GM-CSF scaffolds were loaded with 3 µg of the recombinant protein.

FIG. 15A shows the percentage of CD11c+CD86+ dendritic cells isolated from PLG scaffolds in response to delivery of 1, 3 and 7 µg of GM-CSF (n=4), and FIG. 15B shows the cellular density of CD11c+CD86+ dendritic cells normalized by the control. Scaffolds were explanted from subcutaneous pockets at Day 14.

FIG. 16A is a schematic diagram of an in vivo DC tracking assay. DCs are recruited to FITC painted PLG matrices, implanted subcutaneously into the backs of C57B6 mice, where they pick up FITC molecules and emigrate to the lymph nodes (LN) as FITC+DCs. Local GM-CSF delivery from fluoroscein (FITC) painted PLG matrices allows for the sustained transport of matrix derived DCs to the draining lymph nodes for extended periods. FIG. 16B is a series of scatter plots showing representative FACS data of CD11c+ FITC+DCs in the inguinal lymph nodes at 2, 7 and 14 days after the implantation of Blank and GM-CSF loaded PLG matrices. FIG. 16C is a line graph showing the total number of FITC+DCs in the inguinal lymph nodes of C57B6 mice at days 2, 4, 7, 14 and 28 days after the implantation of blank and GM-CSF loaded scaffolds.

DETAILED DESCRIPTION OF THE INVENTION

Figure 1:
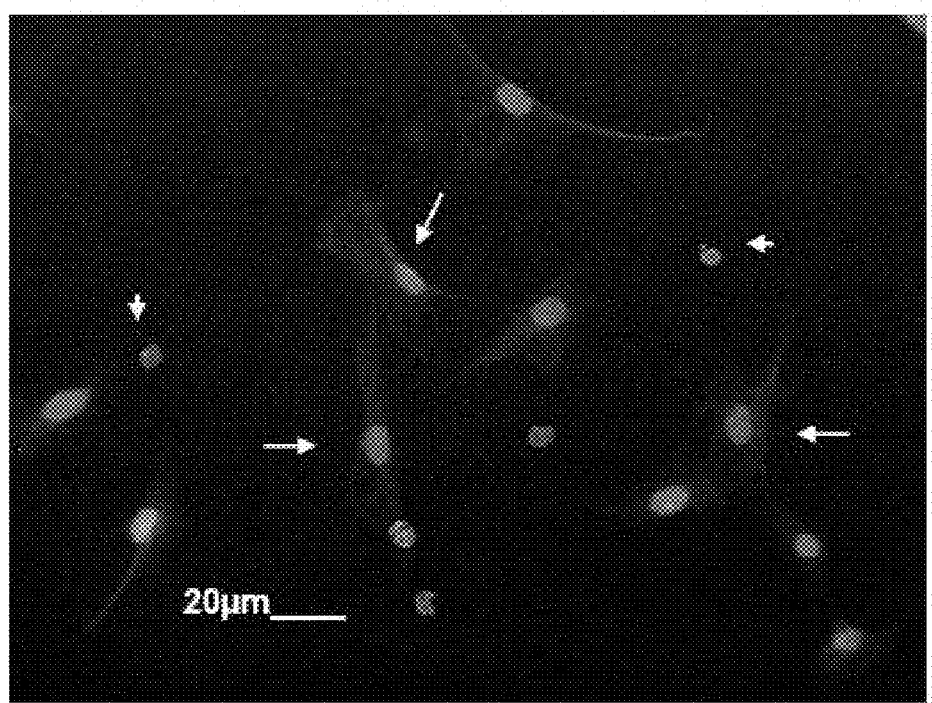
FIGS. 1A and 1B are photomicrographs showing that the purity of primary skeletal muscle myoblast cultures is increased by Percoll fractionation.
Figure 1:
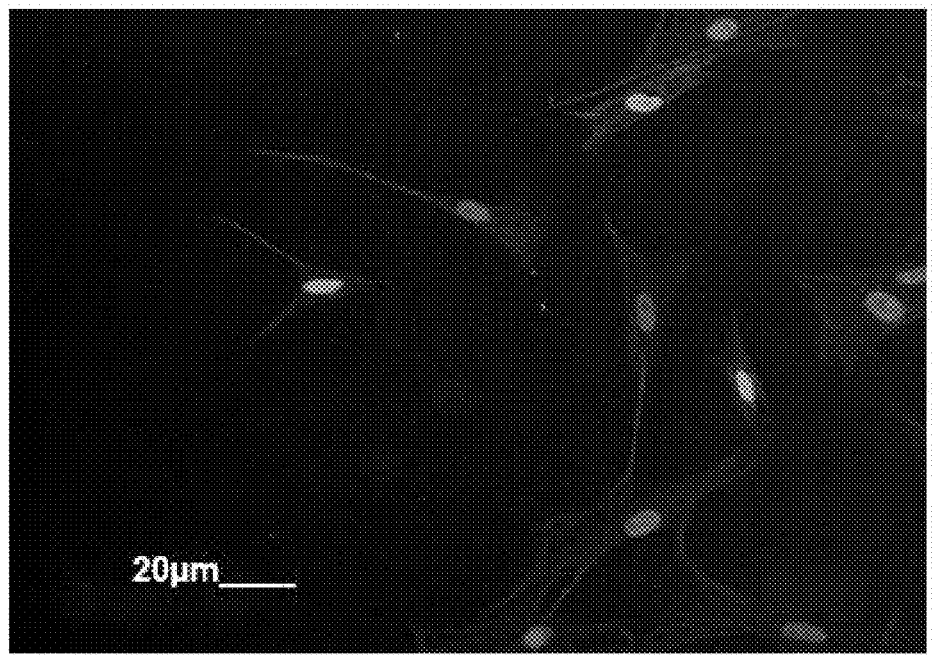

Regenerative medical technologies are devices and methods that repair or replace diseased or defective tissues or organs. Tissue engineering is the application of the principles and methods of engineering and the life sciences to the development of biological substitutes to restore, maintain or improve function of bodily structures and tissues, or to selectively promote the destruction of undesired tissues. It involves the development of methods to build biological substitutes as supplements or alternatives to whole organ or tissue transplantation, or the development of strategies to manipulate tissues in vivo. The use of living cells and/or extracellular matrix (ECM) components in the development of implantable parts or devices is an attractive approach to restore or to replace function. The methods and devices are useful to generate functional biological structure de novo or to regenerate organs in situ, as well as to restore or supplement tissue function. The devices are placed into or adjacent to a particular diseased or injured tissue in the body or broadly dispersed throughout a tissue in the body. The device makes direct contact with the tissue to be treated or contains cells that migrate to nearby or remote tissue targets following residence in the device.

Cell Populations

Scaffold structures are seeded with one or more populations of purified or isolated cells. The term "isolated" used in reference to a cell type, e.g., a stem cell means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS). Optionally, the device is seeded with two or more substantially pure populations of cells. The populations are spatially or physically separated, e.g., one population is encapsulated, or the cells are allowed to come into with one another. The scaffold or structural support not only provides a surface upon which cells are seeded/attached but indirectly affects production/education of cell populations by housing a second (third, or several) cell population(s) with which a first population of cells associates (cell-cell adhesion). Such "accessory" cell populations secrete desirable cytokines, growth factors or other signaling molecules, and/or deposit appropriate extracellular matrix proteins. Cytokines are small secreted proteins which mediate and regulate immunity, inflammation, and hematopoiesis. Cytokines can act over short distances and short time spans and at very low concentration. They act by binding to specific membrane receptors, which then signal cells via second messengers, often tyrosine kinases, to alter its behavior (e.g., cell function and/or gene expression). Responses to cytokines include increasing or decreasing expression of membrane proteins (including cytokine receptors), proliferation, and secretion of effector molecules. Such molecules are also referred to as lymphokines (cytokines made by lymphocytes), monokines (cytokines made by monocytes), chemokines (cytokines with chemotactic activities), and interleukins (cytokines made by one leukocyte and acting on other leukocytes). Cytokines act on the cells that secrete them (autocrine action), on nearby cells (paracrine action), or on distant cells (endocrine action).

A stem cell is an undifferentiated cell that differentiates into a mature functional tissue specific cell upon contact with appropriate microenvironment, e.g., growth factors and other differentiating agents. The devices/scaffold described herein represent such a microenvironment. Each device constitutes a factory that attracts/accepts, reproduces, sustains, educates, and sends forth to surrounding bodily tissues tissue-specific cells that are capable of colonizing and regenerating damaged tissue. In addition to stem cells, the scaffolds house progenitor cells, differentiated cells, support cells, modified cells (e.g., genetically modified (e.g., by DNA delivery (by plasmid or virus), or by siRNA, µRNA) to produce exogenous proteins or chemically modified with drugs to enhance or suppress specific signaling pathways (e.g., protein kinases) or genetic regulatory pathways (e.g., upregulate or downregulate activity of master transcription factors) that are involved in a variety of cell fate decisions, or surface modified with ligands or growth factors and morphogens, or small molecule mimics of the same, to promote specific adhesive interactions with other cells, including immune cells, or provide autocrine or paracrine signaling, fused cell populations, fibroblasts, chondrocytes, osteoblasts, myoblasts, endothelial, smooth muscle and neuronal cells.

Differentiated cells are reprogrammed to an embryonic-like state by transfer of nuclear contents into oocytes or by fusion with embryonic stem (ES) cells. For example, the induction of pluripotent stem cells from mouse embryonic or adult fibroblasts is accomplished by introducing one or more of the following factors, Oct3/4, Sox2, c-Myc, Klf4, and Nanog. Following contact with such factors, differentiated cells are reprogrammed and exhibit the morphology and growth properties of stem cells, e.g., ES cells, and express stem cell marker genes.

The scaffolds are seeded in vitro or in vivo. For example, scaffolds are seeded by incubating the structure in a solution containing the cells. Alternatively, cells are injected/titrated into the scaffold or recruited to migrate into the device. In yet another example, the scaffold is built in stages with each layer of the multicomponent scaffold being seeded prior to laying down of another layer or before adherences of another preformed component. Different cell types, e.g., stem vs. differentiated, support vs. therapeutic, are optionally co-resident in the scaffold housing. Cells optionally vary in phenotype, e.g., differentiation state, activation state, metabolic state, or functional state. The scaffolds are suitable for use with any cell type that one may want to transplant. Such cells include but are not limited to, various stem cell populations (embryonic stem cells differentiated into various cell types), bone marrow or adipose tissue derived adult stem cells, mesenchymal stem cells, cardiac stem cells, pancreatic stem cells, endothelaila progenitor cells, outgrowth endothelial cells, dendritic cells, hematopoietic stem cells, neural stem cells, satellite cells, side population cells. Such cells may further include but are not limited to, differentiated cell populations including osteoprogenitors and osteoblasts, chondrocytes, keratinocytes for skin, tenocytes for tendon, and intestinal epithelial cells, smooth muscle cells, cardiac muscle cells, epithelial cells, endothelial cells, urothelial cells, fibroblasts, myoblasts, chondroblasts, osteoclasts, hepatocytes, bile duct cells, pancreatic islet cells, thyroid, parathyroid, adrenal, hypothalamic, pituitary, ovarian, testicular, salivary gland cells, adipocytes, and precursor cells. For example, smooth muscle cells and endothelial cells may be employed for muscular, tubular scaffolds, e.g., scaffolds intended as vascular, esophageal, intestinal, rectal, or ureteral scaffolds; chondrocytes may be employed in cartilaginous scaffolds; cardiac muscle cells may be employed in heart scaffolds; hepatocytes and bile duct cells may be employed in liver scaffolds; epithelial, endothelial, fibroblast, and nerve cells may be employed in scaffolds intended to function as replacements or enhancements for any of the wide variety of tissue types that contain these cells. In general scaffolds of the invention may comprise any cell population competent to participate in regeneration, replacement or repair of a target tissue or organ. For example, cells are myoblasts for use in muscle regeneration.

Cells are optionally genetically manipulated by the introduction of exogenous genetic sequences or the inactivation or modification of endogenous sequences. For example, recombinant genes are introduced to cause the cells to make proteins that are otherwise lacking in the host or target tissue. Production of scarce but desirable proteins (in the context of certain tissues) is augmented by transplanting genetically engineered cells. Cells used to seed the scaffold are capable of degrading the scaffold matrix over a desired period time in order to migrate through and out of the scaffold matrix. Scaffold matrices are selected such that they are susceptible to degradation by certain cell types seeded within the matrix. For example, scaffold materials and cells are selected and designed such that all or some of the cells seeded within the scaffolds require a certain desired period of time degrade the scaffold sufficiently to migrate through it and reach the surrounding tissue. The delay in the release of the cells to the surrounding tissue is controlled by varying the composition of the scaffold, to allow optimal time to signal the cells to multiply, differentiate, or achieve various phenotypes. General mammalian cell culture techniques, cell lines, and cell culture systems are described in Doyle, A., Griffiths, J. B., Newell, D. G., (eds.) *Cell and Tissue Culture: Laboratory Procedures*, Wiley, 1998, the contents of which are incorporated herein by reference.

Cells secrete enzymes that degrade the material of the scaffold, thereby controlling the rate at which cells exit the scaffold. For example, migrating cells typically secrete collagenases and plasmin to degrade their matrix and allow cell movement. The rate of cells exiting may thus be regulated by controlling the density and susceptibility to these enzymes of oligopeptides used as either cross-links in the material or as components of the main chains. Certain materials are degraded in a preprogrammed manner independent of cell action (e.g. hydrolytic degradation of poly(lactide-co glyolide) as a degradable scaffold. The scaffolds may be prepared such that the degradation time may be controlled by using a mixture of degradable components in proportions to achieve a desired degradation rate. Alternatively, the cells themselves aid in the degradation. For example, scaffold compositions are sensitive to degradation by materials secreted by the cells themselves that are seeded within the scaffold. One example of this is the use of metalloproteinase (MMP)-sensitive substrate in the scaffold matrix; cells exit when the seeded cells have secreted sufficient MMP to begin degradation of the matrix.

Cells incubated in the scaffold are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. Such structures are used to repair abdominal wall injuries or defects such as gastroschisis. Similarly, sheetlike scaffolds seeded with dermal stem cells and/or keratinocytes are used in bandages or wound dressings for regeneration of dermal tissue.

Scaffold Compositions and Architecture

Components of the scaffolds are organized in a variety of geometric shapes (e.g., beads, pellets), niches, planar layers (e.g., thin sheets). For example, multicomponent scaffolds are constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration. Cells incubated in the scaffold are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. For example, such structures are used to repair abdominal wall injuries or defects such as gastroschisis. Similarly, sheetlike scaffolds seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by senquentially injecting or inserting matrix materials. Scaffold devices are optionally recharged with cells or with bioactive compounds, e.g., by sequential injection or spraying of substances such as growth factors or differentiation factors.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA) or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

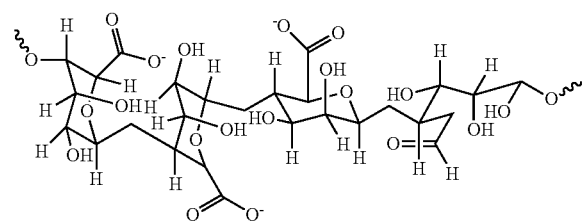

Partially oxidized alginate

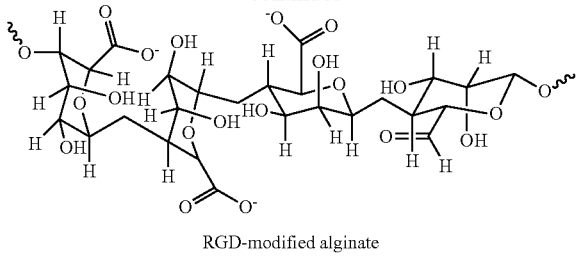

RGD-modified alginate

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly (alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Prefereably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysachharides such as alginates or modified alginates that are particularly useful for cell transplantation and tissue engineering applications.

Useful polysaccharides other than alginates include agarose and microbial polysaccharides such as those listed in the table below.

Polysaccharide Scaffold Compositions

| Polymers[a] | Structure |
|---|---|
| Fungal | |
| Pullulan (N) | 1,4-; 1,6-α-D-Glucan |
| Scleroglucan (N) | 1,3; 1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-; 1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2; 1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N—neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. In one example, the scaffold is macroporous with aligned pores of about 400-500 μm in diameter. The preparation of polymer matrices having the desired pore sizes and pore alignments are described in the Examples. Other methods of preparing porous hydrogel products are known in the art. (U.S. Pat. No. 6,511,650 incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

The bioactive composition alters a function, e.g., level of differentiation, state of activation, motility, or gene expression, of a cell. For example, at least one cell adhesion molecule is incorporated into or onto the polymer matrix. Such molecules are incorporated into the polymer matrix prior to polymerization of the matrix or after polymerization of the matrix. Examples of cell adhesion molecules include but are not limited to peptides, proteins and polysaccharides. More specifically, cell adhesion molecules include fibronectin, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) peptides and cyclic peptides, glycosaminoglycans (GAGs), hyaluronic acid (HA), condroitin-6-sulfate, integrin ligands, selectins, cadherins and members of the immunoglobulin superfamily. Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1.

Examples of some of these molecules and their function are shown in the following table.

| ECM Proteins and peptides and role in cell function | | | |
|---|---|---|---|
| Protein | Sequence | Seq. ID No: | Role |
| Fibronectin | RGDS | | Adhesion |
| | LDV | | Adhesion |
| | REDV | | Adhesion |
| Vitronectin | RGDV | | Adhesion |
| Laminin A | LRGDN | SEQ ID NO: 7 | Adhesion |
| | IKVAV | SEQ ID NO: 8 | Neurite extension |
| Laminin B1 | YIGSR | SEQ ID NO: 9 | Adhesion of many cells, via 67 kD laminin receptor |
| | PDSGR | SEQ ID NO: 10 | Adhesion |
| Laminin B2 | RNIAEIIKDA | SEQ ID NO: 11 | Neurite extension |
| Collagen 1 | RGDT | | Adhesion of most cells |
| | DGEA | | Adhesion of platelets, other cells |
| Thrombospondin | RGD | | Adhesion of most cells |
| | VTXG | | Adhesion of platelets |

Hubbell, J A (1995): Biomaterials in tissue engineering. Bio/Technology 13:565-576. One-letter abbreviations of amino acids are used, X stands for any amino acid.

Additional examples of suitable cell adhesion molecules are shown below.

| Amino acid sequences specific for proteoglycan binding from extracellular matrix proteins | | |
|---|---|---|
| SEQUENCE | SEQ.ID.NO. | PROTEIN |
| XBBXBX* | | Consensus sequence |
| PRRARV | | Fibronectin |
| YEKPGSPPREVVPRPRPGV | | Fibronectin |
| RPSLAKKQRFRHRNRKGYRSQRGHSRGR | | Vitronectin |
| rIQNLLKITNLRIKFVK | | Laminin |

Particularly preferred cell adhesion molecules are peptides or cyclic peptides containing the amino acid sequence arginine-glycine-aspartic acid (RGD) which is known as a cell attachment ligand and found in various natural extracellular matrix molecules. A polymer matrix with such a modification provides cell adhesion properties to the scaffold, and sustains long-term survival of mammalian cell systems, as well as supporting cell growth and differentiation.

Coupling of the cell adhesion molecules to the polymer matrix is accomplished using synthetic methods which are in general known to one of ordinary skill in the art and are described in the examples. Approaches to coupling of peptides to polymers are discussed in Hirano and Mooney, *Advanced Materials*, p. 17-25 (2004). Other useful bonding chemistries include those discussed in Hermanson, *Bioconjugate Techniques*, p. 152-185 (1996), particularly by use of carbodiimide couplers, DCC and DIC (Woodward's Reagent K). Since many of the cell adhesion molecules are peptides, they contain a terminal amine group for such bonding. The amide bond formation is preferably catalyzed by 1-ethyl-3-(3-dimethylaminopropyl)carbodiimide (EDC), which is a water soluble enzyme commonly used in peptide synthesis. The density of cell adhesion ligands, a critical regulator of cellular phenotype following adhesion to a biomaterial. (Massia and Hubbell, *J. Cell Biol.* 114:1089-1100, 1991; Mooney et al., J. Cell Phys. 151:497-505, 1992; and Hansen et al., *Mol. Biol. Cell* 5:967-975, 1994) can be readily varied over a 5-order of magnitude density range.

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an amphiphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A. 99:5133-5138. A method for reversible gellation following shear thinning is exemplified in Lee et al., 2003, Adv. Mat. 15:1828-1832

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydro-philic/phobic characteristics or on secondary interactions within each compartment.

Compartmentalized Device

In certain situations, a device containing compartments with distinct chemical and/or physical properties is useful. Such a configuration is particularly useful in maintaining for long time periods the "stemness" of a population of cells, while simultaneously pushing daughter cells to multiply rapidly and differentiate appropriately for participation in tissue regeneration. This system provides a long-term (e.g., months to years) stream of cells from the device. For example, an inner compartment maintains a quiescent population of multipotent stem cells, and a second compartment promotes a high rate of proliferation of the cells while inhibiting differentiation. The cells that migrate out of the second device to the surrounding tissue are instructed, as they pass through a third compartment, to differentiate appropriately. The slowly cycling cells in the inner population repopulate the intermediate compartment with a portion of their daughters, where the transient, amplifying cells provide the bulk of regenerative cells.

A comparmentalized device is designed and fabricated using different compositions or concentrations of compositions for each compartment. For example, the stem cell population is encapsulated within hydrogels, using standard encapsulation techniques (e.g., alginate microbead formation). This first hydrogel contains factors required to maintain the multipotent nature of the stem cells, either by their covalent coupling to the polymer forming the gel or by their slow and sustained release from the gel. This compartment is then coated with a second layer of gel (e.g., double layered alginate microbeads) that contains factors that do not maintain stemness, but instead promote the stem cells to rapidly proliferate and generate large numbers of more specialized daughter cells. This second compartment is formed from the same material that contains distinct factors (e.g., morphogens, growth factors, adhesion ligands), the same material in a distinct form (e.g., varying mechanical properties or porosity), or a completely different material that provides appropriate chemical/physical properties.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly). Multiple compartments are designed to stage the proliferation and specialization of the desired cells appropriately. In addition, the device is designed to have a number of compartments, in which cells enter in parallel, in contrast to serially passing through all compartments. The different compartments each induce distinct fates for the contained cells, and in this manner provide multiple specialized daughter cell populations from a single, starting stem cell population. An individual with ordinary skill in the art of stem cell biology and biomaterials can readily derive a number of potentially useful designs for a given starting cell type and desired daughter cell output.

Alternatively, the compartmentalized device is formed using a printing technology. Successive layers of a scaffold precursor doped with bioactive substances and/or cells is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (W T Brinkman et al., Photo-cross-linking of type 1 collagen gels in the presence of smooth muscle cells: mechanical properties, cell viability, and function. *Biomacromolecules*, 2003 July-August; 4(4): 890-895; W. Ryu et al., The construction of three-dimensional microfluidic scaffolds of biodegradable polymers by solvent vapor based bonding of micro-molded layers. *Biomaterials*, 2007 February; 28(6): 1174-1184; Wright, Paul K. (2001). 21st Century manufacturing. New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 Apr. 2006 Issue 2547 p 19; Replacement organs, hot off the press, C. Choi, New Scientist, 25 Jan. 2003, v2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

Growth Factors and Incorporation of Compositions into/onto a Scaffold Device

Bioactive substances that influence growth, development, movement, and other cellular functions are introduced into or onto the scaffold structures. Such substances include BMP, bone morphogenetic protein; ECM, extracellular matrix proteins or fragments thereof; EGF, epidermal growth factor; FGF-2, fibroblast growth factor 2; NGF, nerve growth factor; PDGF, platelet-derived growth factor; PlGF, placental growth factor; TGF, transforming growth factor, and VEGF, vascular endothelial growth factor. Cell-cell adhesion molecules (cadherins, integrins, ALCAM, NCAM, proteases) are optionally added to the scaffold composition.

Exemplary growth factors and ligands are provided in the tables below.

| Growth factors used for angiogenesis | | |
|---|---|---|
| Growth factor | Abbreviation | Relevant activities |
| Vascular endothelial growth factor | VEGF | Migration, proliferation and survival of ECs |
| Basic fibroblast growth factor | bFGF-2 | Migration, proliferation and survival of ECs and many other cell types |
| Platelet-derived growth factor | PDGF | Promotes the maturation of blood vessels by the recruitment of smooth muscle cells |
| Angiopoietin-1 | Ang-1 | Strengthens EC-smooth muscle cell interaction |
| Angiopoietin-2 | Ang-2 | Weakens EC-smooth muscle cell interaction |
| Placental growth factor | PlGF | Stimulates angiogenesis |
| Transforming growth factor | TGF | Stabilizes new blood vessels by promoting matrix deposition |

| Growth factors used for bone regeneration | | |
|---|---|---|
| Growth factor | Abbreviation | Relevant activities |
| Transforming growth factor-β | TGF-β | Proliferation and differentiation of bone-forming cells |
| Bone morphogenetic protein | BMP | Differentiation of bone-forming cells |
| Insulin-like growth factor | IGF-1 | Stimulates proliferation of osteoblasts and the synthesis of bone matrix |
| Fibroblast growth factor-2 | FGF-2 | Proliferation of osteoblasts |
| Platelet-derived growth factor | PDGF | Proliferation of osteoblasts |

| Growth factors used for wound healing | | |
|---|---|---|
| Growth Factor | Abbreviation | Relevant activities |
| Platelet-derived growth factor | PDGF | Active in all stages of healing process |
| Epidermal growth factor | EGF | Mitogenic for keratinocytes |
| Transforming growth factor-β | TGF-β | Promotes keratinocyte migration, ECM synthesis and remodeling, and differentiation of epithelial cells |
| Fibroblast growth factor | FGF | General stimulant for wound healing |

| Polymeric carriers used to deliver various growth factors and the type of tissues regenerated | | |
|---|---|---|
| Growth factor | Carrier | Tissue regenerated |
| EGF | Gelatin | Dermis |
|  | PET suture | Tendon |
|  | PVA sponge | Dermis |
| PDGF | Chitosan-PLLA scaffold | Craniofacial bone |
|  | CMC gel | Dermis |
|  | Fibrin | Ligament |
|  | Porous HA | Long Bone |
| TGF-β | Alginate | Cartilage |
|  | PLA | Long Bone |
|  | CaP-titanium mesh | Craniofacial bone |
|  | Polyoxamer; PEO gel | Dermis |

| Growth Factors Used for Tissue-Engineering | | | | |
|---|---|---|---|---|
| Growth factor | Abbreviation | Molecular weight (kDa) | Relevant activities | Representative supplier of rH growth factor |
| Epidermal growth factor | EGF | 6.2 | Proliferation of epithelial, mesenchymal, and fibroblast cells | PeproTech Inc. (Rocky Hill, NJ, USA) |
| Platelet-derived growth factor | PDGF-AA PDGF-AB PDGF-BB | 28.5 25.5 24.3 | Proliferation and chemoattractant agent for smooth muscle cells; extracellular matrix synthesis and deposition | PeproTech Inc. |
| Transforming growth factor-α | TFG-α | 5.5 | Migration and proliferation of keratinocytes; extracellular matrix synthesis and deposition | PeproTech Inc. |
| Transforming growth factor-β | TGF-β | 25.0 | Proliferation and differentiation of bone forming cells; chemoattractant for fibroblasts | PeproTech Inc. |
| Bone morphogenetic protein | BMP-2 BMP-7 | 26.0 31.5 | Differentiation and migration of bone forming cells | Cell Sciences Inc. (Norwood, MA, USA) |
| Basic fibroblast growth factor | bFGF/FGF-2 | 17.2 | Proliferation of fibroblasts and initiation of angiogenesis | PeproTech Inc. |
| Vascular endothelial growth factor | VEGF$_{165}$ | 38.2 | Migration, proliferation, and survival of endothelial cells | PeproTech Inc. | rH, recombinant human

| Immobilized ligands used in tissue engineering | | |
|---|---|---|
| Immobilized ligand* | ECM molecule source | Application |
| RGD | Multiple ECM molecules, including fibronectin, vitronectin, laminin, collagen and thrombospondin | Enhance bone and cartilage tissue formation in vitro and in vivo<br>Regulate neurite outgrowth in vitro and in vivo<br>Promote myoblast adhesion, proliferation and differentiation<br>Enhance endothelial cell adhesion and proliferation |
| IKVAV YIGSR RNIAEIIKDI | Laminin | Regulate neurite outgrowth in vitro and in vivo |
| Recombinant fibronectin fragment (FNIII$_{7-10}$) | Fibronectin | Promote formulation of focal contacts in pre-osteoblasts |
| Ac-GCRDGPQ-GIWGQDRCG | Common MMP substrates, (e.g. collagen, fibronectin, laminin) | Encourage cell-mediated proteolytic degradation, remodeling and bone regeneration (with RGD and BMP-2 presentation) in vivo |

*Sequences are given in single-letter amino acid code.
MMP, matrix metalloproteinase.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

Carrier systems for tissue regeneration are described in the table below.

-continued

| Polymeric carriers used to deliver various growth factors and the type of tissues regenerated | | |
|---|---|---|
| Growth factor | Carrier | Tissue regenerated |
| rhBMP-2 | Collagen sponge | Long bone<br>Craniofacial bone |
|  | HA-TCP granules | Spinal bone |
|  | HA-collagen | Long bone |
|  | PLA-DX-PEG | Ectopic and hip bone |
| rHBMP-7 | HA | Spinal bone |
|  | Collagen-CMC | Spinal bone |
|  | Porous HA | Craniofacial bone |

-continued

Polymeric carriers used to deliver various growth factors and the type of tissues regenerated

| Growth factor | Carrier | Tissue regenerated |
|---|---|---|
| bFGF | Chitosan | Dermis |
| | Heparin-alginate | Blood vessels |
| | EVAc microspheres | Blood vessels |
| | Fibrin matrices | Blood vessels |
| VEGF | PLG scaffold | Blood vessels |
| | PLG scaffold | Blood vessels |
| | PLG microspheres | Blood vessels |
| | Fibrin mesh | Blood vessels |

Abbreviations: PET, poly (ethylene terepthalate); PVA, polyvinyl alcohol; PLLA, poly(L-lactic acid); CMC, carboxymethylcellulose; HA, hydroxyapatite; PLA, poly(D,L-lactic acid); CaP, calcium phosphate; PEO, poly (ethylene oxide); TCP, tricalcium phosphate; PEG, poly (ethylene glycol); -DX-, -p-dioxanone-; EVAc, ethylene vinyl acetate; PLG, poly (lactide-co-glycolide).

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, longterm presentation of a bioactive substance on the scaffold in a defined conformation. Exemplary reagents for covalent coupling of such substances are provided in the table below.

Methods to covalently couple peptides/proteins to polymers

| Functional Group of Polymer | Coupling reagents and cross-linker | Reacting groups on proteins/peptides |
|---|---|---|
| —OH | Cyanogen bromide (CNBr) | —NH$_2$ |
| | Cyanuric chloride | |
| | 4-(4,6-Dimethoxy-1,3,5-triazin-2-yl)-4-methyl-morpholinium chloride (DMT-MM) | |
| —NH$_2$ | Diisocyanate compounds | —NH$_2$ |
| | Diisothoncyanate compounds | —OH |
| | Glutaraldehyde | |
| | Succinic anhydride | |
| —NH$_2$ | Nitrous Acid | —NH$_2$ |
| | Hydrazine + nitrous acid | —SH |
| | | —Ph—OH |
| —NH$_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive substances are capable of inducing migration of the transplanted cells and their progeny out of the polymer matrix. Other preferred bioactive substances are capable of maintaining cell viability, promoting cell proliferation or preventing premature terminal differentiation of the transplanted cells. Such bioactive substances are used alone or in combination to achieve the desired result.

Bioactive substances suitable for use in the present invention include, but are not limited to: growth factors, hormones, neurotransmitters, neurotransmitter or growth factor receptors, interferons, interleukins, chemokines, cytokines, colony stimulating factors, chemotactic factors, MMP-sensitive substrate, extracellular matrix components; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). Splice variants of any of the above mentioned proteins, and small molecule agonists or antagonists thereof that may be used advantageously to alter the local balance of pro and anti-migration and differentiation signals are also contemplated herein.

Examples of cytokines as mentioned above include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Suitable bioactive substances useful in accordance with the invention also include but are not limited to DNA molecules, RNA molecules, antisense nucleic acids, ribozymes, plasmids, expression vectors, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, and cytotoxins.

For some applications, the scaffolds of the invention includes at least one cell growth factor that prevents premature terminal differentiation of the transplanted cells in the polymer matrix and induces migration of the transplanted cells and their progeny out of the polymer matrix. Cell growth factors are incorporated into the polymer matrix prior to polymerization of fabrication or may be coupled to the polymer matrix after polymerization. The choice of growth factor will depend upon the type of cells and the influence of a particular growth factor on those cells such that the cells are directed to bypass their normal tendency to differentiate, and remain in a proliferative phase until a sufficient number of cells is attained to regenerate the targeted tissue and for the cells to have also migrated from the scaffold.

Scaffolds of the invention optionally comprise at least one non-viral gene therapy vector such that either the transplanted cells or host cells in the vicinity of the implant would take up and express gene that lead to local availability of the desired factor for a desirable time frame. Such non-viral vectors include, but are not limited to, cationic lipids, polymers, targeting proteins, and calcium phosphate.

For regeneration of muscular tissue, the cells seeded in the scaffold are myoblasts and the preferred combination of growth factors is HGF and FGF2. FGF2 is particularly useful in preventing the premature differentiation of the transplanted cells, while HGF induces migration of the cells from the scaffold. The incorporation of the two growth factors significantly increased the viability and migration of the seeded myoblasts as discussed below.

Clinical Applications

The devices and methods are useful for generation or regeneration of a number of different organs and tissue types such as musculoskeletal tissue. In the latter case, environmental cues work in concert with transcription factors to activate satellite cells, induce them to proliferate and eventually differentiate into mature muscle fibers. Numerous trophic factors play a role as initiators of satellite cell activation. Of these candidate trophic factors, both hepatocyte growth factor (HGF) and members of the fibroblast growth factor (FGF) family have been demonstrated to have a physiological role in skeletal muscle regeneration. Both types of factors initiate satellite cell activation, stimulate satellite cells to enter the cell cycle in vivo and are potent mitogens for satellite cells. In addition, the receptor for HGF, c-met, is expressed in both quiescent and activated satellite cells, and FGF-2 is present in the basement membrane surrounding developing myotubes. Both HGF and FGF2 are heparin binding proteins which depend on heparin sulfate proteoglycans (HSPG) to facilitate receptor activation. While HSPG's are ubiquitous on the surface of the cells of mammals, a specific family of HSPG's called Syndecans are involved in FGF2 signaling. In addition, Syndecan 3 and 4 are expressed on both quiescent and activated satellite cells indicating that HGF and FGF2 play important physiological roles in regulating satellite cell activation.

Current approaches therapeutically intervene in the muscle regenerative process have been limited by significant drawbacks. The invention provides solutions to these drawbacks of earlier methods. Three of such approaches are described below. First, cells in the tissues are stimulated to re-enter the cell cycle and repopulate lost or damaged tissues by the injection of growth factors into the site of interest. The second approach is based on the current interest in gene therapy and targets the intrinsic cell proliferation and differentiation program of muscle forming cells. The third approach is based on the delivery of exogenous cells, expanded in culture, to repair the defect and restore function to the tissue. Current strategies related to the third approach include direct injection of cells into the injury site, the utilization of a carrier to provide an artificial matrix for cell delivery, or a combination of cell, matrix and growth factor delivery to increase regeneration. Cell transplantation approaches have focused on satellite cells, and are gaining growing interest as a potential treatment alternative for patients with musculodegenerative diseases such as muscular dystrophy, and for chronic or congenital cardiomyopathies. However, while animal studies were initially promising, attempts to transplant human satellite cells have been disappointing, because transplanted myogenic cells underwent rapid and massive necrosis, resulting in less than 5% of transplanted cells incorporating into the host myofibers after 48 hours.

A solution to problems, e.g., poor survival and integration of myogenic cells into host musculature, is addressed by the compositions and methods described herein. The invention provides a new approach to tissue engineering and regenerative medicine. The systems mediate and regulate delivery of cells on a material that maintains the viability of the cells for extended time periods while simultaneously encouraging outward migration of the cells to populate surrounding host tissue in need of regeneration. Appropriate combinations of scaffold architecture, adhesion ligands that maintain viability and allow migration, and growth factors that regulate cell phenotype are used to inform cell behavior and exert complex control over the fate of the transplanted cells.

In addition to generation or regeneration of muscle tissue, stem cells have been identified for many different types of tissues, including the human heart (*Proceedings of the National Academy of Sciences* (DOI: 10.1073/pnas.0600635103)), delivering them in a way which is therapeutically effective has proven to be a challenge. Neither intravascular delivery nor direct injection into target tissue have proven successful. Intravascular delivery with the objective that the cells will find their way to where they are needed, has proven highly inefficient. Direct injection into the site has also delivered poor results, with an extremely high necrosis rate and low cell integration rate.

The biocompatible scaffolds of the invention are useful in a broad range of in vivo and in vitro regenerative medicine and tissue engineering. Devices are designed and manufactured for a wide variety of injuries, diseases, conditions and cell therapies, and delivered to the treatment location using surgical, endoscopic, endovascular, and other techniques. The devices degrade and resorb after the treatment is successfully completed or remain in place permanently or semi-permanently. Cells are seeded ex vivo into the scaffold with autologous or allogeneic cells. The devices are particularly useful in regenerating heart tissue (ischemia lesions and scarring), dermal tissue (scarring, ulcers, burns), CNS tissue (spinal cord injury, MS, ALS, dopamine shortage), and for skeletal-muscle system repairs (tendons, ligaments, discs, post-surgical, hernias)

A method for treating a patient in need of tissue regeneration, replacement or repair comprises the step implanting a scaffold in or near the tissue in need of regeneration, repair or replacement. This method for treating a patient in need of muscle repair involves implanting in the patient a biocompatible scaffold containing a macroporous, polymer matrix having at least one cell adhesion molecule incorporated therein, a population of myoblast cells capable of muscle regeneration transplanted within the polymer matrix; and at least one cell growth inductive factor that prevents terminal differentiation of the transplanted cells in the polymer matrix and induces migration of the transplanted cells and their progeny out of the polymer matrix. For example, the cell growth inductive factor(s) is a combination of HGF and FGF2.

The devices are useful to treat acute and chronic tissue disease or defects in humans as well as animals such as dogs, cats, horses, and other domesticated and wild animals. Conditions treated include neuropathological disorders such as Amyotrophic Lateral Sclerosis (ALS), multiple sclerosis, polyneuropathy, multiple sclerosis (MS), Parkinson's, and epilepsy. Retinal diseases such as retinal degeneration and corneal injury (caustic) also can be treated with the devices. The device can also be used to treat various heart and respiratory diseases such as myocardial infarction (MI), congestive heart failure (CHF), coronary artery disease (CAD), and cardiomyopathy or respiratory diseases, e.g., chronic respiratory diseases (CRDs) or pulmonary fibrosis, respectively.

Additionally, the device is used to treat bone and cartilage defects/diseases such as periodontitis or a skull injury generally, but also with craniotomy. Moreover, the device is implanted into or adjacent to neural tissues, e.g., to treat spinal chord injuries such as a crushed spinal cord. The device is used in other surgeries such as in masectomies to heal and augment reconstruction of breast tissue.

Other uses include those that supply cells for treatment inhibition of autoimmune diseases, such as Lupus, Mastocytosis, *Scleroderma*, and Rheumatoid Arthritis. The device are also useful to supply cell for treating blood disorders such as Sickle-cell Anemia or vacular disorders such as peripheral arterial disease (PAD), Peripheral Ischemia, or diabetes.

Other diseases the device can be used to treat are gastrointestinal (GI) graft vs host, fenal failure, or Crohn's Disease. Additionally the device used for male infertility; for example, the device is implanted into a testicle and functions as a surrogate spermatogonia to produce a steady stream of sperm cells. Skin diseases, injuries, or defects that are treated with the device include skin burns and ulcers. Surgical defects such as those resulting from Caesarian section births and those resulting from cosmetic surgery are particularly amenable to treatment using flexible device scaffolds. Alternatively, the delivered or programmed/reprogrammed cells delivered from the device maintain tissue and organ structure and function (e.g., prevent age-related alterations or deterioration).

The devices increase the efficacy of stem and transgenic cell therapies, and the devices are tailored to suit each clinical problem with the appropriate choice of scaffold composition, pore size, bioactive substance(s) and cell types. The device solves the major problem of efficiently integrating therapeutic cells into target tissue. Physicians place the device near the site requiring therapy or regeneration, where it delivers a flow of cells to the target site. Unlike traditional scaffolds, the device exports cells after they have incubated, replicated and matured inside the device. The device has shown 20X+ improvements in viable cell delivery and tissue re-growth for damaged skeletal muscle. By matching its design to the specific cell type biochemistry, the device causes an extended stream of matured cells to migrate into the target tissue.

The devices offer several advantages over other scaffold systems. Maximum therapeutic efficacy is achieved, because cells are delivered in prime condition at the right time in the right quantities directly to the locus of disease or injury. Sustained delivery facilitates accretive integration of therapeutic cells into tissue at a desired location. The devices has been shown to be more efficient in viable cell delivery (110% for this device vs. 5% for the best alternative techniques). Thus, fewer cells are needed per treatment allowing successful therapies which might have failed at lower cell delivery rates. Lower cell numbers also permit autologous grafts, because fewer cells need to be harvested from the patient to be treated and 1 Less time is required between harvest and graft to proliferate cells in vitro. Since fewer cells are required, relative rare cells can be used. The devices also permit less expensive allogeneic grafts. Other advantages include rapid determination of the therapeutic benefit of any treatment and faster tissue growth and enhanced healing.

Vaccine Device

The biocompatible scaffolds are useful as delivery vehicles for cancer vaccines. The cancer vaccine stimulates an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. These treatments optionally involve cytokine exposure to activate the cells, genetic manipulation to overexpress cytokines from the cells, or priming with tumor specific antigens or cocktails of antigens, and expansion in culture. Dendritic cell vaccines activate antigen presenting cells directly, and their proliferation, activation and migration to lymph nodes is regulated by scaffold compositions to enhance their ability to elicit an immune response. Types of cancers to be treated include central nervous system (CNS) cancers, CNS Germ Cell tumor, lung cancer, Leukemia, Multiple Myeloma, Renal Cancer, Malignant Glioma, Medulloblastoma, and Melanoma.

For the purpose of eliciting an antigen-specific immune response, a scaffold device is implanted into a mammal. The device is tailored to activate immune cells and prime the cells with a specific antigen thereby enhancing immune defenses and destruction of undesired tissues and targeted microorganisms such as bacterial or viral pathogens. The device attracts appropriate immune cells, such as macrophages, T cells, B cells, NK cells, and dendritic cells, by containing and/or releasing signaling substances such as GM-CSF. These signaling substances are incorporated in the scaffold composition in such a way as to control their release spatially and temporally using the same techniques used to integrate other bioactive compounds in the scaffold composition.

Once the immune cells are inside the device, the device programs the immune cells to attack or cause other aspects of the immune system to attack undesired tissues (e.g., cancer, adipose deposits, or virus-infected or otherwise diseased cells) or microorganisms. Immune cell activation is accomplished by exposing the resident immune cells to preparations of target-specific compositions, e.g., ligands found on the surface of the undesired tissues or organisms, such as cancer cell surface markers, viral proteins, oligonucleatides, peptide sequences or other specific antigens. For example, useful cancer cell-specific antigens and other tissue or organism-specific proteins are listed in the table below.

The device optionally contains multiple ligands or antigens in order to create a multivalent vaccine. The compositions are embedded in or coated on the surface of one or more compartments of the scaffold composition such that immune cells migrating through the device are exposed to the compositions in their traverse through the device. Antigens or other immune stimulatory molecules are exposed or become exposed to the cells as the scaffold composition degrades. The device may also contain vaccine adjuvants that program the immune cells to recognize ligands and enhance antigen presentation. Exemplary vaccine adjuvants include chemokines/cytokines, CpG rich oligonucleotides. or antibodies that are exposed concurrently with target cell-specific antigens or ligands.

The device attracts immune cells to migrate into a scaffold where they are educated in an antigen-specific manner and activated. The programmed immune cells are then induced to egress towards lymph nodes in a number of ways. The recruitment composition and deployment signal/composition, e.g., a lymph node migration inducing substance, is released in one or more bursts, programmed by the method of incorporation and/or release from the scaffold material, or controlled by the sequential degradation of scaffold compartments which contain the attractant. When a burst dissipates, the cells migrate away. Compartments containing repulsive substances are designed to degrade and release the repulsive substance in one or more bursts or steadily over time. Relative concentration of the repulsive substances cause the immune cells to migrate out of the device. Alternatively, cells which have been placed in or have migrated into the device are programmed to release repulsive substances or to change their own behavior. For example, localized gene therapy is carried out by cell exposure to plasmid DNA attached to the scaffold. Useful repulsive substances include chemokines and cytokines. Alternatively, the device may cause immune cells to egress by degrading and releasing them.

Target disease states, stimulatory molecules and antigens useful in vaccine device construction are listed below.

Bioactive Factors to Promote Immune Responses
a. Interleukins: IL-1, IL-2, IL-3, IL-4, IL-5, IL-6, IL-8, IL-10, IL-12 1L-15, 1L-18 etc.
b. TNF-α
c. IFN-γ
d. IFN-α
e. GM-CSF
f. G-CSF
g. Ftl-3 ligand
h. MIP-3 β (CCL19)
i. CCL21
j. M-CSF
k. MIF
l. CD40L
m. CD3
n. ICAM
o. Anti CTLA-4 antibodies
p. TGF-β
q. CPG rich DNA or oligonucleotides
r. Sugar moieties associated with Bacteria: Lipopolysacharides (LPS) is an example
s. Fas ligand
t. Trail
u. Lymphotactin
v. Mannan (M-FP)
w. Heat Shock Proteins (apg-2, Hsp70 and Hsp 90 are examples)

Diseases and Antigens—Vaccination Targets
a. Cancer: antigens and their sources
i. Tumor lysates extracted from biopsies
ii. Irradiated tumor cells
iii. Melanoma
1. MAGE series of antigens (MAGE-1 is an example)
2. MART-1/melana
3. Tyrosinase
4. ganglioside
5. gp100
6. GD-2
7. O-acetylated GD-3
8. GM-2
iv. Breast Cancer
1. MUC-1
2. Sos1
3. Protein kinase C-binding protein
4. Reverse trascriptase protein
5. AKAP protein
6. VRK1
7. KIAA1735
8. T7-1, T11-3, T11-9
v. Other General and Specific Cancer Antigens
1. *Homo Sapiens* telomerase ferment (hTRT)
2. Cytokeratin-19 (CYFRA21-1)
3. SQUAMOUS CELL CARCINOMA ANTIGEN 1 (SCCA-1), (PROTEIN T4-A)
4. SQUAMOUS CELL CARCINOMA ANTIGEN 2 (SCCA-2)
5. Ovarian carcinoma antigen CA125 (1A1-3B) (KIAA0049)
6. MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3)
7. CTCL tumor antigen se1-1
8. CTCL tumor antigen se14-3
9. CTCL tumor antigen se20-4
10. CTCL tumor antigen se20-9
11. CTCL tumor antigen se33-1
12. CTCL tumor antigen se37-2
13. CTCL tumor antigen se57-1
14. CTCL tumor antigen se89-1
15. Prostate-specific membrane antigen
16. 5T4 oncofetal trophoblast glycoprotein
17. Orf73 Kaposi's sarcoma-associated herpesvirus
18. MAGE-C1 (cancer/testis antigen CT7)
19. MAGE-B1 ANTIGEN (MAGE-XP ANTIGEN) (DAM10)
20. MAGE-B2 ANTIGEN (DAME)
21. MAGE-2 ANTIGEN
22. MAGE-4a antigen
23. MAGE-4b antigen
24. Colon cancer antigen NY-CO-45
25. Lung cancer antigen NY-LU-12 variant A
26. Cancer associated surface antigen
27. Adenocarcinoma antigen ART1
28. Paraneoplastic associated brain-testis-cancer antigen (onconeuronal antigen MA2; paraneoplastic neuronal antigen)
29. Neuro-oncological ventral antigen 2 (NOVA2)
30. Hepatocellular carcinoma antigen gene 520
31. TUMOR-ASSOCIATED ANTIGEN CO-029
32. Tumor-associated antigen MAGE-X2
33. Synovial sarcoma, X breakpoint 2
34. Squamous cell carcinoma antigen recognized by T cell
35. Serologically defined colon cancer antigen 1
36. Serologically defined breast cancer antigen NY-BR-15
37. Serologically defined breast cancer antigen NY-BR-16
38. Chromogranin A; parathyroid secretory protein 1
39. DUPAN-2
40. CA 19-9
41. CA 72-4
42. CA 195
43. Carcinoembryonic antigen (CEA)
b. AIDS (HIV Associated Antigens)
i. Gp120
ii. SIV229
iii. SIVE660
iv. SHIV89.6P
v. E92
vi. HCl
vii. OKMS
viii. FVIIIRAg
ix. HLA-DR (Ia) antigens
x. OKM1
xi. LFA-3
c. General Infectious Diseases and Associated Antigens
i. Tuberculosis
1. *Mycobacterium tuberculosis* antigen 5
2. *Mycobacterium tuberculosis* antigen 85
3. ESAT-6
4. CFP-10
5. Rv3871
6. GLU-S
ii. Malaria
1. CRA
2. RAP-2
3. MSP-2
4. AMA-1
iii. Possible mutant influenza and meningitis strains
d. Neuro Protection—Protect Against Neurological Diseases (e.g., Alzheimer's, Parkinsons, Prion Disease)
1. Classes of self CNS antigens
2. human alpha-synuclein (Parkinson's)

3. beta amyloid plaques (Alzheimer's)
e. Autoimmune Diseases (multiple sclerosis, Rheumatoid arthritis etc)
  i. Disease linked MHC antigens
  ii. Different classes of Self antigens
  iii. Insulin
  iv. Insulin peptide B9-23
  v. glutamic acid
  vi. decarboxylase 65 (GAD 65)
  vii. HSP 60
Disease linked T-cell receptor (TCR)

Example 1

Designing Scaffolds to Enhance Transplanted Myoblasts Survival and Myogenesis

Myoblast transplantation is currently limited by poor survival and integration of cells into host musculature. Transplantation systems that enhance the viability of the cells and induce their outward migration to populate injured muscle enhances the success of this approach to muscle regeneration. Enriched populations of primary myoblasts were seeded onto delivery vehicles formed from alginate, and the role of vehicle design and local growth factor delivery in cell survival and migration were examined. Only 5+/−2.5%, of cells seeded into nanoporous alginate gels survived for 24 hrs, and only 4+/−0.5% migrated out of the gels. Coupling cell adhesion peptides (e.g., $G_4RGDSP$) to the alginate prior to gelling slightly increased the viability of cells within the scaffold to 16+/−1.4%, and outward migration to 6+/−1%. However, processing peptide-modified alginate gels to yield macroporous scaffolds, in combination with sustained delivery of HGF and FGF2 from the material, dramatically increased the viability of seeded cells over a 5 day time-course, and increased outward migration to 110+/−12%. These data indicate that long-term survival and migration of myoblasts placed within polymeric delivery vehicles is greatly increased by appropriate scaffold composition, architecture, and growth factor delivery. This system is particularly useful in the regeneration of muscle tissue, and is broadly useful in the regeneration of other tissues.

The presence of bioactive compositions in or on a scaffold material maintains the viability of the cells for extended time periods while simultaneously encouraging outward migration of the cells to populate surrounding host muscle fibers. Biodegradable polymer matrices that co-deliver satellite cells and inductive molecules that signal endogenous cells to participate in muscle regeneration are specifically useful in this approach. The role of coupling cell adhesion ligands to the matrix, material pore structure, and growth factor delivery from the material were studied in vitro. Alginate, a hydrophilic, biocompatible polysaccharide derived from seaweed, has carboxylic acid functional groups that allow covalent modification with cell adhesion peptides, allowing for the controlled presentation of signals that induce tissue development. In addition, controlling the molecular weight distribution of the polymer used to form gels allows one to regulate gel degradation and to increase the viability of alginate encapsulated cells. Taken together, these properties make alginate hydrogels a useful model material for these studies. Finally, in addition to primary myoblasts, a myoblasts cells line (C2C12 cells) that produces characteristic muscle proteins, was used as a model system for the analysis of the expression of myogenic proteins.

The following materials and methods were used to generate the data described herein.

Alginate Modification

Low molecular weight ($M_w$=5.3×10$^4$ g/mol, abbreviated as LMW) modified alginate, was produced by irradiating ultra pure MVG alginate powder (Pronova, Oslo Norway) with a cobalt-60 source for 4 hours at a γ-dose of 5.0 Mrad (Phoenix Lab, University of Michigan, Ann Arbor, USA). High molecular weight (MVG, Pronova, Mw=2.7×10$^5$ g/mol) alginate, ultra pure grade was also used to fabricate scaffolds. Both alginates were modified with covalently conjugated oligopeptides with a sequence of $G_4RGDSP$ (Commonwealth Biotechnology Inc.) at an average density of 3.4 mM peptide/mole of alginate monomer, using carbodiimide chemistry known in the art (e.g., Rowley, Madlambayan et al. 1999 Bio. Mat. Res. 60:217-233; Rowley J. 2002 Bio. Mat. Res. 20:45-53). 2% irradiated alginate solutions were frozen and lyophilized until completely dry. Lyophilized alginate was added to MES buffer (Sigma) to yield a 1% w/v solution and EDC, Sulfo-NHS and RGDSP peptide were added to the dissolved alginate and allowed to react for 20 hours. The reaction was quenched with hydroxylamine and the solution was dialyzed with decreasing concentrations of NaCl (7.5%, 6.25%, 5%, 3.75%, 2.5%1.25% and 0%), over 3 days. The solution was purified via the addition of activated charcoal and subsequent sterile filtration. Sterile filtered alginate was frozen and lyophilized and stored at −20° C. Finally, the modified alginates were reconstituted in calcium-free DMEM (Invitrogen) to obtain 2% w/v solution (50% LMW; 50% MVG used in all experiments) prior to gelation. Reconstituted alginate was stored at 4° C.

Scaffold Fabrication

Three physical forms of scaffolds were prepared: nanoporous, microporous, and macroporous. To fabricate nanoporous alginate scaffolds, 5 ml non-modified or peptide modified alginate containing myoblasts (10$^6$ cell/ml) was crosslinked by adding 200 μl of $CaSO_4$ (0.41 g $CaSO_4$/ml dd $H_2O$) (Aldrich), and the resulting solution was expressed into molds (2×2×5 mm) constructed from polyvinylsulfoxane (PVS), (Kerr). The alginate was allowed to completely gel, and placed at 37° C. in high glucose DMEM. To form microporous (10-20 μm pores) scaffolds, alginate was gelled in the absence of cells and then frozen at −120° C. The frozen scaffolds were lyophilized and stored at −4° C. until seeded with cells. To fabricate macroporous alginate scaffolds (400-500 μm diameter aligned pores), the alginate/calcium sulfate solution was expressed into the PVS mold containing wire porogens (RMO othodontic wire, PO Box 17085, Denver Colo.). A sterile glass plate was placed over the mold containing the alginate, and left undisturbed for 30 minutes. After the alginate has completely gelled (30 minutes), the alginate containing the wire porogens was frozen at −70° C. The frozen alginate gels were lyophilized overnight, wire porogens were carefully removed, and the dried scaffolds were stored at −20° C. until seeded with cells.

Myoblast Cultures

Myoblasts were derived from four week old C57BL/6 mice hindlimb skeletal musculature. Under sterile conditions, the tibialis muscle of the hindlimb was surgically excised, finely minced and disassociated in 0.02% Trypsin (GIBCO) and 2% Collagenase type 4 (Worthington Biochemical, Lakewood, N.J.) for 60 minutes at 37° C./5% $CO_2$ while agitating on an orbital shaker. Disassociated cells were strained through a 70 μm sieve, centrifuged at 1600 rpm for 5 minutes and resuspended in high glucose DMEM, with added pyruvate (GIBCO). Media was further supplemented with 10% Fetal Bovine Serum (FBS) and 10% penicillin/streptomycin (P/S), (GIBCO) and this medium was used in all cell culture studies. Cells were plated and cultured at 37° C./5% $CO_2$ for 72 hours before media change. After 72 hours in culture, the media was changed every 48 hours until cells were 80% confluent (about 7 days). Cells were collected via centrifugation and overlaid on a Percoll gradient (Amersham Biosciences, Uppsala, Sweden) in a 15 ml Falcon tube. The gradient consisted of 3 ml of 20% Percoll diluted in PBS (GIBCO), 3 ml of 30% percoll diluted in DMEM (Invitrogen) and 3 ml of 35% Percoll diluted in Ham's F-12 (GIBCO). Cells were immediately centrifuged at 1600 rpm for 20 minutes at 25° C. The cells from the 30% fraction were collected and resuspended in high glucose DMEM.

Immunohistochemistry

To characterize myoblast cultures for the expression of myogenic proteins, Percoll purified primary myoblasts were plated on sterile cover slips overnight, and fixed in 0.2% paraformaldehyde for 20 minutes. Coverslips were rinsed in phosphate buffered saline with 0.5% Triton-X (PBS-X), and incubated in Hoechst nuclear dye (1:1000). Coverslips were also incubated in an anti-desmin (1/100) monoclonal antibody (Chemicon, Temecula Calif.) followed by immunofluorescent secondary antibody (1:1000), (FITC, Jackson Labs, West Grove, Pa.). After secondary antibody binding, coverslips were mounted on glass slides with aqueous mounting medium and sealed with clear nail polish. Slides were viewed with a conventional fluorescent light microscope (Nikon Eclipse E-800, Tokyo, Japan) or stored in total darkness for later analysis. Images were captured utilizing NIH imaging software (National Institutes of Health, Bethesda, Md.), Spot digital camera and Adobe Photoshop.

Western Blot

Total cytoplasmic protein was collected by finely mincing modified alginate scaffolds containing primary myoblasts and placing the resultant solutions in 1.5 ml Eppendorf tubes. Fifty microliters of passive lysis buffer (Promega, Madison Wis.) was added directly to the minced scaffold and incubated at 37° C. for 10 minutes. The amount of protein in each sample was quantified by dilution of 1 μm of sample in 200 μm protein assay reagent (BioRad), and the absorbance was measured at 595 nm (Sunrise spectrometer).

All samples were denatured using standard SDS page protocols, loaded at 25 μg total protein per well in 8% Tris Glycine polyacrylimide gels (Ready Gels, BioRad) and electrophoresed at 100 volts for 120 min (Laemmli, 1970). After electrophoresis, proteins were transferred to PDVF membranes (BioRad) at 100 volts for one hour utilizing the BioRad mini-blot. PDVF membranes were blocked in 1% bovine serum albumin (BSA) in Tris buffered saline with 0.1% Tween-20 (TBS-T) overnight at 4° C. After blocking, PDVF membranes were incubated in the appropriate primary monoclonal antibody, either for desmin (1/100), myogenin (1/100), or MyoD (1/100), (Santa Cruz Biotechnologies, CA), for one hour at room temperature. Membranes were subsequently rinsed for 30 minutes in TBS-T (15 min×2), and incubated in horseradish peroxidase conjugated goat anti-mouse secondary antibody (BioRad), 1:1000 in TBS-T, for 1 hour. Membranes were rinsed in TBS-T for 30 min. (15 min×2) and proteins were detected via chemiluminescent detection kit (ECL, Amersham) and visualized by exposure to Hyperfilm ECL (Amersham).

Growth Factor Incorporation and Release Kinetics

To determine the release kinetics of HGF incorporated into modified binary alginate scaffolds, a quantitative sandwich enzyme immunoassay technique (ELISA) was employed. Recombinant HGF protein (Santa Cruz Biotechnologies, CA.) was incorporated into alginate solutions prior to gelling (500 ng/ml), and gels were cast as previously described. After the gels had completely polymerized they were cut into 5 mm squares and placed in 24 well plates, and 1 ml of PBS was added to each well. At various time points the PBS was removed and stored at 4° C. and fresh PBS added to the scaffolds. The PBS samples were measured for total HGF content via quantitative ELISA (Quantikine), and the results were compared to the initial HGF incorporated. To determine the incorporation efficiency and release kinetics of FGF2, 5 μci of $I^{125}$-Bolton Hunter (PerkinElmer Life Sciences, Boston, Mass.) labeled FGF2 was incorporated into 2.5 ml of the alginate solution prior to gelling. After gelling, gels were cut into squares (2×10×10 mm). Approximately 1 μci of labeled FGF2 was incorporated into each scaffold. Alginate scaffolds were placed in separate polypropylene tubes containing 3 ml of phosphate buffered saline (PBS) and incubated at 37° C. At various time points the PBS was removed from the tubes, and fresh PBS was added to the scaffolds. The release of FGF2 from the scaffolds was determined by measuring the radioactivity present in the PBS removed from the scaffolds with a gamma counter (Beckman) and comparing the result to the initial total $I^{125}$ FGF2 incorporated into the sample.

Migration and Viability

To determine the viability of primary myoblasts seeded in alginate scaffolds and to measure their ability to migrate out of the scaffolds, purified primary myoblasts were seeded in three dimensional alginate scaffolds (2×10$^6$ cells/ml) in 24 well plates. A solution of cells in medium (50 μl) was pipeted into each lyophilized scaffold; the medium was rapidly absorbed. The resulting viability and migration of myoblasts from alginate scaffolds, with both HGF and FGF2 (250 ng/scaffold) incorporation was subsequently measured by maintaining scaffolds in culture for various time points. To analyze the viability of cells within the scaffolds, the scaffolds were finely minced, treated with 50 μl of trypsin and 50 μl of 5 mM EDTA for 5 minutes. Twenty μl of dissolved alginate and suspended cells was then added to 20 μl of 4% Trypan Blue Solution (Sigma). The percent of viable cells was determined via trypan blue exclusion (dead cells appear blue due to their inability of exclude trypan blue from their nucleus), as viewed on a hemocytometer under standard microscopic conditions (Nikon Eclipse E800, 20X). To measure migration of myoblasts from the scaffolds, scaffolds were placed in new 24 well plates at various time points and the cells that had colonized the 24 well plates over the previous 24 hours were removed via trypsinization and counted in a Coulter Counter (Beckman Corp.). The total number of cells that migrated out of the scaffold was normalized to the total number of cells initially seeded into the alginate scaffolds.

SEM Scaffold Characterization

The size and orientation of pores in alginate scaffolds were imaged utilizing a scanning electron microscope (ISI-DS 130, Topcon Techn. CA). All samples were dried and sputter coated (Desk II, Denton Vacum; NJ) prior to analysis.

Characterization of Myoblasts Isolated from Murine Hindlimb

Primary cells isolated from skeletal muscle were plated on coverslips and analyzed by staining with a Hoescht nuclear specific stain, and immunohistochemical staining for desmin. Analysis via light microscopy of random microscopic fields revealed that the initial isolation yielded a heterogeneous population of cells, 75% of which expressed desmin (FIG. 1A). To enrich the cell culture for myogenic cells, initial primary cell isolates were expanded in culture for 7 days, and subsequently purified via Percoll density gradient fractionation. The resulting cultures consisted of a 95% desmin positive population (FIG. 1B).

Role of Peptide Modification

Figure 2:
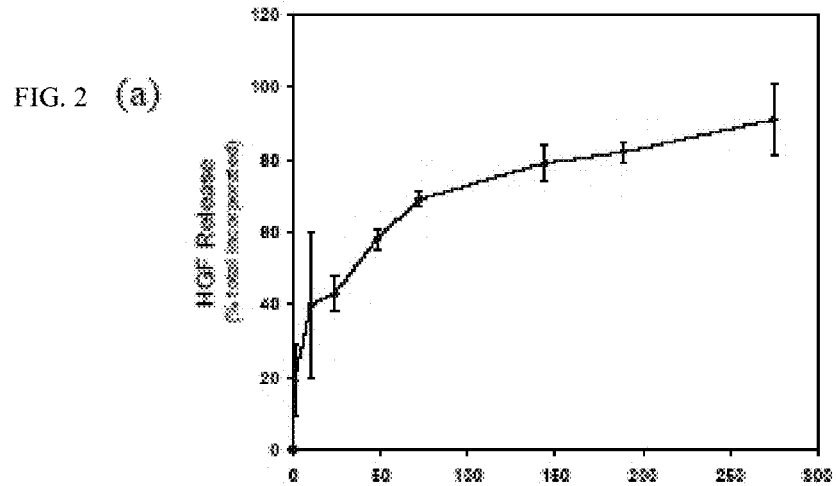
FIG. 2A is a line graph showing HGF release from macroporous, non peptide modified alginate scaffolds, values represent mean and standard deviation (n=5).
FIG. 2B is a bar graph showing Viability and FIG. 2C is a bar graph showing cumulative migration of primary myoblasts, in and from respectively, nanoporous scaffolds (■), nanoporous scaffolds releasing HGF (▨) and microporous scaffolds releasing HGF (▥). Values represent mean and SD (n=6).
Figure 2:
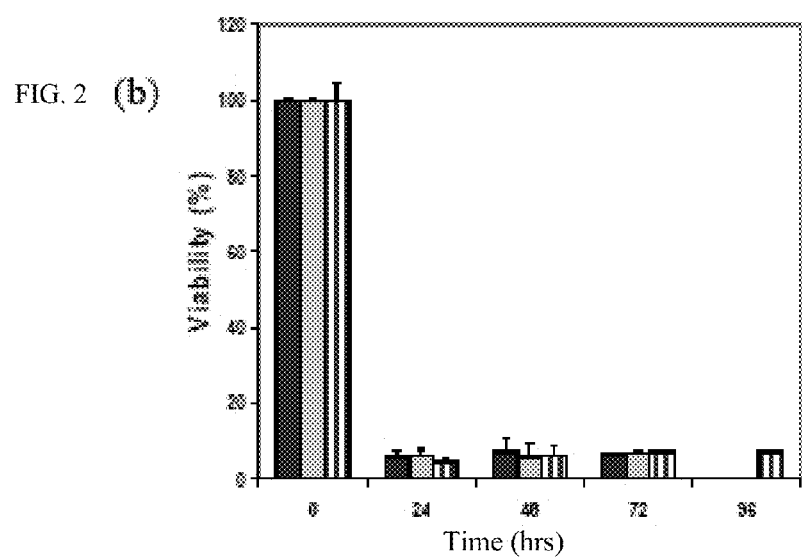
Figure 2:
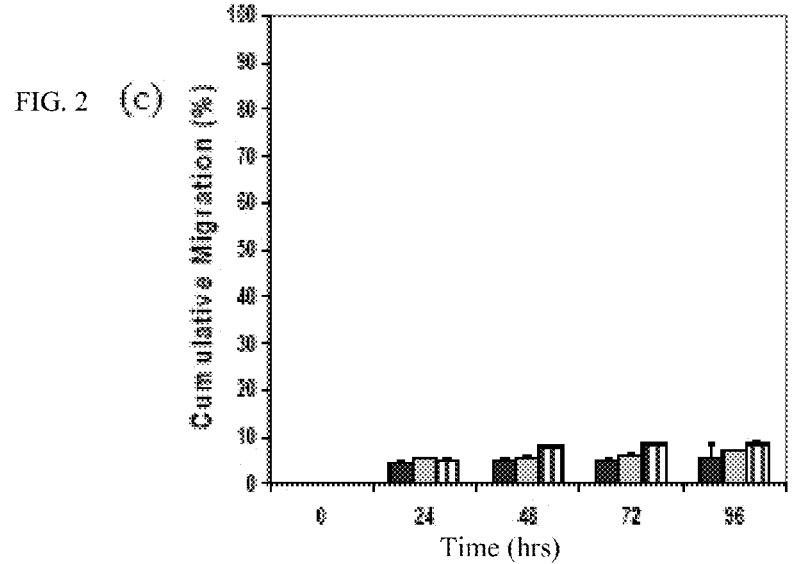

The ability of myoblasts to both remain viable within and migrate from scaffolds without cell adhesion peptides was first tested by seeding myoblasts in scaffolds under the following three conditions: nanoporous alginate scaffolds, nanoporous scaffolds releasing HGF, and microporous scaffolds releasing HGF. Approximately ⅓ of incorporated HGF was released in the first 10 hours, and a sustained release was observed for the following time period (FIG. 2a). The percentage of cells that maintained viability over the first 24 hours was less than 10% under all conditions (FIG. 2B). By 96 hours, a small percentage of viable cells could only be measured in microporous scaffolds releasing HGF. Consistent with the cell loss was the minimal migration of myoblasts from the scaffolds (FIG. 2C). Over the first 24 hours, less than 5% of the total incorporated cells migrated from the scaffolds in any of these conditions. This increased slightly by day two in the microporous scaffolds, but failed to further improve in any condition.

Figure 3:
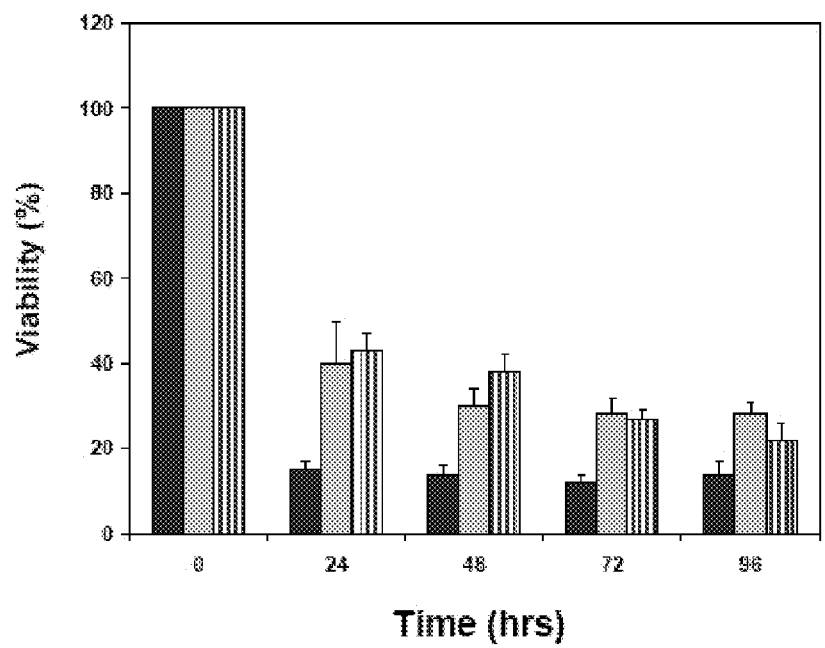
FIGS. 3A and 3B are bar graphs showing cell condition and performance. Viability (FIG. 3A) and cumulative migration (FIG. 3B) is enhanced by peptide modification of alginate. Bars represent nanoporous alginate scaffolds (■), nanoporous scaffolds with HGFG release (▨) and microporous scaffolds with HGF release (▥). Numbers represent mean and SD (n=8). * indicates statistically significant difference as compared to non-HGFG releasing scaffolds p<0.001.
Figure 3:
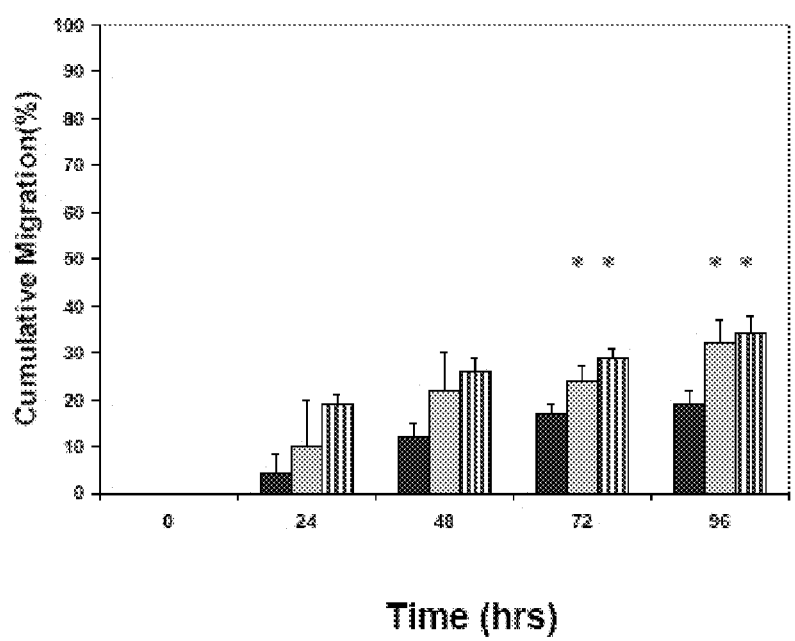

Covalent modification of alginate with adhesion oligopeptides prior to scaffold fabrication improved both the viability of cells, as well as their outward migration (FIGS. 3A-B). Myoblasts seeded in nanoporous, peptide-modified scaffolds demonstrated a two-fold increase in cell viability at 24 hours, as compared to cells in similar non-peptide modified scaffolds. HGF release further increased viability to 40%, and cells seeded in peptide-modified microporous scaffolds with HGF release demonstrated a similar viability (FIG. 3A). However, the viability decreased in all conditions over time. Similarly, cumulative migration was enhanced by peptide modification in concert with HGF release and microporosity. Peptide-modified nanoporous scaffolds led to approximately 20% of seeded cells migrating out of the scaffolds (FIG. 3B). Release of HGF by itself, and in combination with micropores led to an approximately 4-fold increase in cell migration over non peptide-modified nanoporous scaffolds (FIG. 3B). In those conditions, 40% of the seeded cells migrated from the scaffolds, and were available to fuse with host muscle fibers.

Macroporous Alginate and FGF2 Release

Figure 4:
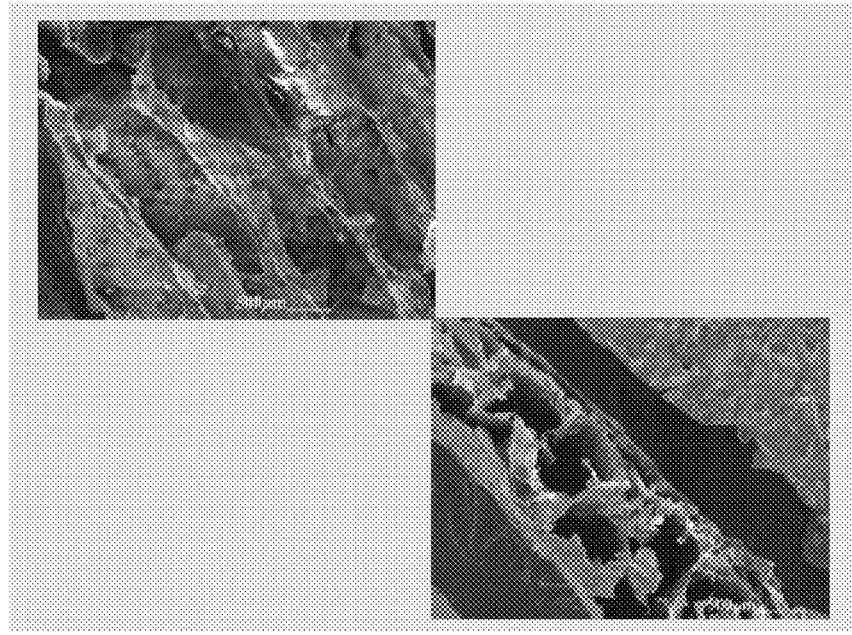
FIG. 4A is a scanning electron microscope (SEM) photomicrographs of side and end views of peptide modified macroporous alginate and FIG. 4B is a line graph showing release kinetics of FGF2. Values represent mean and SD (n=4).
Figure 4:
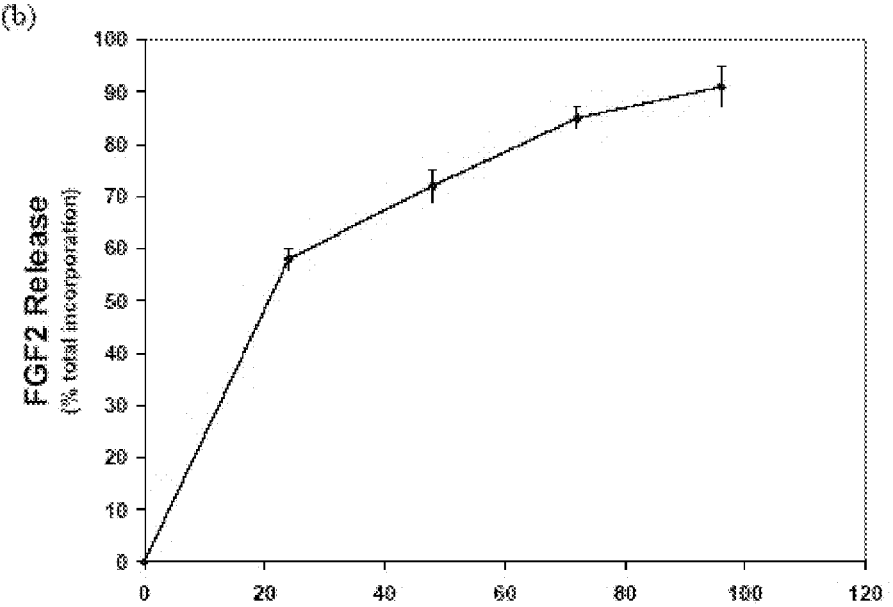
Figure 5:
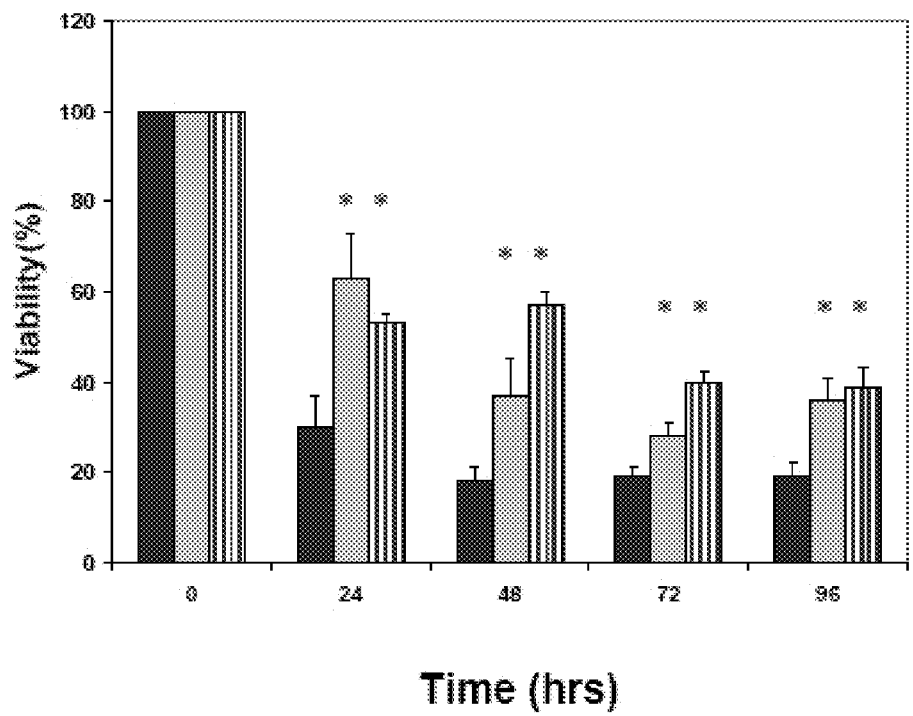
FIG. 5A is a bar graph showing Cell viability and FIG. 5B is a bar graph showing that migration is enhanced by macroporosity and FGF2 release from peptide modified alginate scaffolds. Bars represent macroporous alginate (■), macroporous alginate scaffolds releasing HGF (▨) and scaffolds releasing both HGF and FGF2 (▥). Values represent mean values and SD (n=6). * indicates statistically significant differences (p<0.01), as compared to non-HGF releasing conditions.
Figure 5:
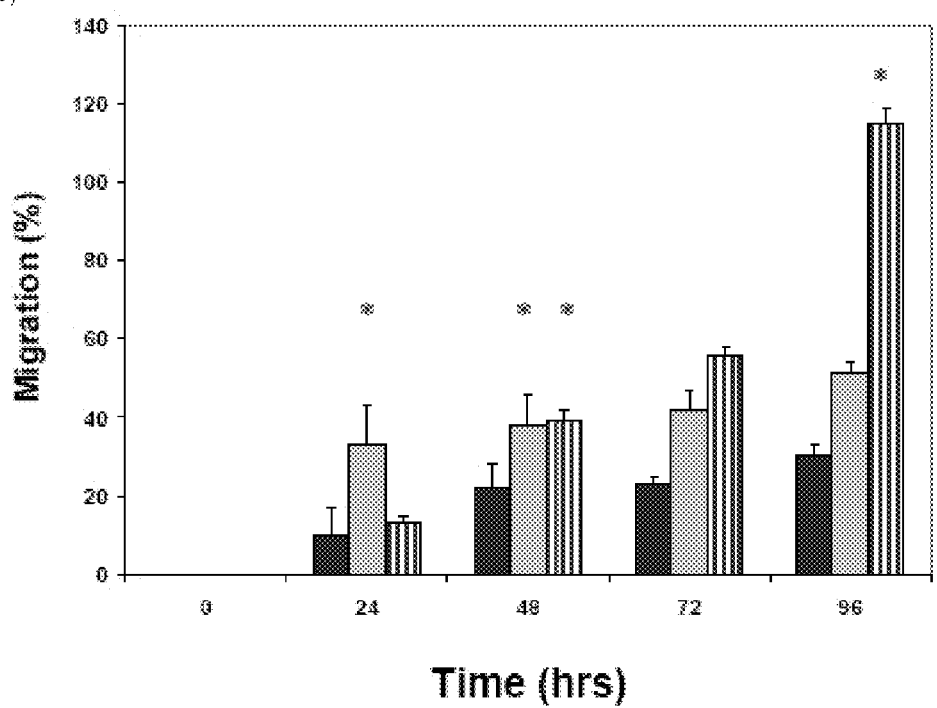

The effects of creating aligned pore channels (macroporous scaffolds; FIG. 4A), and FGF2 release (FIG. 4B) on the viability and outward migration of myoblasts were next examined. Creation of macropores significantly enhanced both the viability and migration of myoblasts (FIGS. 5A-B), as compared to similar micro or nanoporous scaffolds. Release of HGF further increased both survival and migration of myoblasts. The percentage of viable cells under this condition was 63% at 24 hr, and an enhanced viability was maintained through the 96 hr of the experiment (FIG. 5A). Further, release of HGF and FGF2 together led to the greatest level of outward migration (FIG. 5B).

Figure 6:
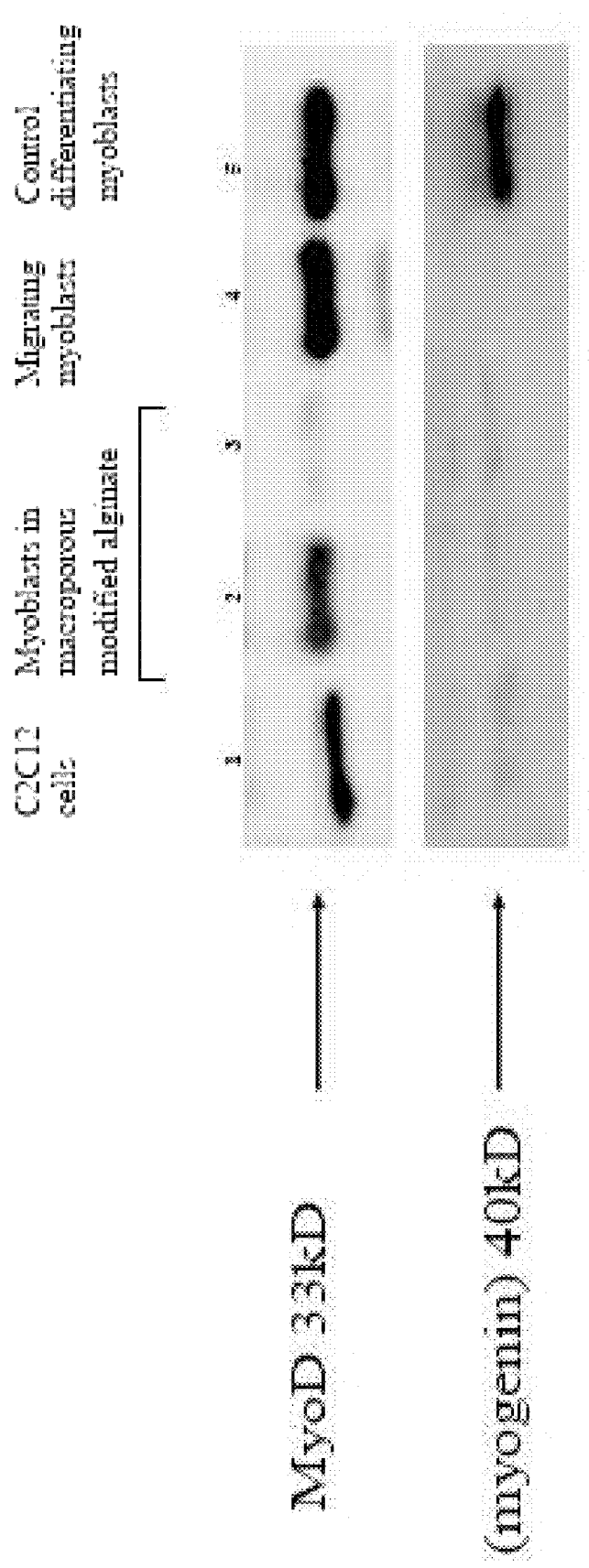
FIG. 6 is a photograph of a Western Blot analysis of cell lysates from myoblasts cultured in macroporous scaffolds fabricated from peptide modified alginate either with (+) (Lane 2) or without (−) (Lane 3) release of HGF and FGF2. Cells migrating from scaffolds were also analyzed (Lane 4). Controls of lysates from C2C12 cell line (Lane 1), and primary myoblasts cultured in standard two dimensional conditions that promote differentiation (Lane 5) are also shown.

Western blot analysis of cell lysates was performed to determine the differentiation state of cells within and migrating from these scaffolds. Cells present in or migrating from scaffolds releasing HGF and FGF2 expressed high levels of MyoD (FIG. 6). Cells present in scaffolds without peptide modification nor HGF/FGF2 did not express significant levels of MyoD. In contrast, neither cells within any of the scaffolds, nor those that migrated from the scaffolds expressed myogenin, a transcription factor associated with end stage differentiation of myogenic cells (FIG. 6).

Enhanced Myocyte Survival and Migration to Target Tissues

The viability and ability of myoblasts to migrate from transplanted scaffolds was found to be strongly regulated by the presence of cell adhesion ligands associated with the scaffold material, the pore structure, and release of growth factors from the material.

Incorporation of myoblasts into scaffolds lacking cell adhesion ligands led to rapid and severe loss of viability, and cell migration was minimal. However, modification of alginate with a $G_4RGDSP$ peptide increased cell viability and migration.

Alginate modified with a cell adhesion peptide(s) directed cells to adhere to the polymer, proliferate and in the case of myoblasts fuse into myofibrils. Peptides that present motifs found in fibronectin, (e.g., RGD) are especially relevant to skeletal muscle engineering because myoblast adhesion to fibronectin is associated with the early proliferative phase of myogenesis. The RGD peptide provided a signal for migration of myoblasts out of the scaffolds; however, additional features of the scaffold in combination with the RGD signal yielded move robust migration. Alignment of macropores in the scaffolds led to a higher cell survival at later time points, and most importantly, a very efficient migration of cells out of the scaffolds. Macroporosity was important for the migration of cells, and smooth muscle cells have been demonstrated to grow most favorably on scaffolds with larger pores.

Incorporation of growth factors known, e.g., HGF and FGF in the case of myoblasts, significantly increased the viability and migration of seeded myoblasts under all variations of scaffold chemistry and architecture. FGF's were the first growth factors shown to have an effect on myogenic cells, and the FGF2 effect on myogenic cells is enhanced by the addition of HGF. In addition, myogenic repair in a muscle crush injury was hindered by the injection of FGF2 antibodies. These data indicate an important physiological role for FGF2, and a role for combined FGF2 and HGF signaling in skeletal muscle regeneration. However, injection of FGF2 into skeletal muscle after injury did not enhance muscle repair, suggesting the importance of using this factor in the proper context. In particular, in the current approach to regenerate skeletal muscle, myogenic cells must be directed to bypass their normal tendency to differentiate, and remain in a proliferative phase until a sufficient number of cells is attained to regenerate the tissue, and the cells have also migrated from the scaffold. FGF2 is particularly useful in preventing the premature differentiation of the transplanted cells, while the migration-inducing effects of HGF provide the latter function.

These results indicate that scaffolds for transplanted cells can be optimized and designed for any phenotype to maintain cell viability and promote migration out of the vehicle. Appropriate combinations of scaffold architecture, adhesion ligands that maintain viability and allow migration, and growth factors that regulate phenotype are used in combination to obtain complex control over the fate of the transplanted cells.

Activation of Transplanted Cells for Muscle Regeneration

Macroporous alginate scaffolds were designed to serve as a micorenvironment for transplanted muscle progenitor cells (satellite cells) at a muscle laceration site. By releasing factors that promote activation and migration (hepatocyte growth factor and fibroblast growth factor 2), but not terminal differentiation of satellite cells, cells competent to participate in regeneration of damaged host tissues are released in a sustained manner, effectively using the scaffold as a niche to sustain a pool of progenitor cells for regeneration of muscle fibers.

In vivo studies were carried out using C57B1/6J mice in which the tibialis anterior muscle was completely lacerated at the midline of the muscle. Following laceration, the muscle ends were sutured together using non-resorbable sutures, and scaffolds containing combinations of growth factors and cells were placed on top of the injury. Muscle regeneration was assayed at 30 days.

Explanted tissues show largest area of new tissue formation when treated with scaffolds containing cells and both growth factors as quantified by muscle mass and decrease in defect area.

Morphological analysis of regenerated muscle fibers showed increased fiber diameter and an increase in the number of centrally located nuclei in animals treated with scaffolds containing growth factors and cells, as compared to all other sample types.

Transplantation of myoblasts derived from transgenic Rosa 26 mice that contain the β-galactosideae gene allows for observation of incorporation of transplanted cells into regenerating host tissue. Transplanting cells on scaffolds containing growth factors increases grafting of transplanted cells into regenerating fibers as compared to injection of cells without a scaffold or growth factors.

Example 2

Niche Scaffolds Promote Muscle Regeneration Using Transplanted Cells

Transplanting myoblasts within synthetic niches that maintain viability, prevent terminal differentiation, and promote outward migration significantly enhances their repopulation and regeneration of damaged host muscle. Myoblasts were expanded in culture, and delivered to tibialis anterior muscle laceration sites in mice by direct injection into muscle, transplantation on a macroporous delivery vehicle releasing factors that induce myoblast activation and migration (HGF and FGF), or transplantation on materials lacking factor release. Controls included the implantation of blank scaffolds, and scaffolds releasing factors without cells. Injected cells in the absence of a scaffold demonstrated a limited repopulation of damaged muscle, and led to a slight improvement in muscle regeneration. Delivery of cells on scaffolds that did not promote migration resulted in no improvement in muscle regeneration. Strikingly, delivery of cells on scaffolds which promoted myoblast activation and migration led to extensive repopulation of host muscle tissue, increased the regeneration of muscle fibers, and led to a higher overall mass of the injured muscle. This strategy for cell transplantation significantly enhance muscle regeneration from transplanted cells, and is broadly applicable to the various tissues and organ systems.

The scaffolds described herein are not intended to guide tissue formation around the scaffold, but in contrast, maintain the viability of passenger cells while simultaneously encouraging and directing their outward migration to repopulate the surrounding host damaged tissue and to enhance its regeneration. The scaffold serves a function analogous to the special tissue microenvironments, termed niches, that maintain the potential of stem cell populations while allowing the daughter cells to migrate and attain specialized functions distant to the niche. The physical and chemical aspects of the scaffold to successfully promote host tissue repopulation and simultaneously prevent the premature terminal differentiation of precursor cells.

Scaffolds were designed to promote myoblast survival, migration, and prevent terminal differentiation to enhance repopulation of injured muscle from transplanted myoblasts. As described above, HGF and FGF2 release from macroporous scaffolds fabricated from RGD-presenting alginate polymers significantly enhanced the viability of satellite cells cultured in the scaffolds in vitro, and that HGF and FGF2 worked additively to promote outward migration of the seeded cells while preventing terminal differentiation in the scaffold. An in vitro muscle laceration model was used to recapitulate injuries common in athletes and in trauma. This model is an accurate and reliable model of human injury. Some other mouse studies has been criticized in part due to the indirect relation of the models (irradiation, injection of cardiotoxin, or cryoinjury) to human injuries or disease. Further, to determine the participation of donor versus host myoblasts in muscle regeneration, donor myoblasts were obtained from Rosa26 mice to allow identification by their over-expression of β-galactosidase.

Scaffold Preparation

Ultra pure MVG alginate powder (Pronova, Oslo Norway) was irradiated with a cobalt-60 source for 4 hours at a γ-dose of 5.0 Mrad (Phoenix Lab, University of Michigan, Ann Arbor, USA to produce low molecular weight alginate ($M_w=5.3\times10^4$ g/mol). Alginates were further modified with covalently conjugated oligopeptides with a sequence of G$_4$RGDSP (Commonwealth Biotechnology Inc.) at an average density of 3.4 mM peptide/mole of alginate monomer, using carbodiimide chemistry. High molecular weight ultra-pure alginate (MVG, Pronova, $M_w=2.7\times10^5$ g/mol) was also covalently modified with this oligopeptide.

To fabricate alginate scaffolds that were highly porous, molds (2 mm×5 mm×5 mm) were constructed from polyvinylsulfoxane (PVS) (Kerr). Porogens were constructed from size 14 stainless steel orthodontic straight wire cut to 10 mm lengths. The orthodontic wire was aligned in two sets of parallel rows 500 μm apart, sterilized and placed in the scaffold mold. A solution containing equal concentrations of irradiated low molecular weight (1%, w:v) and non-irradiated high molecular weight modified alginate (1%, w:v) was prepared in calcium free DMEM (Invitrogen). HGF (Santa Cruz Biotechnologies, CA.), and FGF2 (B&D) were added to the alginate solution (final concentrations 100 ng/ml). A calcium sulfate slurry (0.41 g CaSO$_4$/ml dd H$_2$0) (Aldrich), was added at a ratio of 40 μl CaSO$_4$/1 ml alginate and vigorously mixed. The resulting solution was immediately expressed into the PVS mold containing the wire porogens. A sterile glass plate was placed over the mold, and after the alginate has completely gelled (30 minutes), the gel containing the wire porogens was carefully lifted from the PVS mold and placed in a 100 cm$^3$ petri dish. To produce macroporous scaffolds with open, interconnected pores, the gels were cooled to −70° C., the wire porogens were carefully removed, and the gels were lyophilized and stored at −20° C. until needed.

Cell Culture and Seeding

Four month old B6.12957-Gt(ROSA)26Sor/J (Jackson Laboratory, Bar Harbor Me.) were sacrificed and the satellite cells were isolated from hind limbs. Hind limb skeletal musculature was surgically excised, finely minced and disassociated in 0.02% Trypsin (GIBCO) and 2% Collagenase type 4 (Worthington Biochemical, Lakewood, N.J.) for 60 minutes at 37° C./5% CO$_2$ while agitating on an orbital shaker. Disassociated muscle was strained in a 70 μm sieve, centrifuged at 1600 rpm for 5 min. and resuspended in 10 ml high glucose DMEM, supplemented with pyruvate (GIBCO). Media was further supplemented with 10% fetal bovine serum and 1% penicillin/streptomycin (GIBCO). Resuspended cells were plated in 75 cm$^3$ tissue culture flasks (Fisher), and HGF (50 ng/ml) and FGF2 (50 ng/ml) were added to the medium. After seven days, cultures were passaged and purified satellite cell suspensions were obtained via percoll fractionation. Purified cultures were incubated for seven days at 37° C. until 80% confluent and then were collected via trypsinization and seeded at $10^7$ cells/ml onto modified open pore alginate scaffolds.

Surgical Procedure and Analysis

Four week old C57BL/6 mice were anesthetized via intraperitoneal injection of ketamine (0.5 ml/kg) and xylazine (0.25 ml/kg). Bilateral incisions were made to expose the tibialis anterior muscle of both hindlimbs. Once exposed, the muscle was completely lacerated at the midlength ventral-dorsally. The proximal ends of the lacerated muscle were then closed using a #4 black silk continuous suture, and scaffolds were placed over the wound or myoblasts injected into the muscle. In all conditions utilizing myoblast transplantation, a total of $5 \times 10^5$ cells was delivered. The surgical site was closed with #4 black silk interrupted suture and the surgical site was left undisturbed until the muscle was retrieved at 10 or 30 days.

Tibialis anterior muscle was excised and fixed in 4% paraformaldehyde for 2 hr and rinsed for 1 hr in PBS. Whole muscle was then incubated overnight infi-galactosidase staining solution containing 25 µl/ml Xgal stock solution. The muscle was paraffin embedded, cut into serial sections (5 µm thick) and placed on glass slides for histological analysis. Sections were deparaffinized through descending series of EtOH and rehydrated in $H_2O$ and washed for 5 minutes in 3% $H_2O_2$ (Sigma) in PBS to quench any endogenous peroxidase activity. Sections were stained with Gill's 3 hematoxylin (Sigma) and aqueous eosin solution (Sigma) to visualize tissue morphology. Finally, serial sections were incubated with a monoclonal antifi-galactosidase antibody (1:1000), (Chemicon, Temecula Calif.) for one hour and then incubated with a HRP-conjugated secondary antibody (1:1000) (Dako-Cytomation, Carpinteria, Calif.). Samples were rinsed, and mounted with Permount (Fisher, Fairlawn, N.J.).

Defect size analysis was performed using Adobe Photoshop and Image Pro Plus software. High powered (100×) images were obtained using a Leica CTR 5000 light microscope and Open Lab software (Improvision). Six samples were analyzed for each condition. Areas of muscle defect were identified in hematoxylin and eosin (H&E) stained sections via their lack of organized muscle fibers. Fiber size and nuclei number were determined via high powered microscopic analysis of ten random fields of regenerating muscle fibers adjacent to the muscle defect. Only centrally located nuclei, a hallmark of regenerating muscle fibers, were counted in the quantification of number of nuclei.

Statistically significant differences were determined using two tailed students t-test. Statistical significance was defined by $p<0.05$. All data was plotted as the mean+/−standard deviation of the mean (SD).

Repopulation of Muscle Tissue with Transplanted Cells

Figure 7:
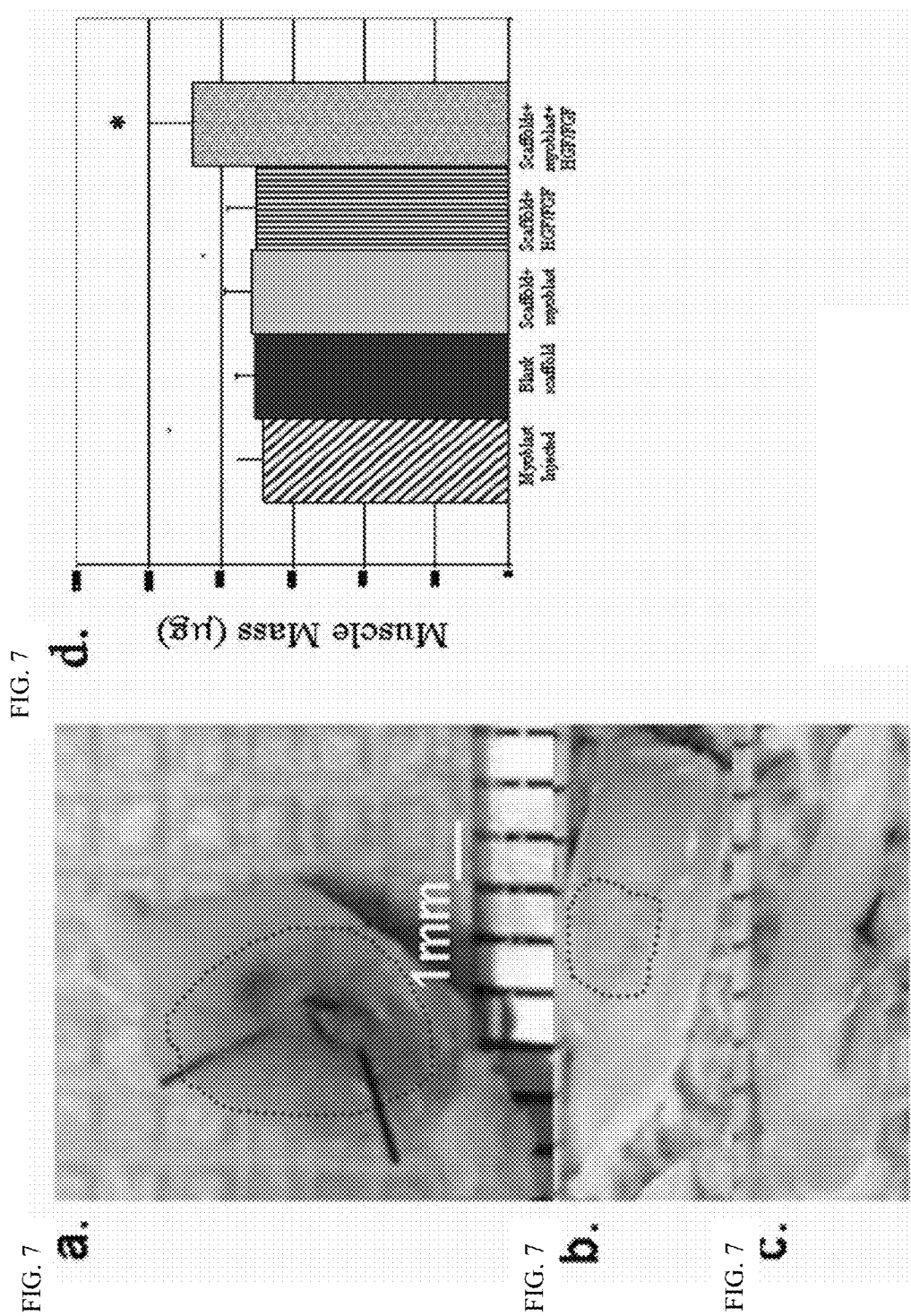
FIGS. 7A-7C are photographs of tibialis anterior muscles treated with scaffolds delivering cells and releasing HGF and FGF2 (FIG. 7A), scaffolds containing only HGF and FGF2 (FIG. 7B), and scaffolds containing only myoblasts (FIG. 7C). Muscles were stained to allow gross identification of regions containing lac Z donor cells (dotted lines outline positively stained tissue). Size bars are shown on the photomicrographs.
FIG. 7D is a bar graph showing that the mass of the muscle at 30 days post injury was greater when treated with scaffolds containing myoblasts and HGF and FGF2 (HGF/FGF2-cells in scaffold) compared to injuries treated with an injection of myoblasts directly into the muscle (cells [injected]), blank scaffolds, scaffolds releasing growth factors without cells (HGF/FGF), or cells transplanted in scaffolds not releasing growth factors (cells in scaffold). Values represent mean and standard deviation (n=6). * represents statistically significant difference (p<0.001) compared to all other conditions.

The tibialis muscle of each mouse was lacerated and the laceration was subsequently closed with suture. One of five conditions was used to treat the laceration site: 1) myoblasts were directly injected into the muscle at the laceration site, 2) blank scaffolds were placed over the laceration, 3) scaffolds seeded with myoblasts were placed over the laceration, 4) scaffolds releasing HGF and FGF2 (− cells) were placed over the laceration, and 5) scaffolds containing myoblasts and releasing HGF and FGF2 were placed. The implants were placed without the aid of any adhesive or glue, and upon retrieval at 10 and 30 days, 80% of the implants were in the same location as the day of surgery. The implants were attached to the injury site and the overlying epidermis by fascia like tissue. A gross difference in the size of injured muscle treated with scaffolds containing growth factors and myoblasts, as compared to all other conditions, was observed at 30 days, as these muscles were larger in every dimension than the other conditions tested (FIGS. 7A-C). Quantification of the mass of these muscles revealed a statistically significant 30% increase in mass, as compared to the other conditions (FIG. 7D). Gross observation also revealed that β-galactosidase activity, as indicated by lacZ staining, was noticeably more intense in muscles treated with the scaffolds containing myoblasts and growth factors (FIG. 7A) than in the other conditions in which myoblasts were transplanted, indicating a greater repopulation of the native muscle by cells transplanted in this condition.

Analysis of tissue sections revealed a defect at 10 days that appeared largely necrotic in all conditions (FIGS. 8A-E). No normal muscle tissue appeared within the defect at this early time point. The defect was filled with cellular debris, blood and basophilic cells. There were no myofibers that spanned the defect area. The muscle fibers that lined the borders of the defect were largely disorganized and contained centrally located nuclei. The muscle injury treated with a localized sustained delivery of growth factors alone had a larger remaining defect area than any other condition at this timepoint, although this difference was only statistically significant when compared to the injury treated with sustained delivery of both myoblasts and growth factors. When sections from muscle defects treated with myoblast transplantation were viewed under high power magnification, there were no gross differences observed in the number of lacZ (+) cells present in the tissue at this time.

Figure 8:
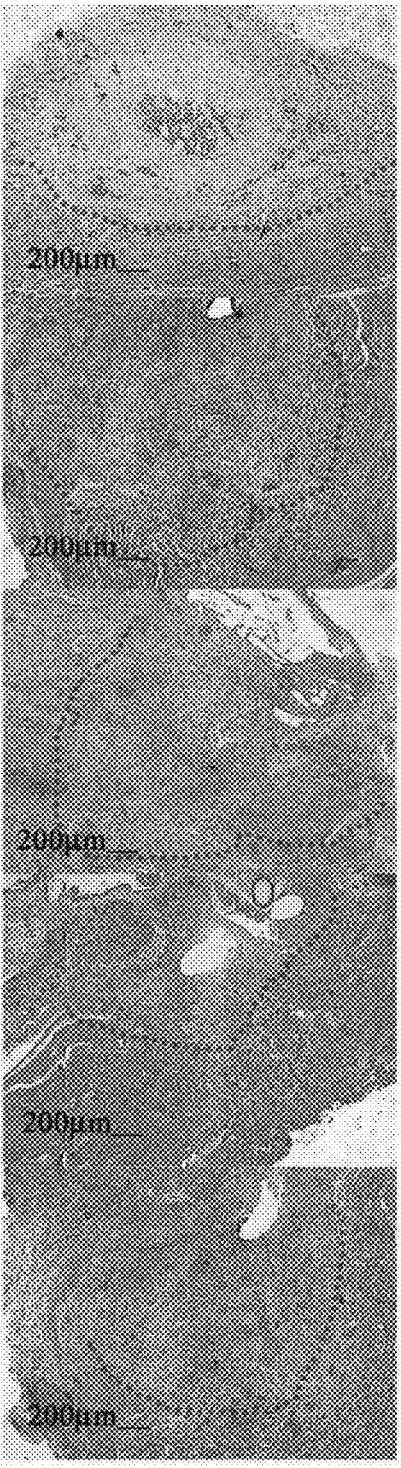
FIGS. 8A-J are photomicrographs of defects 10 days post injury (FIGS. 8A-E), and defects 30 days post injury (FIGS. 8F-J). Conditions included injuries treated with an injection of myoblasts directly into the muscle (FIGS. 8A, F), blank scaffolds (FIGS. 8B, G), scaffolds releasing growth factors without cells (Figs. C, H), cells transplanted in scaffolds not releasing growth factors (FIGS. 8D, I), and scaffolds delivering myoblasts and HGF and FGF2 (FIGS. 8E, J). Defects are outlined with dotted lines. At ten days, defects were unresolved and filled with necrotic debris in all conditions. At 30 days, the laceration injuries began to resolve in all conditions, but myoblasts delivered on scaffolds in combination with growth factors led to virtually complete resolution of the defect at this time point. Size bars are shown on the photomicrographs.
Figure 9:
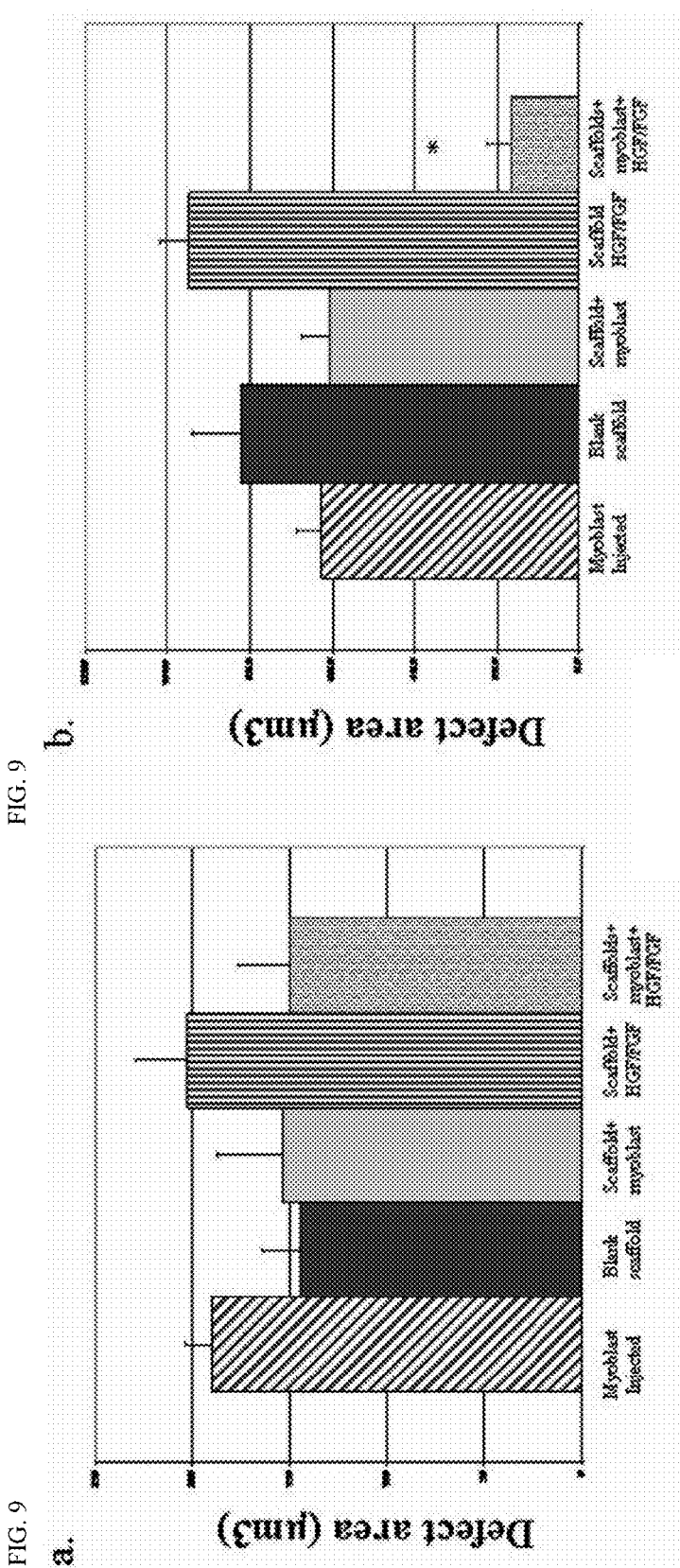
FIGS. 9A-B are bar graphs showing quantitative analysis of remaining defect area 10 days post injury (FIG. 9A), and 30 days post injury (FIG. 9B). Conditions included an injection of myoblasts directly into the muscle (cells[injected]), blank scaffolds, scaffolds releasing growth factors without cells (HGF/FGF), cells transplanted in scaffolds not releasing growth factors (cells in scaffold), and scaffolds delivering myoblasts and HGF and FGF2 (HGF/FGF2-cells in scaffold). No significant resolution of the defects occurred in any condition at 10 days. In contrast, at 30 days post injury the defects in muscles treated with scaffolds delivering cells and growth factors were significantly smaller than in any other condition (* indicates p<0.05, as compared to all other conditions). A less pronounced, but still significant reduction in defect size was also seen in muscles treated with injected cells or scaffolds delivering HGF and FGF2 (# indicates p<0.01 compared to blank scaffolds or cells transplanted on scaffolds not releasing growth factors). Values represent mean and standard deviation (n=6).

In contrast to the early results, the defects in the muscles treated with sustained localized delivery of myoblasts and growth factors were largely resolved at 30 days (FIG. 8J). In many of these animals, the only remaining defect was that caused by the closing suture. In addition there were few areas of fat deposit and virtually no scar tissue at this time point. The unresolved defect areas in the other experimental conditions had also decreased in size (FIGS. 8F-I), as compared to the defect area at 10 days, but were still much larger than the cell/HGF and FGF2 delivery condition. In addition, scar tissue or fat deposits were apparent in these other conditions. When the areas of unresolved defects were quantified, there were no statistically significant differences between the conditions at 10 days (FIG. 9A). However, at 30 days post injury the defects in muscles treated with scaffolds delivering cells and growth factors were significantly smaller than in any other condition (FIG. 9B). A lesser reduction in defect size was also seen in muscles treated with injected cells or scaffolds delivering HGF and FGF2.

To further analyze muscle regeneration, the mean width of regenerated myofibers and number of post mitotic centrally located nuclei per length of myofiber in the region proximal to the resolving muscle defects were quantified via high powered light microscopic analysis. The mean width of regenerating fibers and density of centrally located nuclei were qualitatively greater in muscles treated with scaffold delivery of cells and growth factors (FIG. 10B), as compared to scaffolds delivering only growth factors (FIG. 10A), or any other experimental condition. Determination of the mean width of fibers 30 days post injury confirmed that muscles treated with myoblasts in combination with growth factors exhibited a 3 fold increase in fiber size as compared to the blank scaffolds, injected cells, or cells transplanted alone in scaffolds (FIG. 10C). The fiber width also increased in the experimental group involving HGF and FGF2 delivery, but not as dramatically. In addition, the muscle fibers in the injury group treated with myoblasts and growth factors via scaffold delivery contained 30% more centrally located nuclei than any other conditions at 30 days post injury (FIG. 10D), indicating more fusion of myoblasts into the fibers, which supports the finding that these fibers were larger in size.

Figure 11:
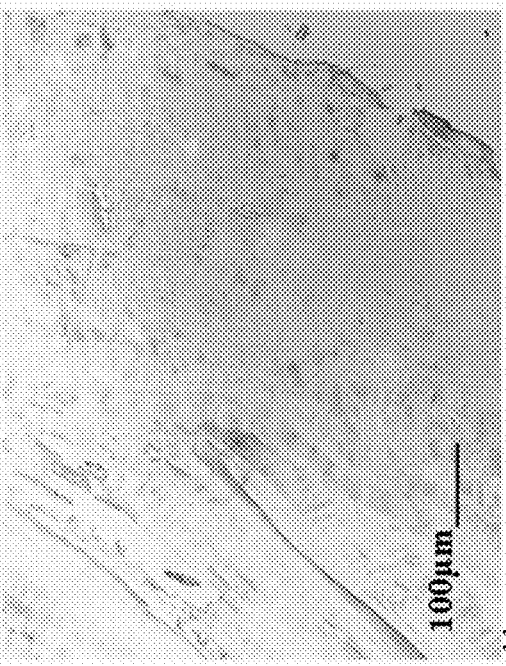
FIGS. 11A-D are photomicrographs of muscel tissue. Photomicrographs at low power (FIGS. 11A-B), and high power (FIGS. 11C-D) of tissue sections were immunostained to identify donor myoblasts (positive staining for β-galactocidase) in the regenerating tissues. Injection of cells (FIGS. 11B, D) led to minimal donor cell incorporation into host musculature. In contrast, transplantation of cells on scaffolds releasing growth factors leads to extensive incorporation of donor cells into the regenerating muscle tissue (FIGS. 11A, C). Size bars are shown on the photomicrographs.
Figure 11:
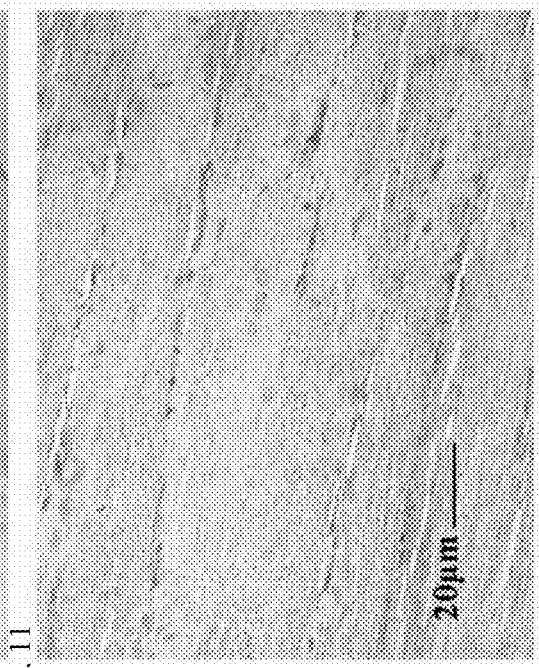
Figure 11:
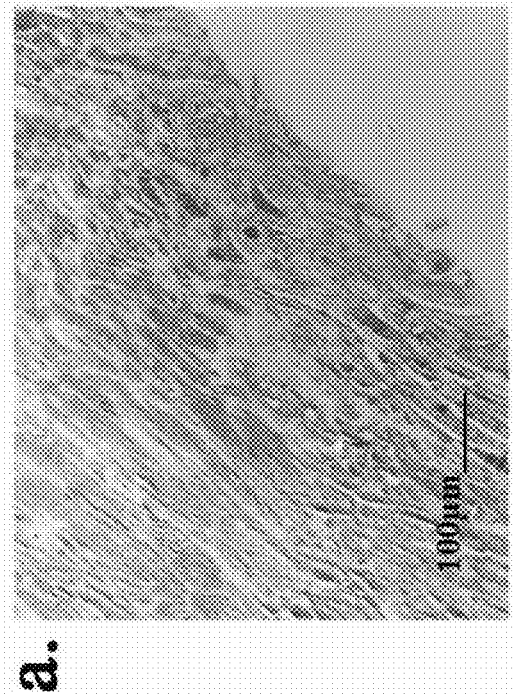
Figure 11:
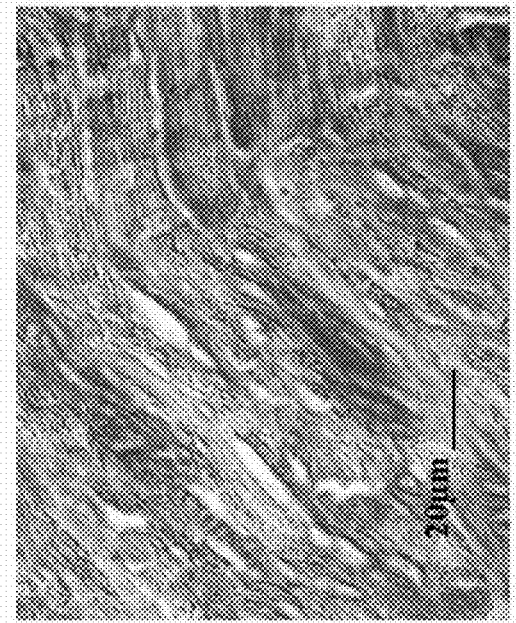

Finally, immunostaining of tissue sections from the tibialis anterior muscle 30 day post-injury revealed that the increases in the muscle size, fiber width, and fiber nuclei were accompanied by robust engraftment of transplanted myoblasts into host regenerating muscle, when cells were transplanted on scaffolds releasing HGF/FGF2 (FIG. 11A, C). A more limited number of engrafted donor cells were noted in the condition using direct myoblast injection (FIG. 11B, D). No LacZ (+) cells were noted in the other experimental and control conditions.

Modulation of skeletal muscle regeneration, subsequent to injury, by myoblast transplantation requires the survival of donor myoblasts and their stable incorporation into muscle fibers within the host tissue. Transplantation of myoblasts on scaffolds that promote their outward migration combines the advantages of host muscle fiber regeneration obtained with direct cell injection with the control over transplanted cell fate made possible with the use of cell-instructive scaffolds. Direct injection of myoblasts into injured muscles enhances regeneration, as does localized delivery of HGF and FGF2 in combination from a scaffold, but transplanting the cells from a scaffold that simultaneously delivers HGF and FGF2 dramatically enhanced the participation of transplanted cells in muscle regeneration and the overall extent of regeneration.

Transplantation of myoblasts via direct injection, and delivery with a scaffold not releasing growth factors led to distinct outcomes in the model system. Injection of myoblasts alone enhanced muscle regeneration, although to a modest extent. The injected cells participated in muscle fiber formation, as evidenced by identification of Rosa26-derived cells in the defect site, decreased mean defect size at 30 days, and increased skeletal muscle fiber width. In contrast, transplantation of the same cell number on the scaffolds without growth factor release led to no detectable changes in muscle regeneration, as compared to implantation of blank scaffolds at the defect site. Cell migration out of scaffolds is low in the absence of the activating effects of HGF and FGF2 (20-30% of seeded cells migrate from scaffolds over 4 days in vitro) and those scaffolds provide few cells to the surrounding tissue that can participate in regeneration compared to the HGF/FGF2 scaffolds.

Delivery of a combination of HGF and FGF2 from the scaffolds, in the absence of transplanted cells, had a modest effect on muscle regeneration. The width of regenerating fibers was increased in this condition, as compared to blank scaffolds, and the number of centrally located nuclei in these fibers, a hallmark of regenerating myofibers was increased as well. These effects were consistent with the modest decrease in defect area noted at 30 days. Other studies of local HGF and FGF2 delivery to sites of muscle regeneration have led to results distinct from those reported herein. Local HGF delivery has been previously documented to increase the number of activated myoblasts within injured muscle, consistent with its role in activating satellite cells, but repeated presentation of HGF actually inhibited regeneration. Miller et al., 200 *Am. J. Physiol. Cell. Physiol.* 278: C174-181. The high dose of HGF may have retarded the ability of host myoblasts to withdraw from the cell cycle and terminally differentiate. In addition, application of endogenous FGF2 had been previously reported to not enhance muscle regeneration. In contrast to those previous studies, the scaffolds described herein delivered small quantities of the factors (e.g., 5 ng), continually released the factors over an extended time period, e.g., 3-10 days, delivered a combination of the two factors rather than a single factor, and the type of muscle injury was also different from previous systems. The model system used to generate the foregoing data more closely resembles a human injury or muscle defect compared to the earlier studies.

Transplanting myoblasts on a scaffold that released HGF and FGF2 significantly enhanced muscle regeneration by every measure examined. The number of transplanted cells participating in muscle regeneration, as indicated by immunohistochemical staining for $\beta$-galactosidase, dramatically increased. The width of regenerating fibers was significantly enhanced, as was the number of centrally located nuclei in the fibers, which are both consistent with an increased number of myoblasts participating in muscle formation. The enhanced regeneration led to almost complete resolution of the injury defect by 30 days, and to a significant recovery of muscle mass following the atrophy induced by the injury. Cells placed in these growth factor releasing scaffolds very efficiently migrate out from the scaffolds in vitro (100% migration in 4 days), and the growth factor release maintains the cells in an activated, proliferating, but non-differentiated state (myoD positive, myogenin negative) in the scaffold. Prior to the invention, myoblasts injected into muscle had poor survival due to the lack of an adhesion substrate and the inflammatory environment present in the injury. Transplantation of cells in scaffolds maintains the viability of the transplanted cells, while protecting them from the inflammatory environment. Activation of myoblasts by exposure to HGF and FGF2 also increases their migration and proliferation, and thus enhances their ability to populate host musculature. The increase in muscle mass, muscle fiber size and the number of myonuclei per fiber, resemble the normal regeneration of muscle tissue associated with healing of muscle lacerations and other defects of muscular tissue (e.g., applications ranging from hematopoietic system reconstitution to neural regeneration).

Example 3

Treatment Skin Wounds

In the context of a skin defect, the goals of the therapy are dictated by the type of wound (e.g., acute burn, revision of scar, or chronic ulcer) and size of the wound. In the case of a small chronic ulcer, the objective is closure of the wound by regeneration of the dermis. The epidermis regenerates via migration of host keratinocytes from the adjacent epidermis. For large wounds, keratinocytes, optimally autologous, are provided by the device to promote regeneration of the epidermis. Cells are loaded into a scaffold material that is placed directly over the wound site, e.g., a scaffold structure in the form of a bandage. The material provides a stream of appropriate cells to promote regeneration. For dermal regeneration, fibroblasts cells are used to seed the device, and these cells are either autologous (biopsy taken from another location and expanded before transplantation) or allogeneic. Advantages of autologous cells include a decreased risk of disease transmission, and immune acceptance of the cells. However, a time interval of several days to a few weeks would be required after patient biopsy to generate sufficient cells for treatment. Allogeneic cells allow immediate treatment of the patient from a stored bank of cells, and significant reductions in therapy cost. Immunosuppressive agents are optionally co-administered to reduce or prevent rejection of these cells by the patients immune system.

The device design includes one or a combination of the following features: 1. (physical properties) pores that would readily allow cells to migrate out of the device into the underlying tissue; 2. (physical properties) a semipermeable external membrane designed to control fluid loss from the wound, prevent infection, and prevent cell migration out of the device away from the tissue; 3. (adhesion ligands) inclusion of cell adhesion ligands to allow fibroblasts to migrate through and out of the material, e.g., RGD containing peptides; 4. (growth factors) local presentation of FGF2 to induce fibroblast proliferation within the device; 5. (enzymes) the device is designed to allow for the rapid release into the wound of enzymes useful in debriding the wound; 6. (helper cells) if the individual was anticipated to have a limited angiogenic response, endothelial cells or endothelial progenitors are be included in the device, and stimulated to repopulate the wound in concert with the fibroblasts to promote vascularization.

This application utilizes materials with a relatively low elastic modulus, e.g., 0.1-100, 1-100 kPa. Stiff materials would not be suitable, as such materials would not conform to a wound. Hydrogels or elastomeric polymers are useful in this device in order to conform to the wound and provide control over fluid transport, prevent infection, and allow the physical contact required for cells to migrate out of the device into the wound. The hydrogel or other material also has adhesive properties. An adhesive surface permits contact to the wound so the remains fixed, even as the patient moves. Optionally, the device itself is adhesive; alternatively, the device is fixed in place over the wound using an adhesive composition such as a pharmaceutically acceptable tape or glue. A semipermeable outer surface is provided by either using a composite material (e.g., nonporous silicone sheet placed on outer surface of porous device) or processing the device to create anisotropic porosity.

Example 4

Devices and Systems for Promoting Angiogenesis

Angiogenesis is a critical element in any tissue regeneration effort, and the temporally distinct signaling of vascular endothelial growth factor (VEGF) is crucial in this process. Devices that contain compositions which promote angiogenesis together with endothelial cells resulted in a synergistic angiogenic effect. The approach utilizes cells that play a role in the angiogenic process, e.g., endothelial progenitor cells and outgrowth endothelial cells (e.g., derived from cord blood or from peripheral blood samples).

An injectable alginate hydrogel was developed to provide spatial distribution and temporal control of factors inducing neovascularization of hypoxic tissues. The hindlimbs of C57BL/6J mice were made ischemic by femoral artery and vein ligation, and the hydrogel containing growth factors was directly injected into the ischemic muscle (bolus delivery of VEGF was used as a control), and the in vivo release kinetics and distribution of $VEGF_{121}$ and $VEGF_{165}$ were assessed using an ELISA on tissue samples. The gel led to complete return of tissue perfusion to normal levels by day 28, whereas normal levels of perfusion were not achieved with bolus delivery of VEGF.

Several types of stem cells, including endothelial progenitor cells (EPC) cultivated from cord blood are useful in therapeutic angiogenesis. These cell-based therapies present several advantages over protein or gene-based therapies. Co-transplanting endothelial progenitor cells (EPC) and outgrowth endothelial cells (OEC) enhances vascularization compared to transplantation of each cell type alone. These cells are delivered through the intramuscular injection as well as to other tissues in which vascularization is desired. Co-transplantation of EPC and OEC in a synthetic extracellular matrix device, which was specifically designed as a niche to support cell growth and migration led to dramatically improved vascularization at an ischemic site. Microporous alginate-based hydrogels contained synthetic oligopeptides containing the Arg-Gly-Asp sequence (RGD peptides) and vascular endothelial growth factor (VEGF). The RGD peptide supports cell adhesion, growth and migration in the gel matrix and the sustained release of VEGF stimulates cell migration.

Hydrogels were prepared by cross-linking alginate molecules containing covalently bound RGD peptides with calcium ions. VEGF was loaded in the gel matrix by mixing with alginate solution prior to cross-linking. Micro-sized pores in the gel matrix were induced by freezing the gel at −20° C. followed by lyophilization. Human microvascular endothelial cells were seeded into alginate scaffolds and placed into a collagen gel in a 24 well plate. After 3 days of culture, gel was degraded and cell number was quantified.

The mixture of EPC and OEC was loaded into the micropores and transplanted to the ligation site. The femoral artery in the hind limb of SCID mice was ligated and the ends of the artery were tied off with sutures. The recovery of blood perfusion in the right hind limb was evaluated using laser Doppler perfusion imaging (LDPI) system.

Figure 12:
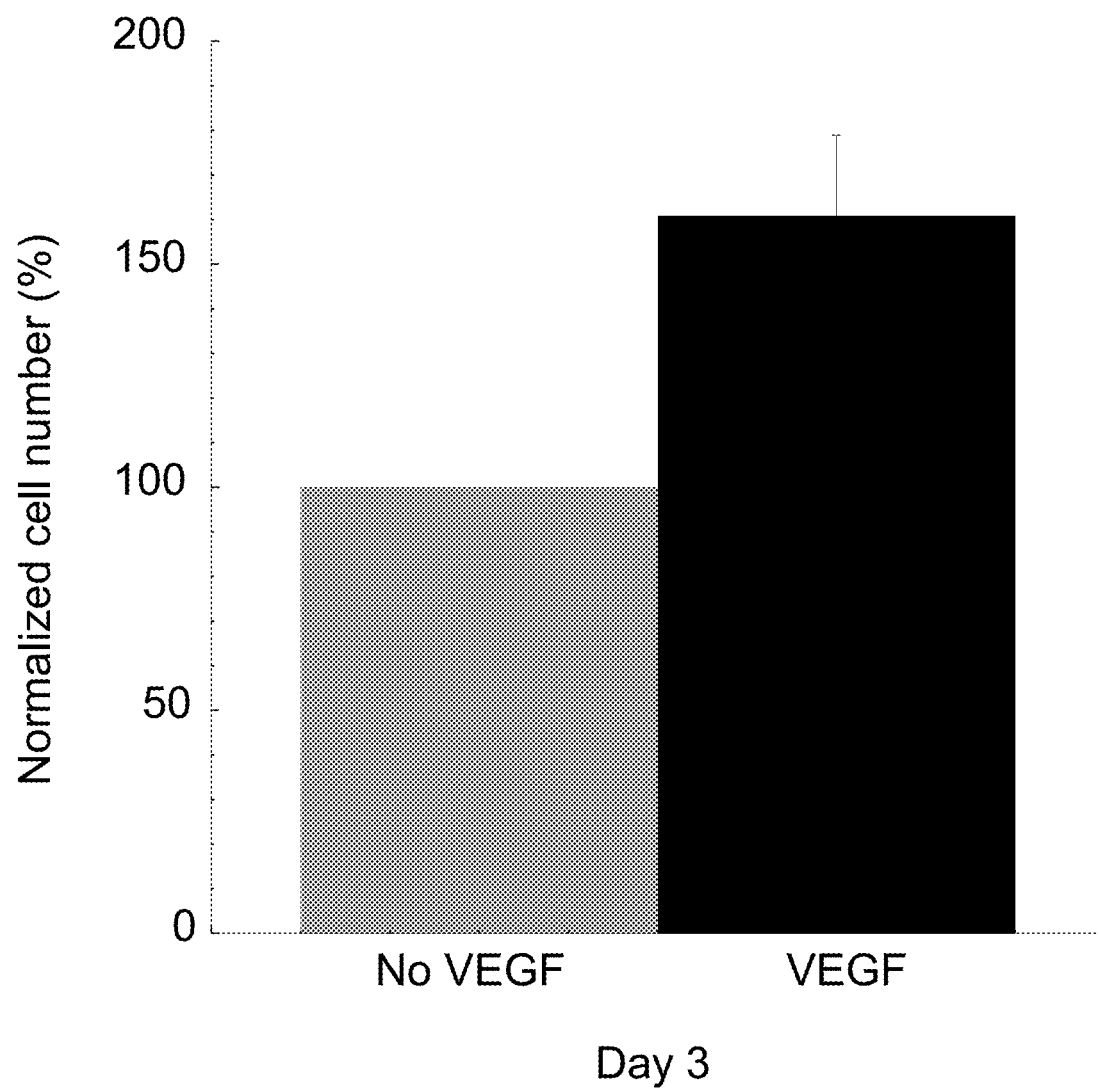
FIG. 12 is a bar graph showing endothelial cell migration out of alginate gel scaffolds that contain VEGF compared to scaffolds without VEGF.
Figure 13A:
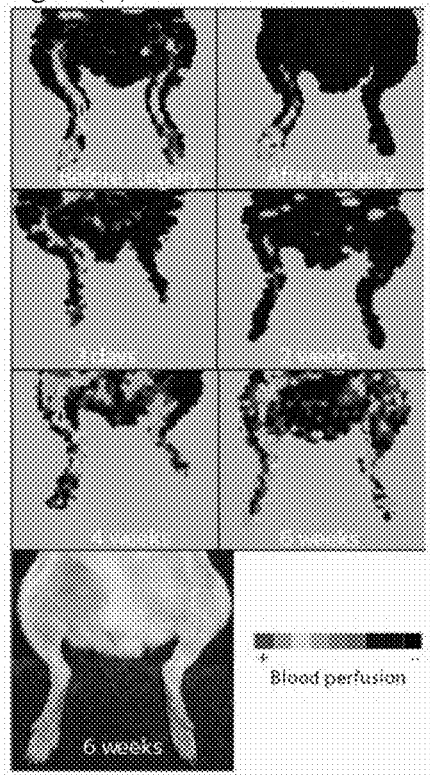
FIGS. 13A-B are photographs of mouse hindlimbs showing blood perfusion before and after surgery. Transplanting cells within the gel matrix enhanced the recovery of blood flow (FIG. 13A) compared to delivery of cells via intramuscular injection (FIG. 13B).
Figure 13B:
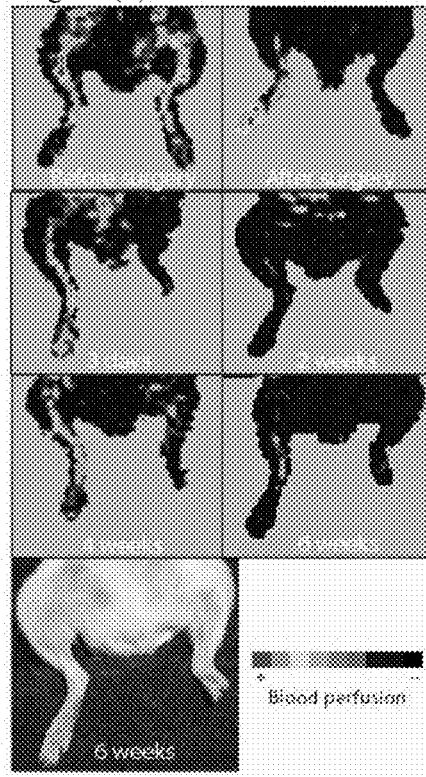
Figure 13C:
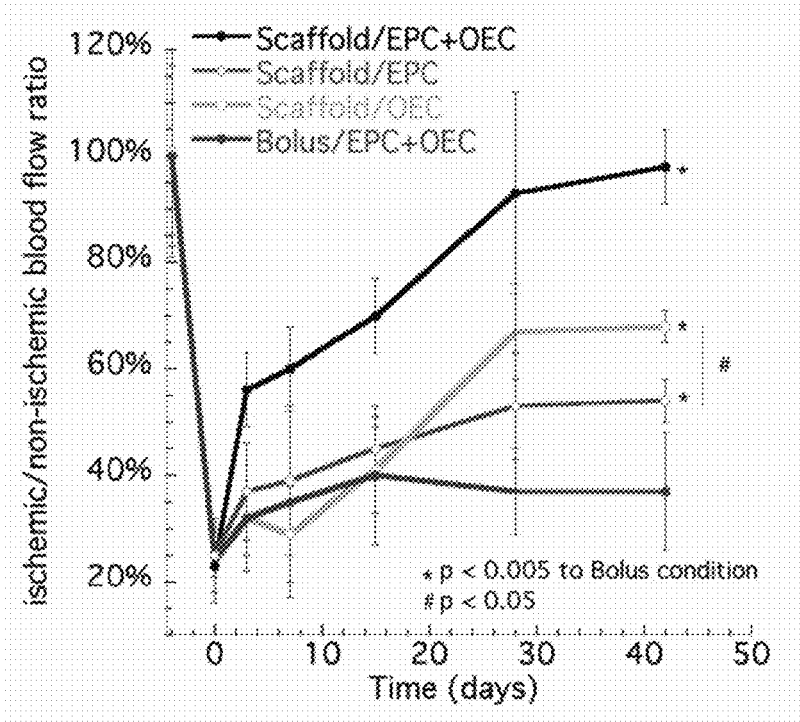
FIG. 13 C is a line graph showing that transplanting EPC and OEC within the gel matrix led to the complete recovery of blood flow in the hind limb in which the artery was ligated.
Figure 13D:
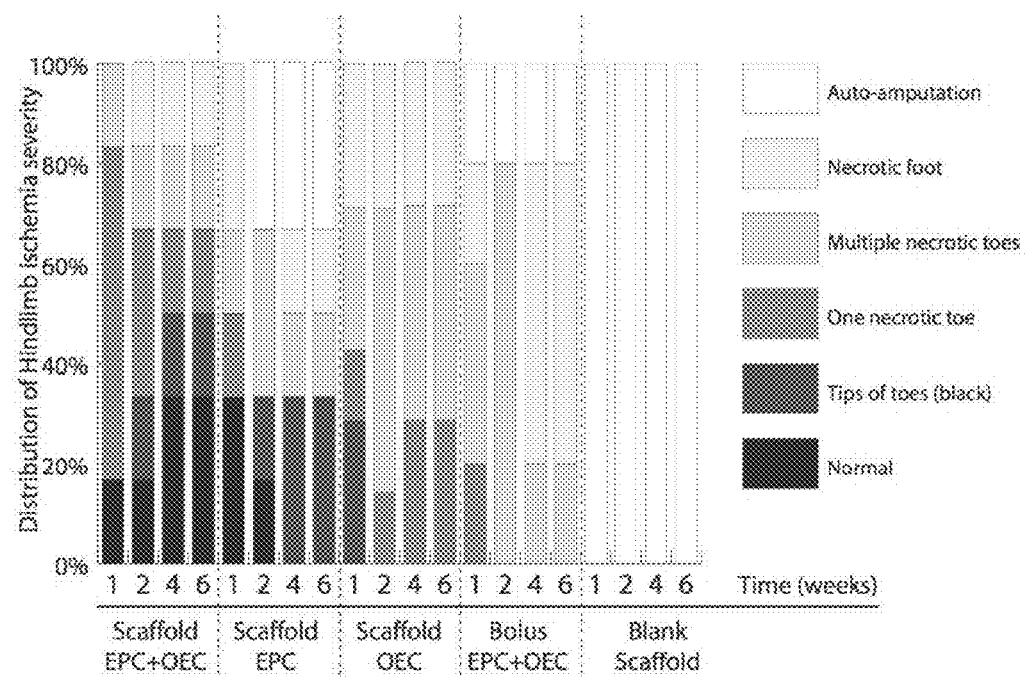
Figure 15:
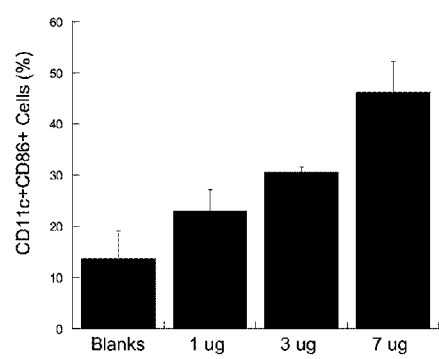
FIGS. 15A-B are bar graphs showing that DC infiltration is enhanced with an increase in the GM-CSF dose incorporated into PLG scaffolds.
Figure 15:
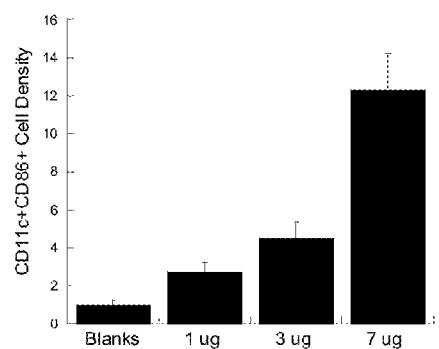

Human endothelial cells placed in matrices containing the RGD peptide migrated out of the alginate gel scaffolds and populated the surfaces of culture dishes in contact with the matrix, but their outward migration was significantly enhanced by the inclusion of VEGF in the matrix. A higher number of endothelial cells were localized in collagen and quantified at day 3 (FIG. 12) Transplanting EPC and OEC within synthetic microenvironments, including VEGF, completely recovered the blood perfusion in the right hind limb within 6 weeks (FIG. 13a). In contrast, the bolus injection of cells led to limited recovery of blood perfusion, and eventually the right hind limb was lost to necrosis (FIG. 13b). Transplanting both EPC and OEC within the gel matrix led to a superior recovery of blood perfusion, as compared with transplanting either EPC or OEC alone within the gel matrix (FIG. 13c). FIG. 13d further illustrates the recovery of blood perfusion in the animals tested. The device and cell niche system described above provides transplanted cells with the proper microenvironment that leads to synergistic enhancement of vascularization in vivo.

Example 5

Vaccine Devices that Regulate Cell Migration

Polymeric-based delivery systems were designed to regulate local in vivo cellular migration. Cells of the body into which the device is administered enter the device/scaffold, pick up an agent (e.g., a target antigen or immune stimulatory molecule), and later emigrate to distant sites. These types of polymeric systems are especially useful in tissue and cellular engineering applications or vaccination protocols that seek to deliver molecules, such as peptides, proteins, oligonucleotides, siRNA or DNA to specific target cells in vivo that effectively modulates their function. The device recruits cells of the body into the scaffold where the cells encounter agents that alter their function (e.g., the state of differentiation or activation), and the modified cells leave the implant site and have biological effects at diseased sites or elsewhere. Exit of the cells from the device is controlled by the composition, pore size, and or agents (e.g., cytokines) associated with the device.

Delivery of GM-CSF from poly-lactide-co-glycolide matrices promoted in vivo recruitment and infiltration of CD11c+ dendritic cells (DCs) in a dose dependant manner (FIGS. 14A-C and 15A-B). Incorporation of a fluorescent tag, fluoroscein, in the matrices permitted tracking of the migration of matrix of host DCs away from the scaffolds and into the draining lymph nodes using flow cytommetry (FIGS. 16A-C). GM-CSF delivery enhanced the total number of DCs in the lymph nodes that were derived from the implant site at days 14 and 28 after matrix implantation. These data indicate that the device scaffold systems effectively both promote the migration of cells into and out of a local site, in vivo, while picking up a bioactive agent, thereby modifying cell function such as immune activation.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cancer vaccine device comprising a scaffold composition comprising a polymer matrix and having open, interconnected macropores;
   a granulocyte-macrophage colony stimulating factor (GM-CSF) that recruits immune cells selected from macrophages, T-cells, B-cells, NK cells, and dendritic cells;
   a tumor antigen; and
   an immune response-promoting bioactive factor comprising an oligonucleotide, wherein the GM-CSF, the tumor antigen, or the immune response-promoting bioactive factor is incorporated into or coated onto said scaffold composition, wherein said device further comprises an extracellular matrix (ECM) component, and wherein the ECM component comprises an arginine-glycine-aspartate (RGD) sequence.

2. The device of claim 1, wherein the GM-CSF, tumor antigen, or immune response-promoting bioactive factor is covalently linked to said scaffold composition.

3. The device of claim 1, wherein the tumor antigen comprises biopsy-extracted antigens.

4. The device of claim 1, wherein the tumor antigen comprises a tumor cell lysate.

5. The device of claim 1, wherein the scaffold composition degrades at a predetermined rate based on a physical parameter selected from the group consisting of temperature, pH, hydration status, and porosity.

6. The device of claim 1, wherein the scaffold composition comprises pores of greater than 100 μm in size.

7. The device of claim 6, wherein the scaffold composition comprises pores of 400-500 μm in size.

8. The device of claim 1, wherein the tumor is chosen from a central nervous system (CNS) cancer, CNS germ cell tumor, lung cancer, leukemia, multiple myeloma, renal cancer, malignant glioma, ovarian cancer, prostate cancer, medulloblastoma, melanoma, breast cancer, ovarian cancer, Karposi's sarcoma, colon cancer, adenocarcinoma, brain cancer, testicular cancer, hepatocellular carcinoma, synovial sarcoma, and squamous cell carcinoma.

9. The device of claim 8, wherein the tumor is chosen from a melanoma, lung cancer, malignant glioma, and breast cancer.

10. The device of claim 1, wherein the device comprises PLGA microspheres.

11. The device of claim 1, wherein the device further comprises a vaccine adjuvant chosen from a chemokine, cytokine, and an antibody.

12. The device of claim 1, wherein the scaffold composition comprising open, interconnected macropores is made by gas foaming.

13. The device of claim 1, wherein the tumor antigen comprises a MAGE series of antigens, MART-1/melana, Tyrosinase, ganglioside, gp100, GD-2, 0-acetylated GD-3, GM-2, MUC-1, Sosl, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-Cl (cancer/testis antigen CT7), MAGE-B1 ANTIGEN (MAGE-XP ANTIGEN) (DAM10), MAGE-B2 ANTIGEN (DAME), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195, or Carcinoembryonic antigen (CEA).

14. The device of claim 1, wherein the immune response-promoting bioactive factor comprises a DNA molecule.

15. The device of claim 1, wherein the immune response-promoting bioactive factor comprises an RNA molecule.

16. The device of claim 1, wherein the immune response-promoting bioactive factor comprises a CpG rich oligonucleotide.

17. The device of claim 1, wherein the device is in a needle, endoscopic manipulator, catheter, surgical implantation tool, or minimally invasive surgical device.

18. The device of claim 1, wherein the polymer matrix comprises polylactic acid, polyglycolic acid, polyethylene glycol (PEG), poly(lactic-co-glycolic acid) (PLGA) polymer, alginate, alginate derivative, gelatin, collagen, fibrin, agarose, hyaluronic acid, natural polysaccharide, synthetic polysaccharide, polyamino acid, polyester, polyanhydride, polyphosphazine, poly(vinyl alcohol), poly(alkylene oxide), modified styrene polymer, pluronic polyol, polyoxamer, poly (uronic acid), poly(vinylpyrrolidone).

19. The device of claim 1, wherein the polymer matrix comprises poly(lactic-co-glycolic acid) (PLGA).

20. A cancer vaccine device comprising a scaffold composition comprising a polymer matrix and having open, interconnected macropores;
- a granulocyte-macrophage colony stimulating factor (GM-CSF) that recruits immune cells selected from macrophages, T-cells, B-cells, NK cells, and dendritic cells;
- a tumor antigen; and
- an immune response-promoting bioactive factor comprising an RNA molecule,
- wherein the GM-CSF, the tumor antigen, or the immune response-promoting bioactive factor is incorporated into or coated onto said scaffold composition.

21. The device of claim 20, wherein said device further comprises an extracellular matrix (ECM) component.

22. The device of claim 20, wherein said ECM component comprises an arginine-glycine aspartate (RGD) sequence.

23. The device of claim 20, wherein the GM-CSF, tumor antigen, or immune response-promoting bioactive factor is covalently linked to said scaffold composition.

24. The device of claim 20, wherein the tumor antigen comprises biopsy-extracted antigens.

25. The device of claim 20, wherein the tumor antigen comprises a tumor cell lysate.

26. The device of claim 20, wherein the scaffold composition degrades at a predetermined rate based on a physical parameter selected from the group consisting of temperature, pH, hydration status and porosity.

27. The device of claim 20, wherein said scaffold composition comprises pores of greater than 100 µm in size.

28. The device of claim 27, wherein the scaffold composition comprises pores of 400-500 µm in size.

29. The device of claim 20, wherein the tumor is chosen from a central nervous system (CNS) cancer, CNS germ cell tumor, lung cancer, leukemia, multiple myeloma, renal cancer, malignant glioma, ovarian cancer, prostate cancer, medulloblastoma, melanoma, breast cancer, ovarian cancer, Karposi's sarcoma, colon cancer, adenocarcinoma, brain cancer, testicular cancer, hepatocellular carcinoma, synovial sarcoma, and squamous cell carcinoma.

30. The device of claim 29, wherein the tumor is chosen from a melanoma, lung cancer, malignant glioma, and breast cancer.

31. The device of claim 20, wherein the device comprises PLGA microspheres.

32. The device of claim 20, wherein the device further comprises a vaccine adjuvant chosen from a chemokine, cytokine and an antibody.

33. The device of claim 20, wherein the scaffold composition comprising open, interconnected macropores is made by gas foaming.

34. The device of claim 20, wherein the tumor antigen comprises a MAGE series of antigens, MART-1/melana, Tyrosinase, ganglioside, gp100, GD-2, 0-acetylated GD-3, GM-2, MUC-1, Sosl, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-Cl (cancer/testis antigen CT7), MAGE-B1 ANTIGEN (MAGE-XP ANTIGEN) (DAM10), MAGE-B2 ANTIGEN (DAME), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195, or Carcinoembryonic antigen (CEA).

35. The device of claim 20, wherein the device is a needle, endoscopic manipulator, catheter, surgical implantation tool, or minimally invasive surgical device.

36. The device of claim 20, wherein the polymer matrix comprises polylactic acid, polyglycolic acid, polyethylene glycol (PEG), poly(lactic-co-glycolic acid) (PLGA) polymer, alginate, alginate derivative, gelatin, collagen, fibrin, agarose, hyaluronic acid, natural polysaccharide, synthetic polysaccharide, polyamino acid, polyester, polyanhydride, polyphosphazine, poly(vinyl alcohol), poly(alkylene oxide), modified styrene polymer, pluronic polyol, polyoxamer, poly(uronic acid), poly(vinylpyrrolidone).

37. The device of claim 20, wherein the polymer matrix comprises poly(lactic-co-glycolic acid) (PLGA).

* * * * *

UNITED STATES PATENT AND TRADEMARK OFFICE
CERTIFICATE OF CORRECTION

PATENT NO. : 9,132,210 B2  
APPLICATION NO. : 14/223759  
DATED : September 15, 2015  
INVENTOR(S) : David J. Mooney et al.

It is certified that error appears in the above-identified patent and that said Letters Patent is hereby corrected as shown below:

Specification

Replace the Government Support clause on Column 1, Lines 18-20 of the instant patent with the following statement:

--This invention was made with government support under HL069957 and DE013349 awarded by National Institutes of Health. The government has certain rights in the invention.--

Signed and Sealed this
Twenty-fourth Day of May, 2016

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 9
<212> TYPE: PRT
<213> ORGANISM: Homo sapiens

<400> SEQUENCE: 1

Gly Gly Gly Gly Arg Gly Asp Ser Pro
1               5

<210> SEQ ID NO 2
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Xaa Asx Asx Xaa Asx Xaa
1               5

<210> SEQ ID NO 3
<211> LENGTH: 6
<212> TYPE: PRT
<213> ORGANISM: Homo sapiens

<400> SEQUENCE: 3

Pro Arg Arg Ala Arg Val
1               5

<210> SEQ ID NO 4
<211> LENGTH: 19
<212> TYPE: PRT
<213> ORGANISM: Homo sapiens

<400> SEQUENCE: 4

Tyr Glu Lys Pro Gly Ser Pro Pro Arg Glu Val Val Pro Arg Pro Arg
1               5                   10                  15
```

Pro Gly Val

<210> SEQ ID NO 5
<211> LENGTH: 28
<212> TYPE: PRT
<213> ORGANISM: Homo sapiens

<400> SEQUENCE: 5

Arg Pro Ser Leu Ala Lys Lys Gln Arg Phe Arg His Arg Asn Arg Lys
1               5                   10                  15
Gly Tyr Arg Ser Gln Arg Gly His Ser Arg Gly Arg
            20                  25

<210> SEQ ID NO 6
<211> LENGTH: 17
<212> TYPE: PRT
<213> ORGANISM: Homo sapiens

<400> SEQUENCE: 6

Arg Ile Gln Asn Leu Leu Lys Ile Thr Asn Leu Arg Ile Lys Phe Val
1               5                   10                  15
Lys

<210> SEQ ID NO 7
<211> LENGTH: 5
<212> TYPE: PRT
<213> ORGANISM: Homo sapiens

<400> SEQUENCE: 7

Leu Arg Gly Asp Asn
1               5

<210> SEQ ID NO 8
<211> LENGTH: 5
<212> TYPE: PRT
<213> ORGANISM: Homo sapiens

<400> SEQUENCE: 8

Ile Lys Val Ala Val
1               5

<210> SEQ ID NO 9
<211> LENGTH: 5
<212> TYPE: PRT
<213> ORGANISM: Homo sapiens

<400> SEQUENCE: 9

Tyr Ile Gly Ser Arg
1               5

<210> SEQ ID NO 10
<211> LENGTH: 5
<212> TYPE: PRT
<213> ORGANISM: Homo sapiens

<400> SEQUENCE: 10

Pro Asp Ser Gly Arg
1               5

```
<210> SEQ ID NO 11
<211> LENGTH: 10
<212> TYPE: PRT
<213> ORGANISM: Homo sapiens

<400> SEQUENCE: 11

Arg Asn Ile Ala Glu Ile Ile Lys Asp Ala
1               5                   10
```